(12) United States Patent
Schuster et al.

(10) Patent No.: US 9,603,852 B2
(45) Date of Patent: Mar. 28, 2017

(54) TREATMENT OF OBESITY AND PULMONARY ARTERIAL HYPERTENSION

(71) Applicant: ALBERT EINSTEIN COLLEGE OF MEDICINE, INC., Bronx, NY (US)

(72) Inventors: Victor L. Schuster, New York, NY (US); Yuling Chi, New Rochelle, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 0 days.

(21) Appl. No.: 14/898,576

(22) PCT Filed: Jun. 17, 2014

(86) PCT No.: PCT/US2014/042628
§ 371 (c)(1),
(2) Date: Dec. 15, 2015

(87) PCT Pub. No.: WO2014/204895
PCT Pub. Date: Dec. 24, 2014

(65) Prior Publication Data
US 2016/0113933 A1    Apr. 28, 2016

Related U.S. Application Data

(60) Provisional application No. 61/836,200, filed on Jun. 18, 2013.

(51) Int. Cl.
*A61K 31/53* (2006.01)

(52) U.S. Cl.
CPC .................... *A61K 31/53* (2013.01)

(58) Field of Classification Search
None
See application file for complete search history.

(56) References Cited

U.S. PATENT DOCUMENTS

| 8,227,466 | B2 | 7/2012 | Schuster et al. |
| 8,952,150 | B2 * | 2/2015 | Schuster ............. 544/196 |
| 9,144,573 | B2 | 9/2015 | Schuster et al. |
| 2004/0204472 | A1 * | 10/2004 | Briggs ............ A61K 31/365 514/406 |
| 2012/0196881 | A1 | 8/2012 | Najarian et al. |

FOREIGN PATENT DOCUMENTS

| WO | 2011037610 A1 | 3/2011 | |
| WO | WO 2011037610 A1 * | 3/2011 | ........... A61K 9/0014 |

OTHER PUBLICATIONS

PCT International Search Report and Written Opinion, dated Oct. 10, 2014 in connection with PCT International Application No. PCT/US2014/42628, 10 pages.

Dingemanse J., et al. Treatment of obesity and pulmonary arterial hypertension with inhibitors of the prostaglandin transporter: evaluation of patent WO2014/204895A1. Expert Opin. Ther. Patents (2015) 25(9): 1-9.

Chi, Y. et al. Development of a high-affinity inhibitor of the prostaglandin transporter. J. Pharmacol. Exp. Therap. (2011) 339: 633-641.

Chi, Y. et al. Identification of a new class of prostaglandin transporter inhibitors and characterization of their biological effects on prostaglandin E2 transport. J. Pharmacol. Exp. Therap. (2006) 316: 1346-1350.

* cited by examiner

*Primary Examiner* — Heidi Reese
(74) *Attorney, Agent, or Firm* — Amster, Rothstein & Ebenstein LLP

(57) ABSTRACT

Disclosed are methods and compositions for treating pulmonary arterial hypertension and/or obesity using inhibitors of prostaglandin transporter (PGT) activity.

24 Claims, 7 Drawing Sheets

TREATMENT OF OBESITY AND PULMONARY ARTERIAL HYPERTENSION

CROSS-REFERENCE TO RELATED APPLICATIONS

This application is a U.S. national stage entry under 35 U.S.C. §371 of PCT International Patent Application No. PCT/US2014/042628, filed Jun. 17, 2014, which claims the benefit of U.S. Provisional Application No. 61/836,200, filed Jun. 18, 2013, the contents of each of which are incorporated herein by reference into the subject application.

BACKGROUND OF THE INVENTION

Various publications are referred to in parentheses throughout this application. Full citations for these references may be found at the end of the specification immediately preceding the claims. The disclosures of these publications are hereby incorporated by reference in their entireties into the subject application to more fully describe the art to which the subject application pertains.

Prostaglandins (PGs) are synthesized from arachidonic acid by cyclooxygenases (COX1 and COX2) and corresponding synthases (Helliwell et al. 2004). PGs play an important role in physiology and clinical settings. Their biological effects include triggering inflammation, fever and pain (Blatteis and Sehic, 1997; Bley et al., 1998; Vanegas and Schaible, 2001; Samad et al., 2002); induction of labor (Ulmann et al., 1992); modulation of renal hemodynamics and of water and solute reabsorption (Epstein, 1986; Wang et al., 1998; Yokoyama et al., 2002); arterial vasodilatation (Clyman et al., 1978; Coceani and Olley, 1988; Smith et al., 1994); stimulation of cell proliferation and angiogenesis (Ferrara et al, 1997; Tsujii et al, 1998; Young, 2004; Mann et al, 2006; Sheng et al, 2001; Shao et al, 2006); and mediating sensitization of sensory neurons (Southall and Vasko, 2000; Southall and Vasko, 2001; Seybold et al., 2003). PG analogues, such as latanoprost and unoprostone, have been used to treat glaucoma (Stjernschantz, 1995; Alm, 1998; Susanna et al., 2002; Stjernschantz, 2004). At the cellular level, PGs are involved in several major signaling pathways, including the mitogen-activated protein (MAP) kinase and protein kinase A pathways by upregulation of cAMP (Narumiya et al., 1999; Bos et al., 2004).

The magnitude of PG effects depends not only on their production but also their metabolism. The prostaglandin transporter (PGT) (Kanai et al., 1995; U.S. Pat. No. 5,792,851) removes PGs from the extracellular compartment and thereby terminates their interactions with receptors on cell membranes. PGT delivers PGs to cytoplasmic 15-OH PG dehydrogenase (Schuster, 2002; Nomura et al., 2004), resulting in oxidation and inactivation. Because PGT is highly expressed in the tissues and organs where PGs are synthesized (Bao et al., 2002), and because PGT regulates a broad and complex PG signaling system, inhibitors of PGT are important for manipulating signaling. Inhibition of PGT lowers blood pressure by vasodilation and natriuresis and inhibits platelet aggregation.

Known PGT blockers include inhibitors of the organic anion transporters (OATs), such as bromcresol green and bromosulfophthalein, and some COX2 inhibitors, such as indomethacin and ibuprofen (Bito and Salvador, 1976; Kanai et al., 1995). One of the main problems with these inhibitors is that they are not specific for PGT (Jacquemin et al., 1994; Sweet et al., 1997). Recently, specific PGT inhibitors have been developed (Chi et al., 2005; WO 2007/136638; US 2012/0238577).

Obesity is a world-wide epidemic associated with significant morbidity and mortality which costs billions of dollars per year (e.g., Carter et al., 2012; Holes-Lewis et al., 2013; Santo-Domingo et al. 2012). The need for more effective medications and treatments remains clear.

Pulmonary arterial hypertension (PAH) is a chronic progressive disease of the pulmonary vasculature characterized by elevated pulmonary arterial pressure and secondary right ventricular failure, with an estimated incidence of 1-2 cases per 1 million persons in the general population (Patel et al., 2012). Despite advances in diagnosis and treatment, new therapeutic strategies are urgently required (Agarwal and Gomberg-Maitland, 2012; Yao, 2012).

The present invention addresses the need for treatments for pulmonary arterial hypertension and obesity, using inhibitors of PGT.

SUMMARY OF THE INVENTION

The invention provides methods of treating obesity and/or pulmonary arterial hypertension comprising administering to a subject having obesity and/or pulmonary arterial hypertension a compound of formula (I) in an amount effective to treat obesity and/or pulmonary arterial hypertension, wherein formula (I) is:

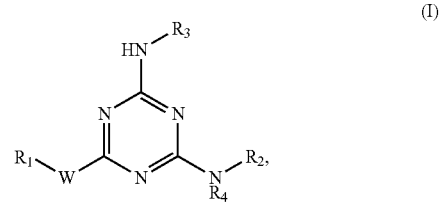

where the variables R1, R2, R3, R4 and W are defined herein below.

The invention also provides methods of treating a condition selected from the group consisting of obesity and pulmonary arterial hypertension comprising administering to a subject having obesity and/or pulmonary arterial hypertension a prostaglandin transporter inhibitor in an amount effective to treat obesity and/or pulmonary arterial hypertension.

The invention further provides pharmaceutical compositions for treating obesity and/or pulmonary arterial hypertension comprising a compound of formula (I) in an amount effective to treat obesity and/or pulmonary arterial hypertension and a pharmaceutically acceptable carrier.

The invention also provides pharmaceutical compositions for treating obesity and/or pulmonary arterial hypertension comprising a prostaglandin transporter inhibitor in an amount effective to treat obesity and/or pulmonary arterial hypertension and a pharmaceutically acceptable carrier.

DETAILED DESCRIPTION OF THE INVENTION

Figures 1A, 1B, 1C:
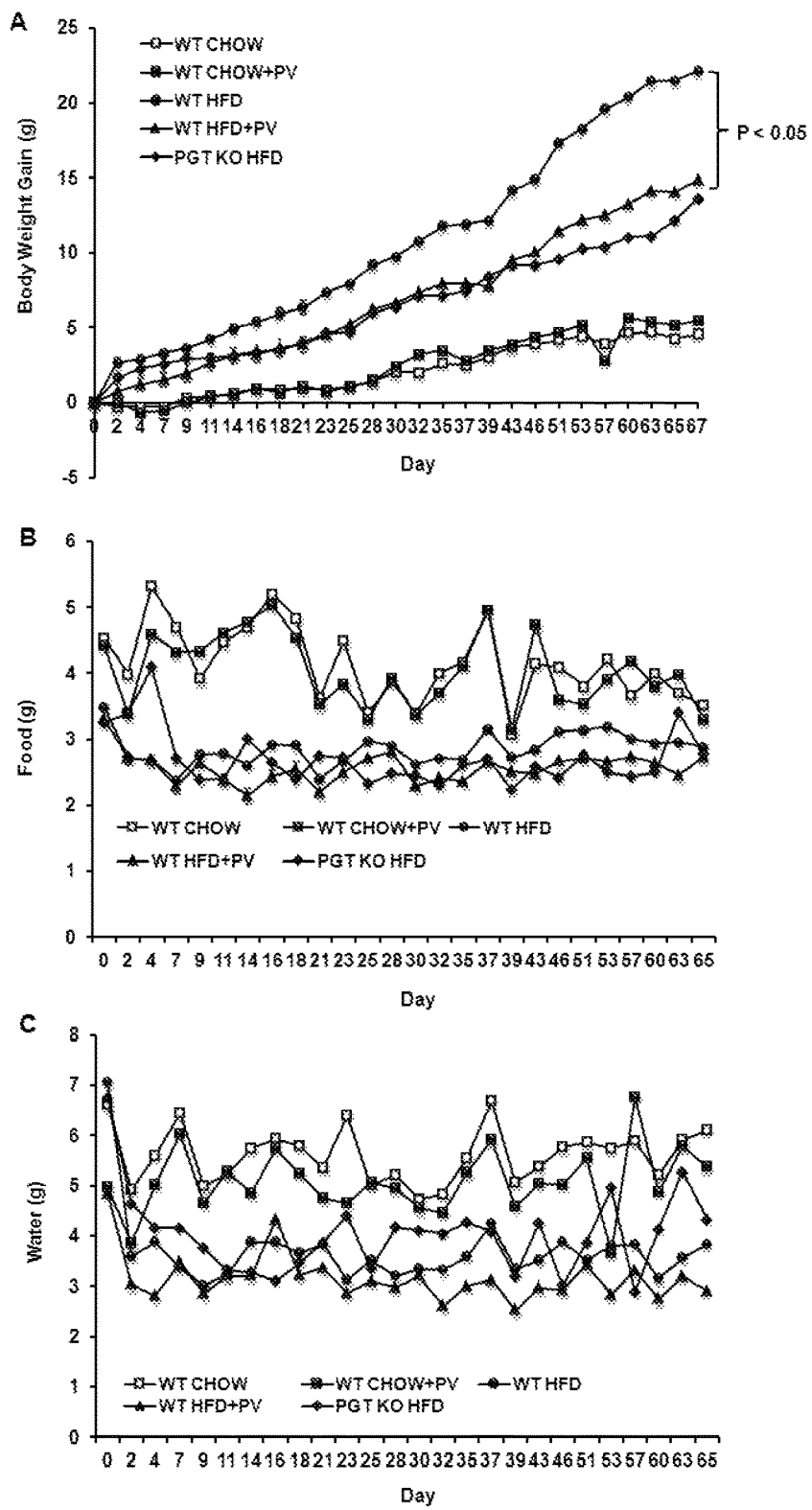
FIG. 1A-1C. WT C57BL6 and PGT Knock-out (KO) mice were fed with chow diet (CD) or high fat diet (HFD) and treated with vehicle (0.4% DMSO+0.4% cremophore) or 0.2 mM Compound 146 ("PV") in drinking water. Mice were housed individually and fed with CD or HFD, and water (with or without Compound 146) ad libitum. Body weight gain (A), food (B) and water (C) intake were recorded every other day. (n=3-4).

The invention provides a method of treating a condition selected from the group consisting of obesity and pulmonary arterial hypertension comprising administering to a subject having obesity and/or pulmonary arterial hypertension a compound of formula (I) in an amount effective to treat obesity and/or pulmonary arterial hypertension, wherein formula (I) is:

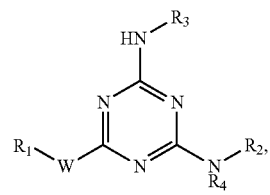

wherein
W is O or NR5;
R1 is H, —$CH_3$, —$(CH_2)_2OH$,

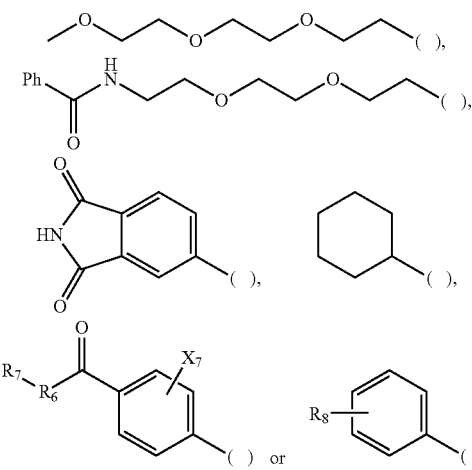

R2 is

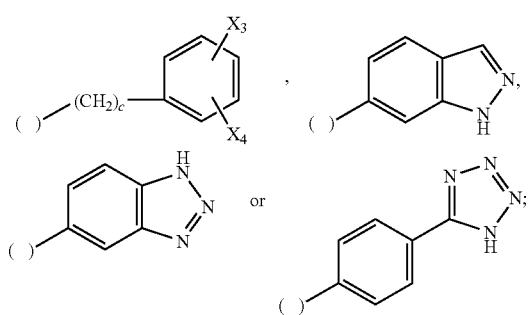

R3 is —$(CH_2)_5CH_3$, —$(CH_2)_6CO_2H$, —$(CH_2)_6CO_2CH_3$, —$(CH_2)_dNHCO$-Ph, —$(CH_2)_6CONH$-Ph, —$(CH_2)_6CONHCH_2$-Ph,

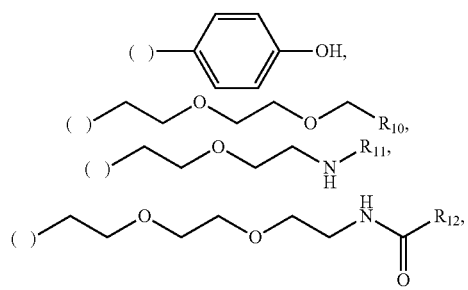

-continued

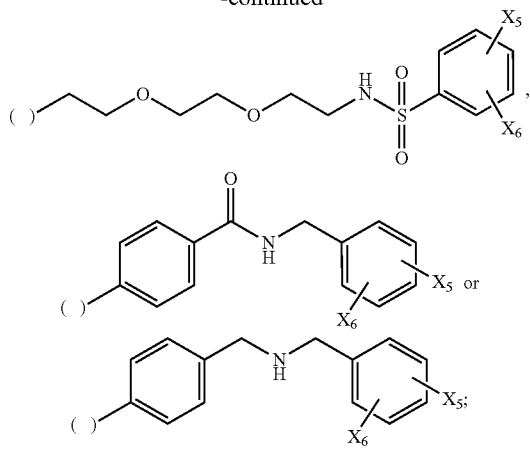

R4 and R5 are independently H or —CH₃;
R6 is O or NR9;
R7 is H, —CH₃, —C(CH₃)₃, —CH₂OH, —(CH₂)₂OH, —(CH₂)₂O(CH₂)₂OH, —(CH₂CH₂O)₃CH₃, —(CH₂CH₂O)₂CH₂CO₂CH₃, —(CH₂)₅CH₃,

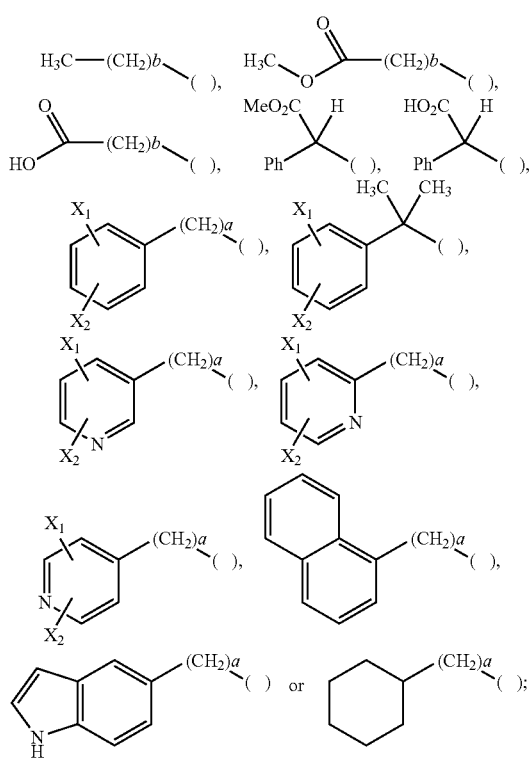

R8 is H, —OH, —CH₂OH, —CO₂H, —CO₂CH₂CH₃, —CO(CH₂)₆CH₃, —OCH₃, —NH₂, —SO₂NH₂, —CONH-Bn or

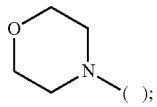

R9 is H or —CH₃;
R10 is —CH₂NH₂, —CO₂H or —CO₂CH₃;
R11 is —SO₂-Ph, —CH₂-Ph, —CONH-Ph, —COCH₃,

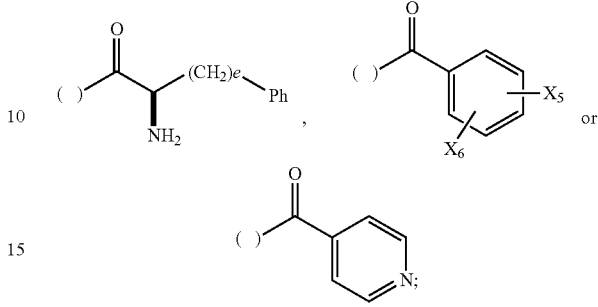

and
R12 is —CH₃, where X1, X2, X3, X4, X5, X6 and X7 are independently H, halogen, —OH, —CH₃, —CF₃, —OCH₃, —CO₂H, —CO₂CH₃, —CH₂CO₂H, —CH₂CO₂CH₃, phenyl or —O-Bn; and where a=0-2; b=1-6; c=0-1; d=4-7; and e=0-1; or a pharmaceutically acceptable salt thereof.

As used herein in chemical structures, "Ph" stands for phenyl, "Bn" stands for benzyl (—CH₂Ph), "Bz" stands for benzoyl (—(C=O)Ph), and "Me" stands for methyl (—CH₃). The point of attachment of the side group substitution to the main part of the compound is indicated by "( )." The terms ortho, meta and para refer to the positions of substitutions in relation to the main part of the compound.

In preferred compounds, W is NR5. In preferred compounds, R6 is NR9.

In preferred compounds, at least one of R4, R5 and R9 is H, or all of R4, R5 and R9 are H. Preferably, at least R5 (out of R4, R5 and R9) is H.

In preferred compounds, one of X1 and X2 is H, and the other is halogen, —CF₃, —CH₃, —CO₂H, —CO₂CH₃, —OCH₃ or phenyl. In preferred compounds, one of X3 and X4 is —OH, and the other is halogen, —CO₂H or —CO₂CH₃. In preferred compounds, X7 is H, —CF₃ or —OCH₃.

In preferred compounds, one or both of X1 and X2 are located in ortho position, or one or both of X1 and X2 are located in meta position, or X1 is located in meta position and X2 is located in para position, or X1 is located in ortho position and X2 is located in para position. In preferred compounds, X3 is in meta position and X4 is in para position. In preferred compounds, X5 or X6 is in meta position, or X5 or X6 is in para position.

Preferred compounds have the structure:

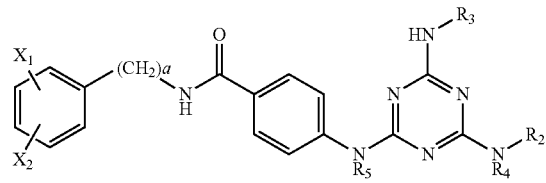

or

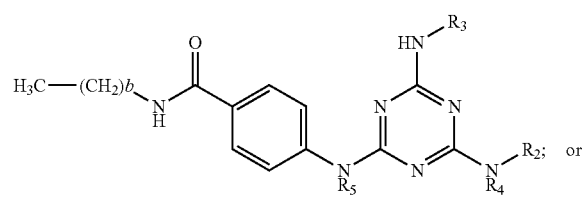

or

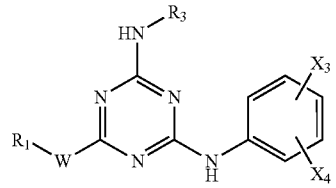

or

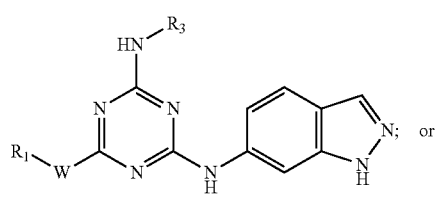

or

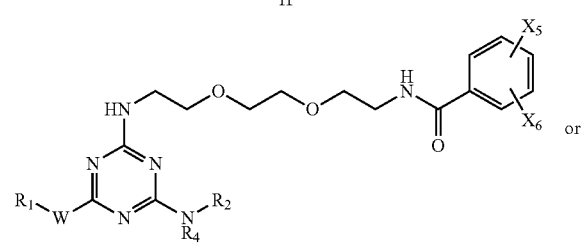

or

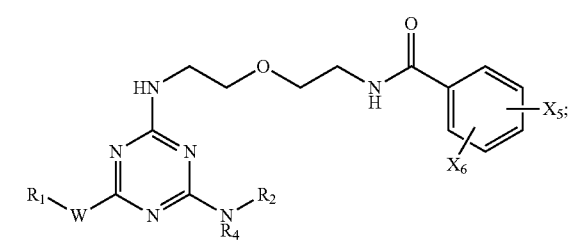

or a pharmaceutically acceptable salt thereof.

In preferred compounds,
R1 is

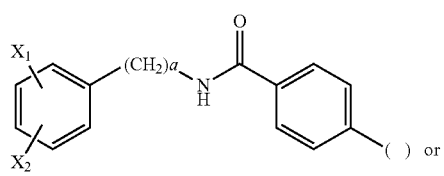

or

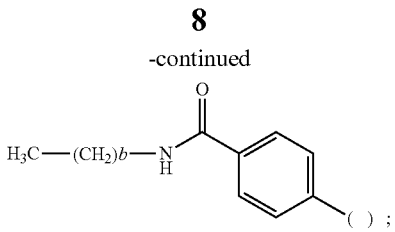

R2 is

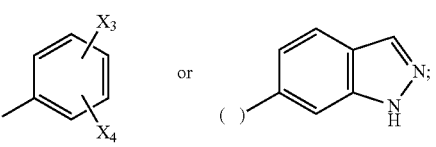 or 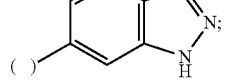

and
R3 is

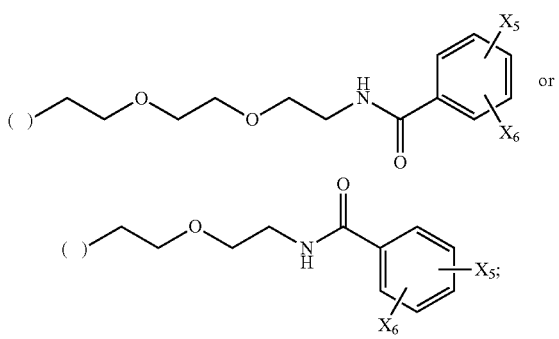

where X1, X2, X3, X4, X5 and X6 are independently H, halogen, —OH, —CH$_3$, —CF$_3$, —OCH$_3$, —CO$_2$H, —CO$_2$CH$_3$, —CH$_2$CO$_2$H or —CH$_2$CO$_2$CH$_3$; and where a=1-2; and b=1-5; or a pharmaceutically acceptable salt thereof.

In preferred compounds,
R1 is

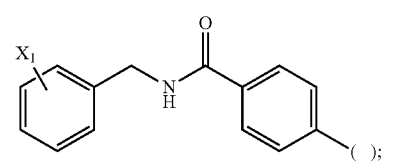

R2 is

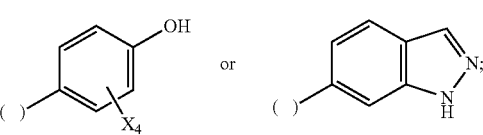 or 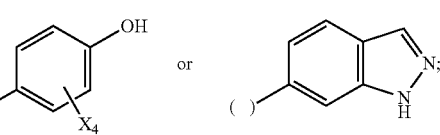

and
R3 is
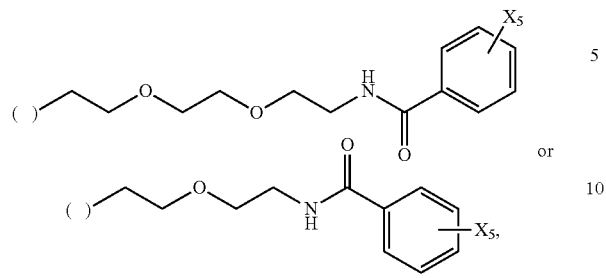
where X1 is H or halogen; where X4 is H, halogen or —CO₂H; and where X5 is H, halogen or —OCH₃; or a pharmaceutically acceptable salt thereof.
Preferred compounds have the structure:
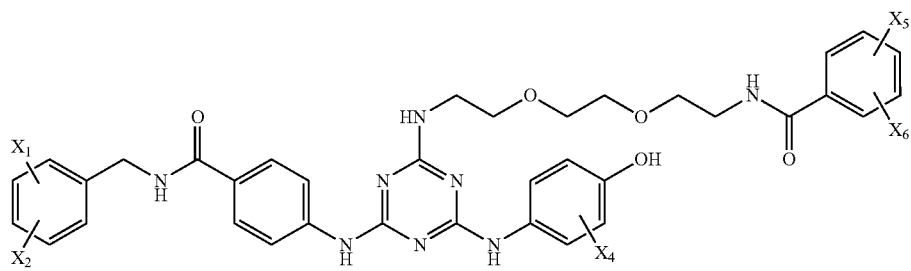
or a pharmaceutically acceptable salt thereof.
In the compounds described herein, W—R1 can be replaced with halogen.
Halogens are F, Cl, Br, I and At. Preferred halogens are Br, Cl and F.
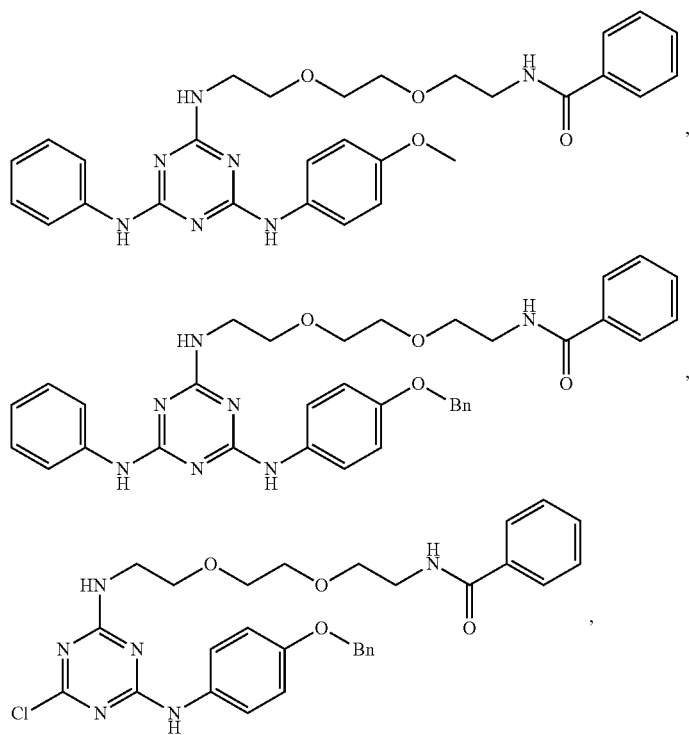

-continued
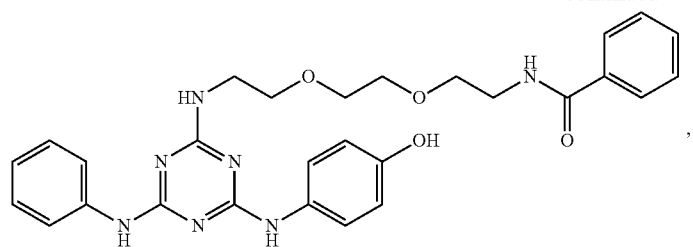
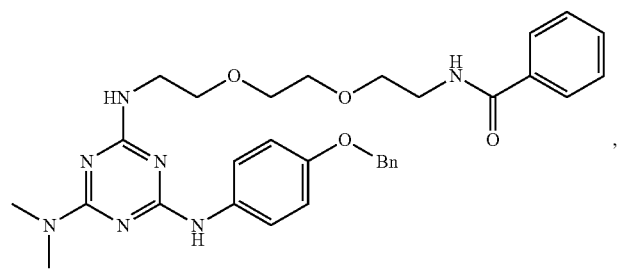
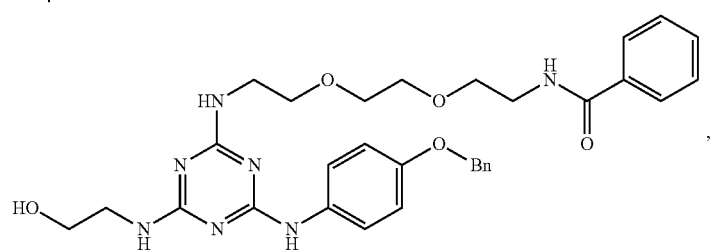
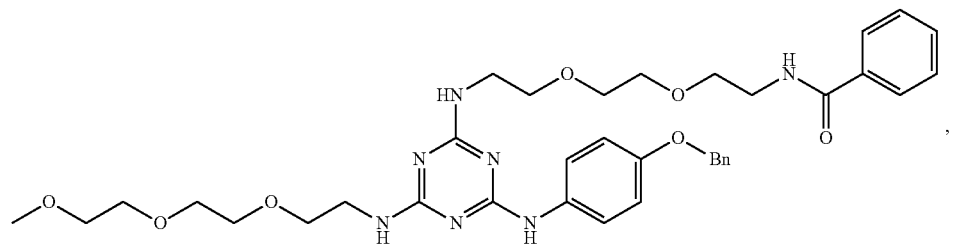
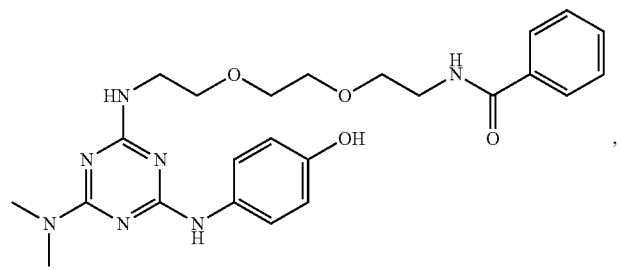
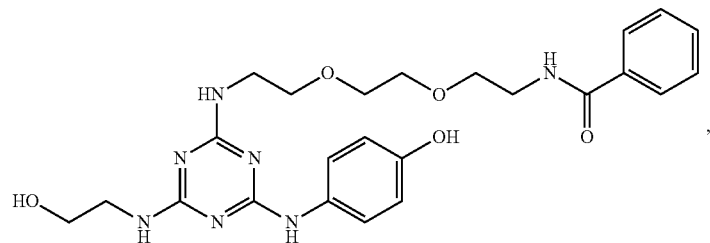

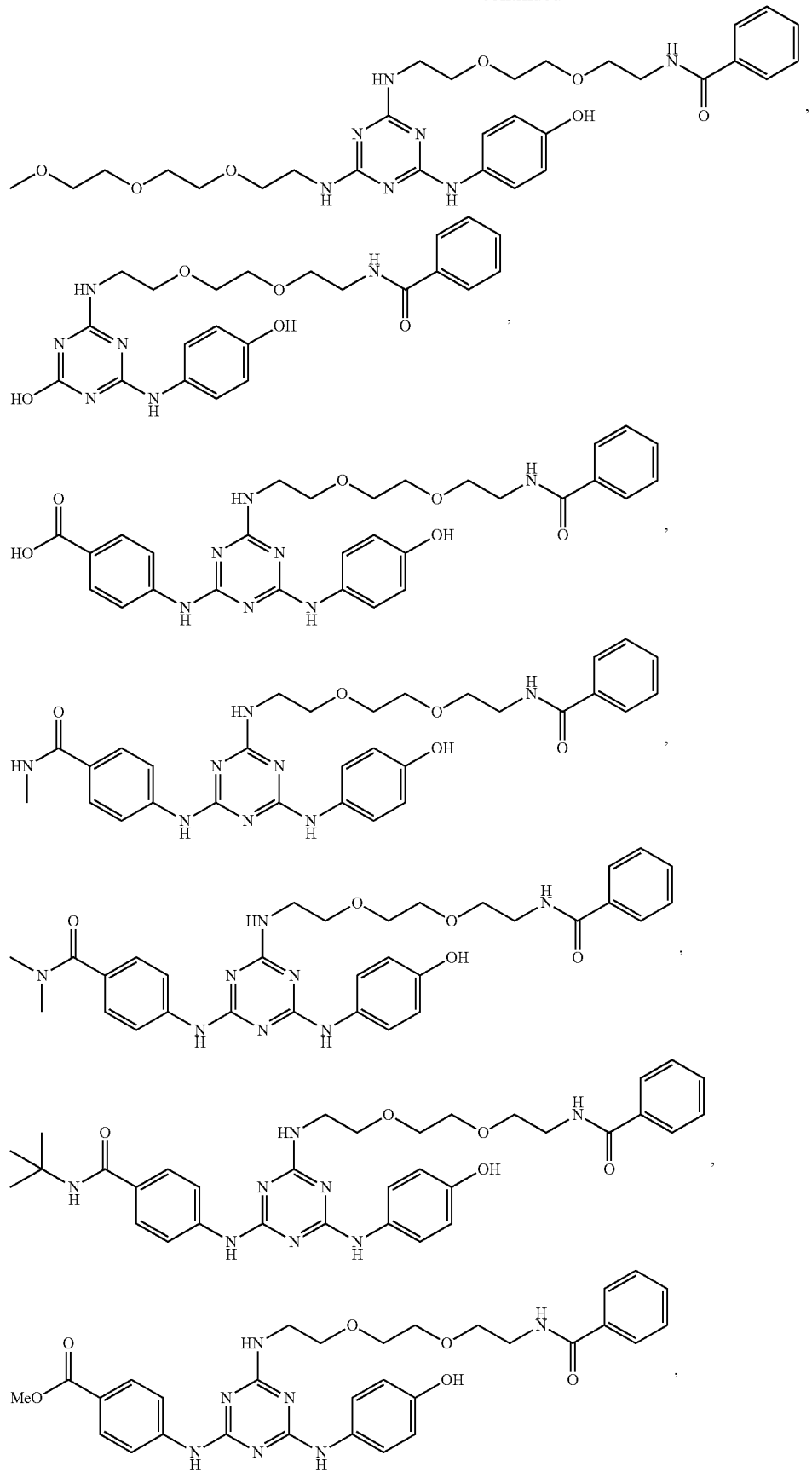

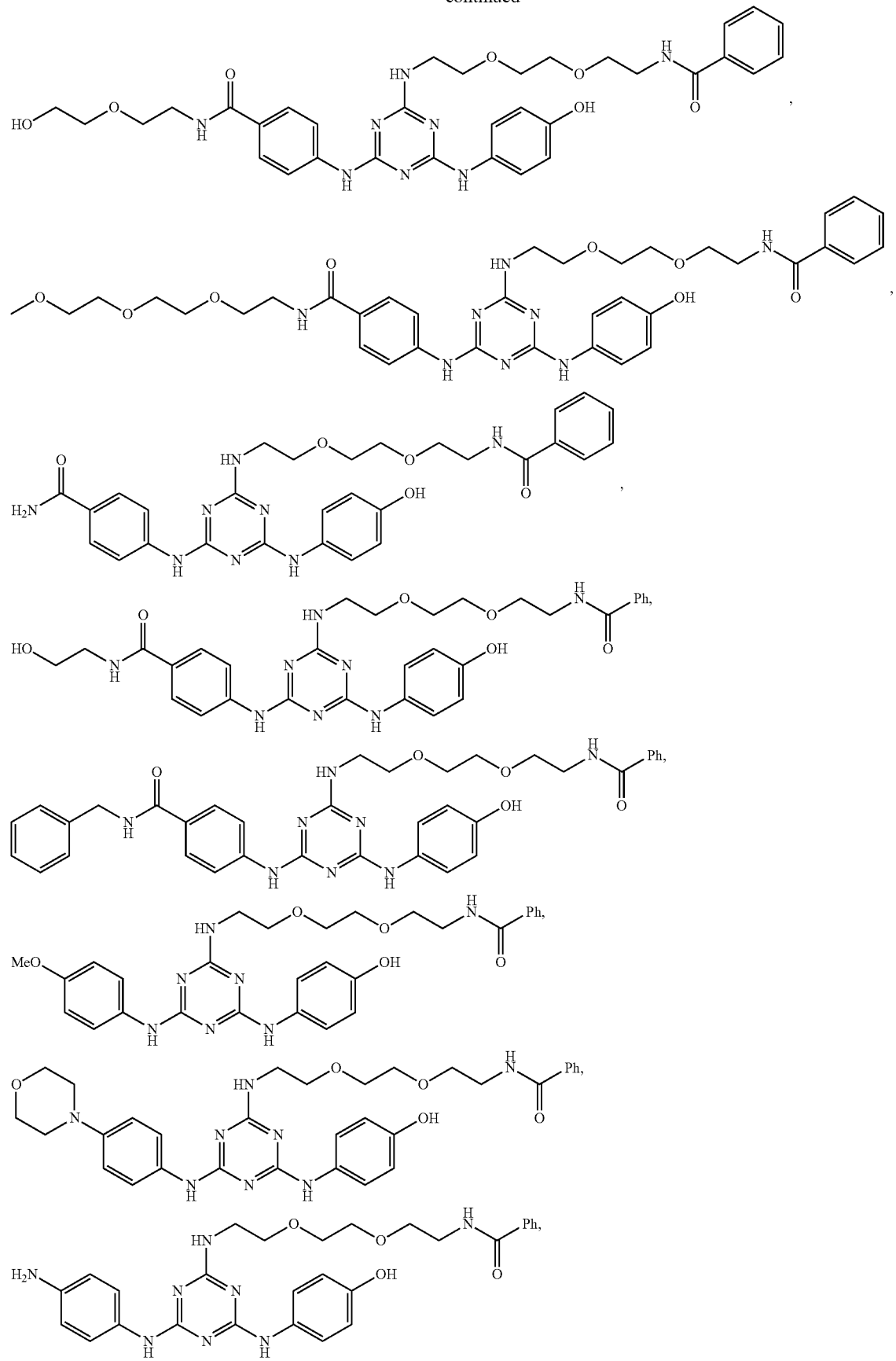

-continued
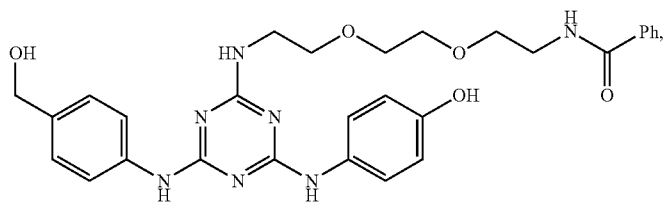
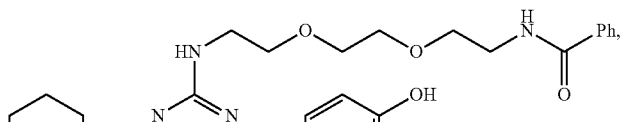
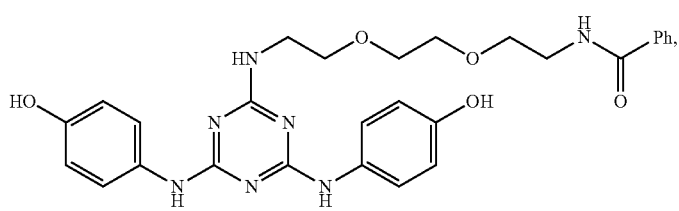
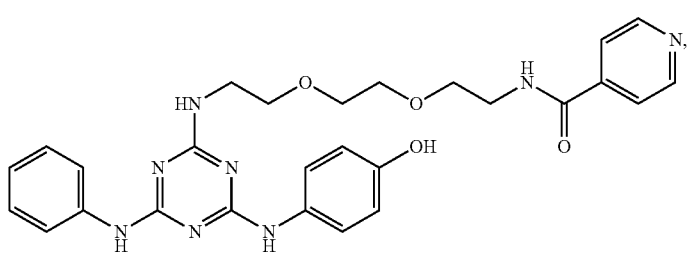
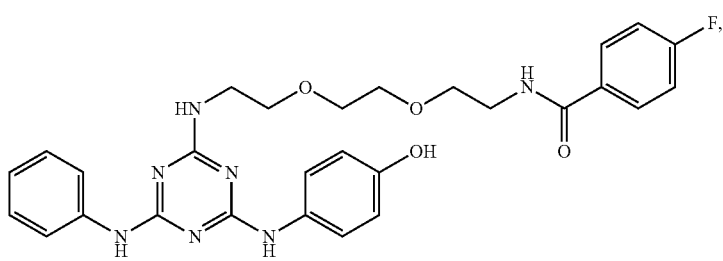
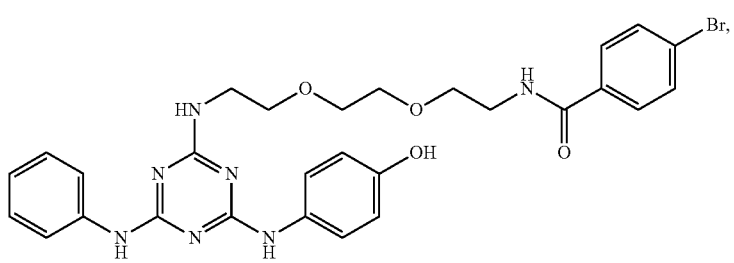
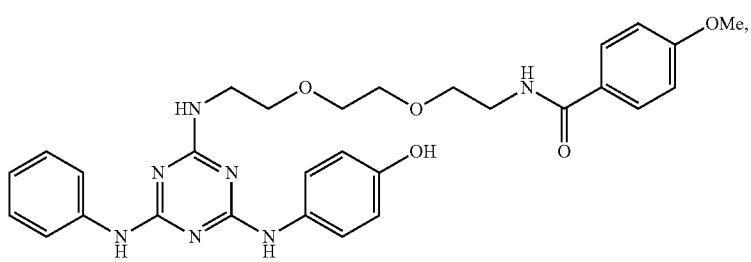

-continued
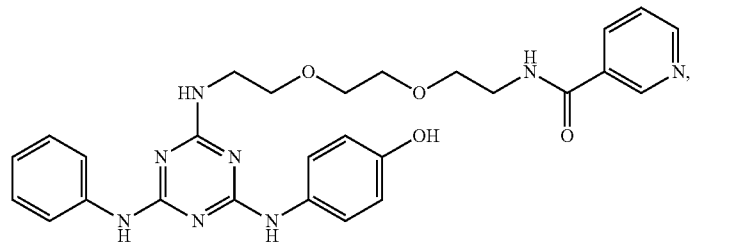
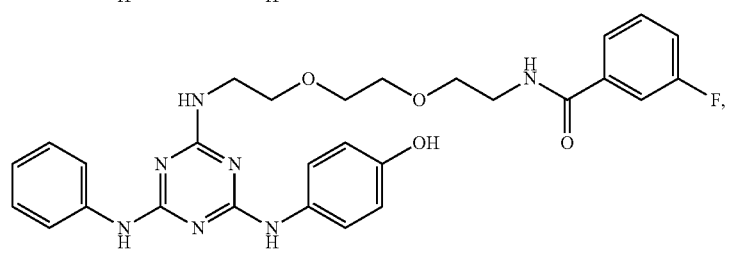
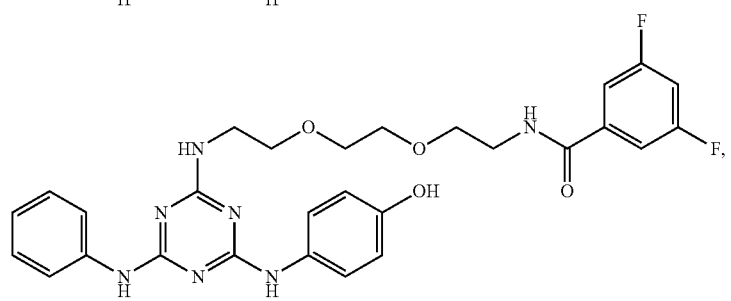
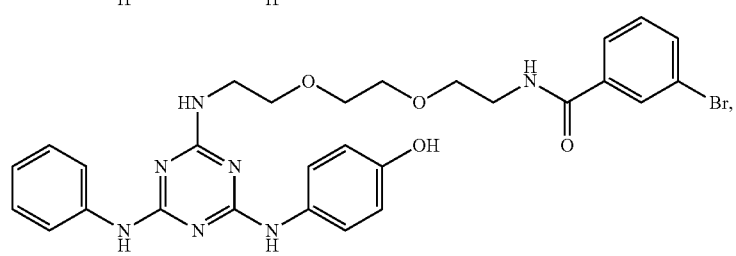
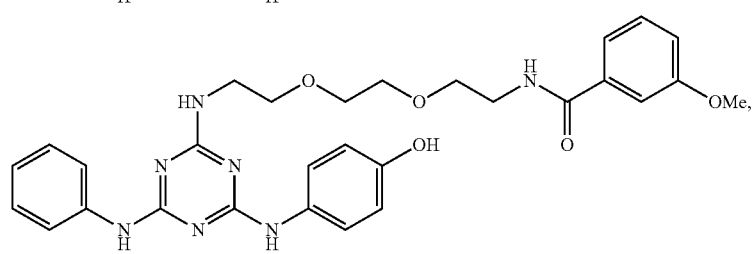
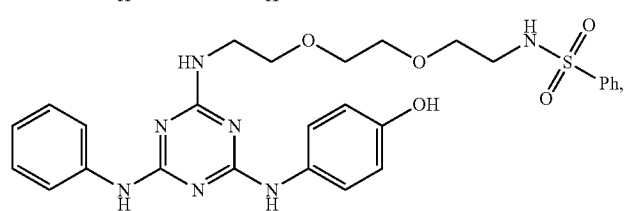
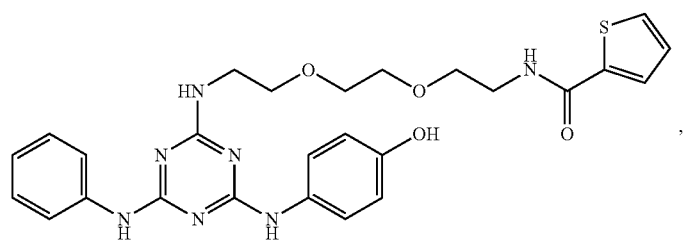

-continued
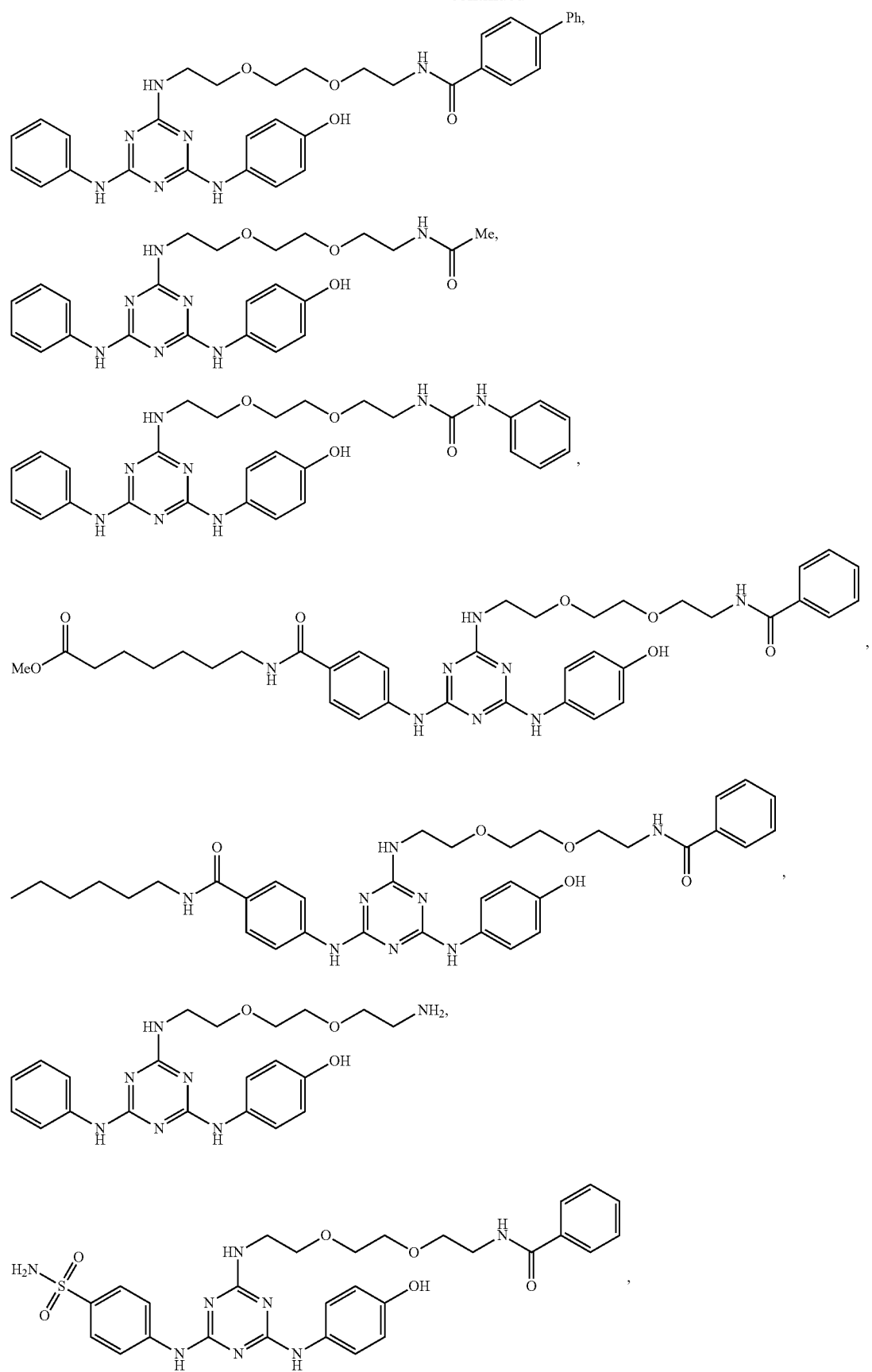

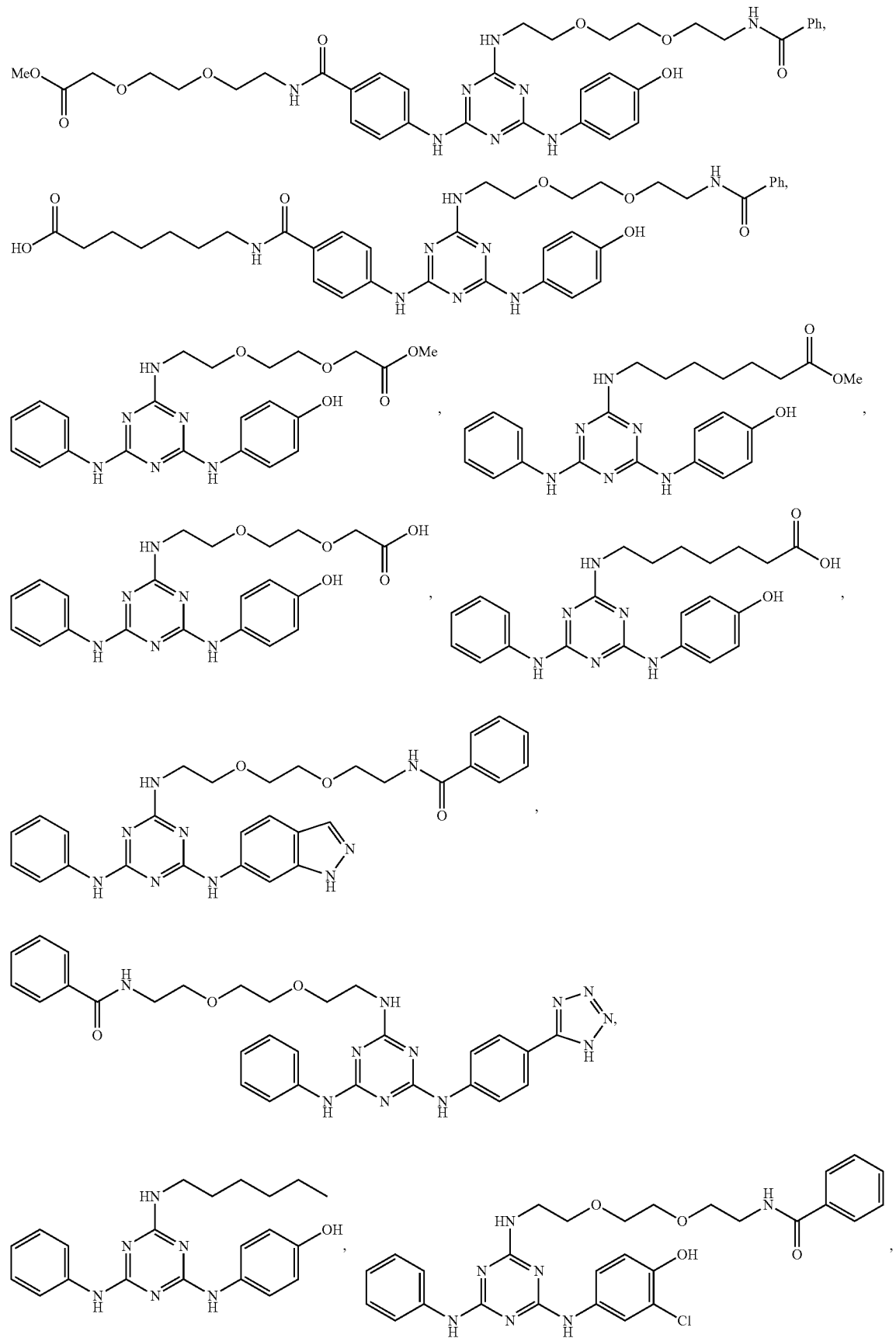

-continued
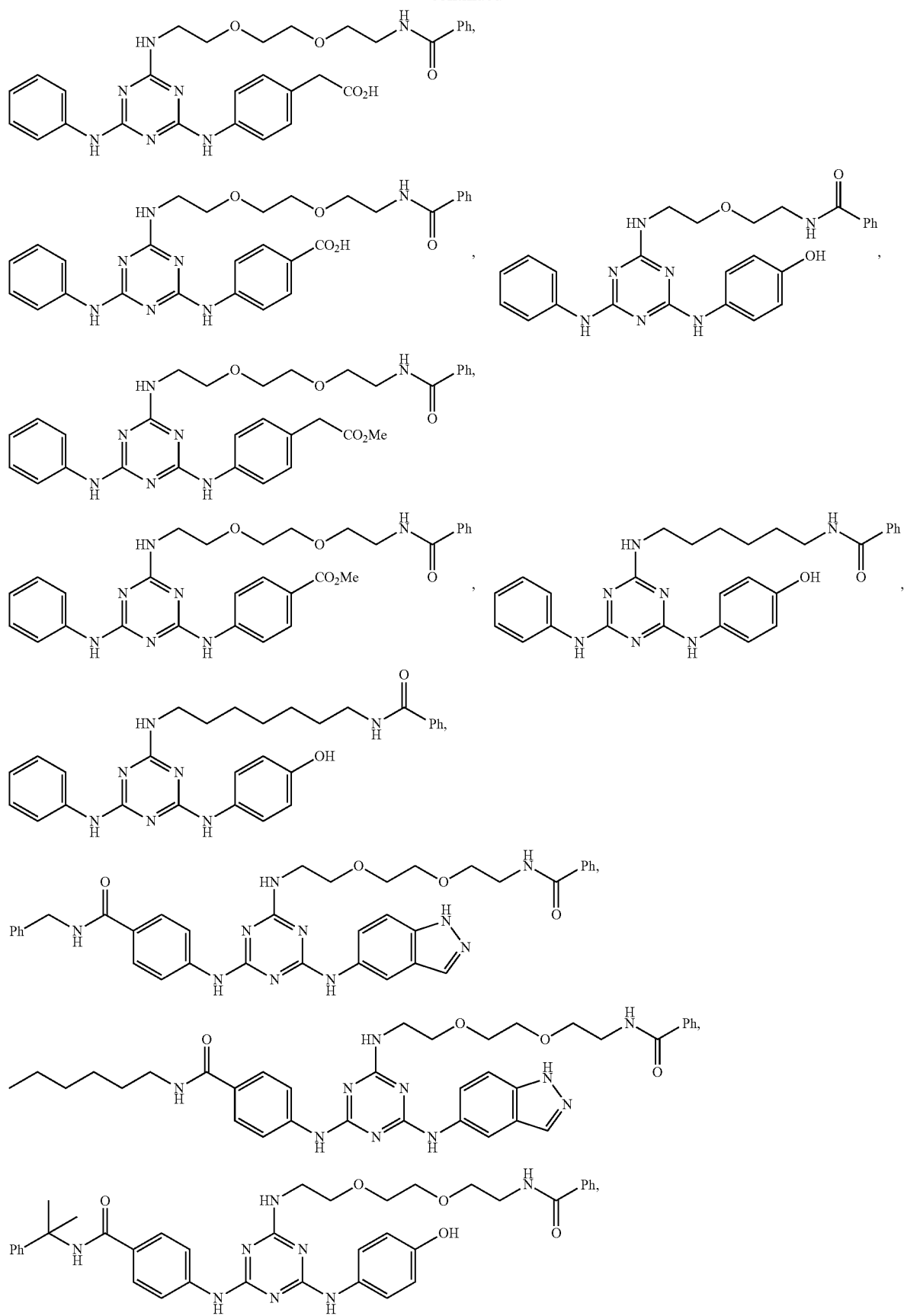

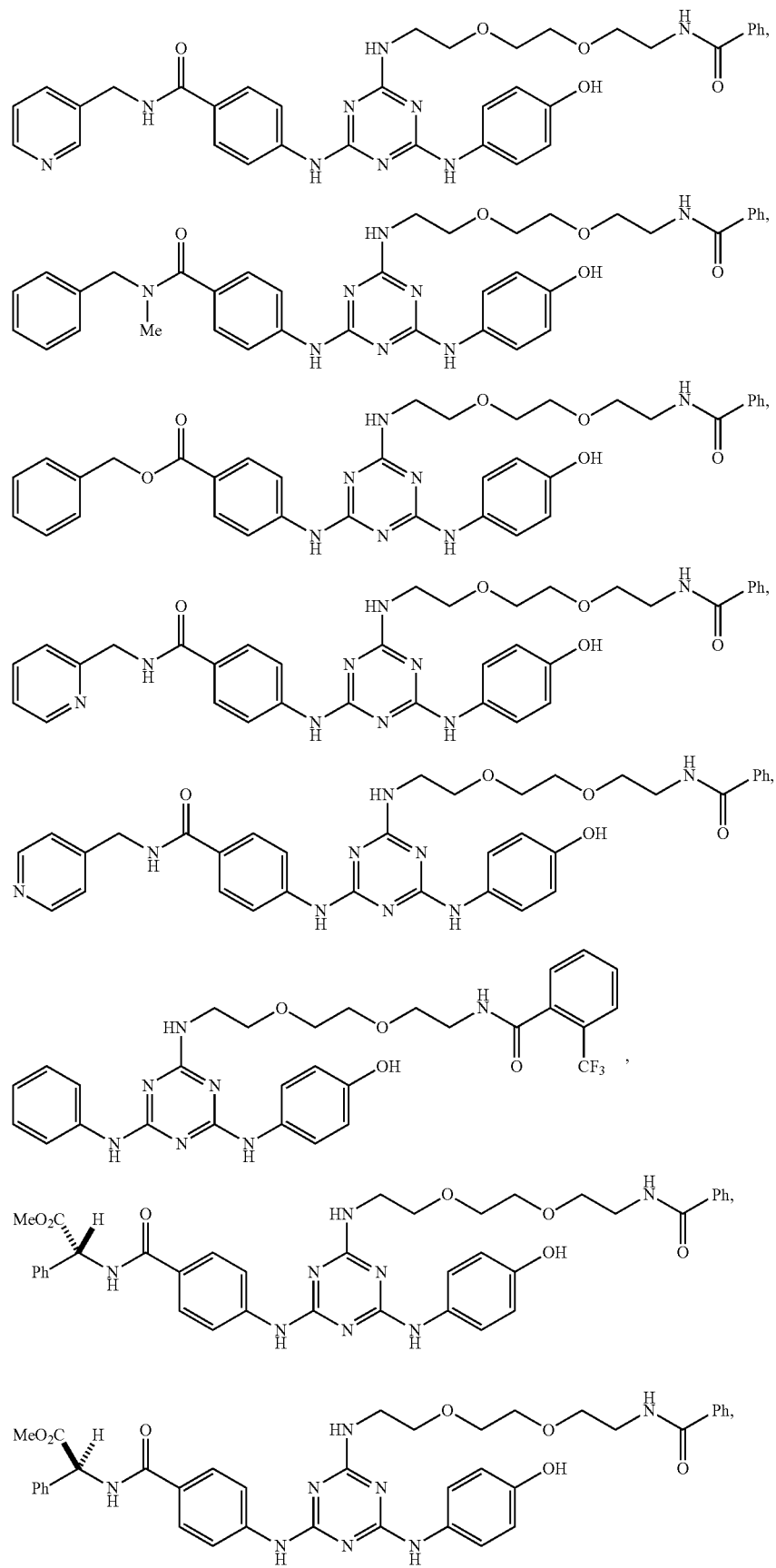

-continued
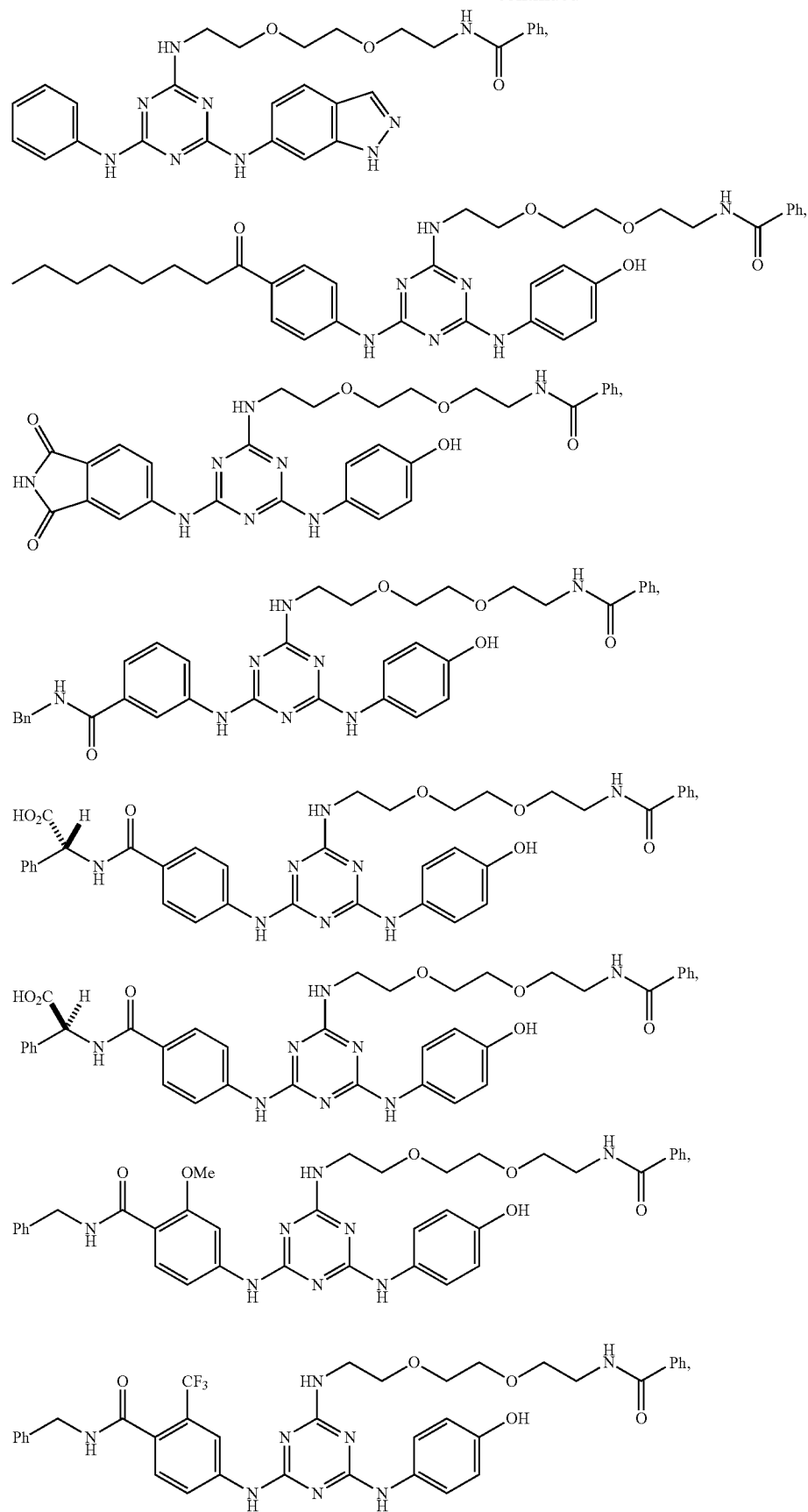

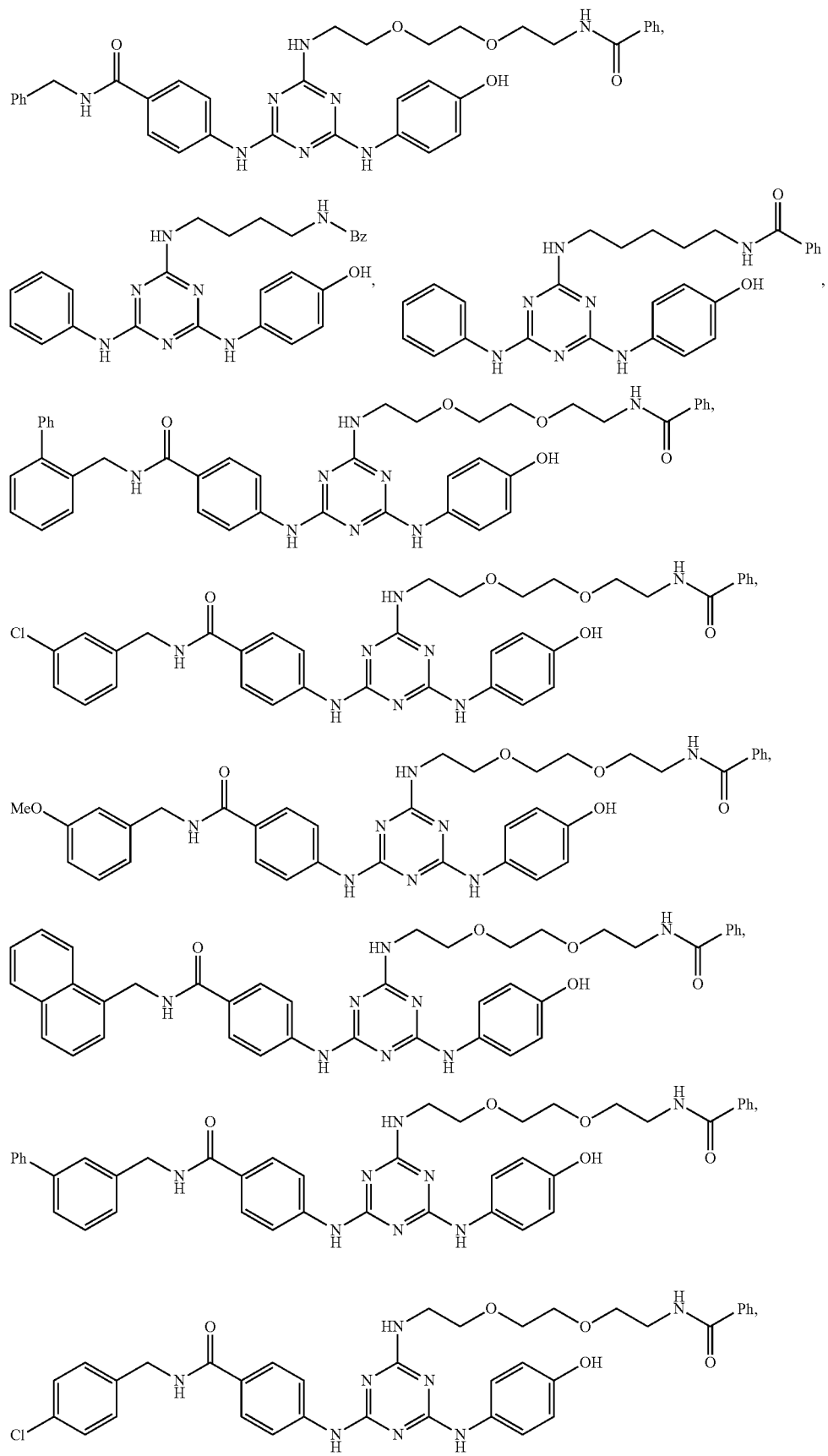

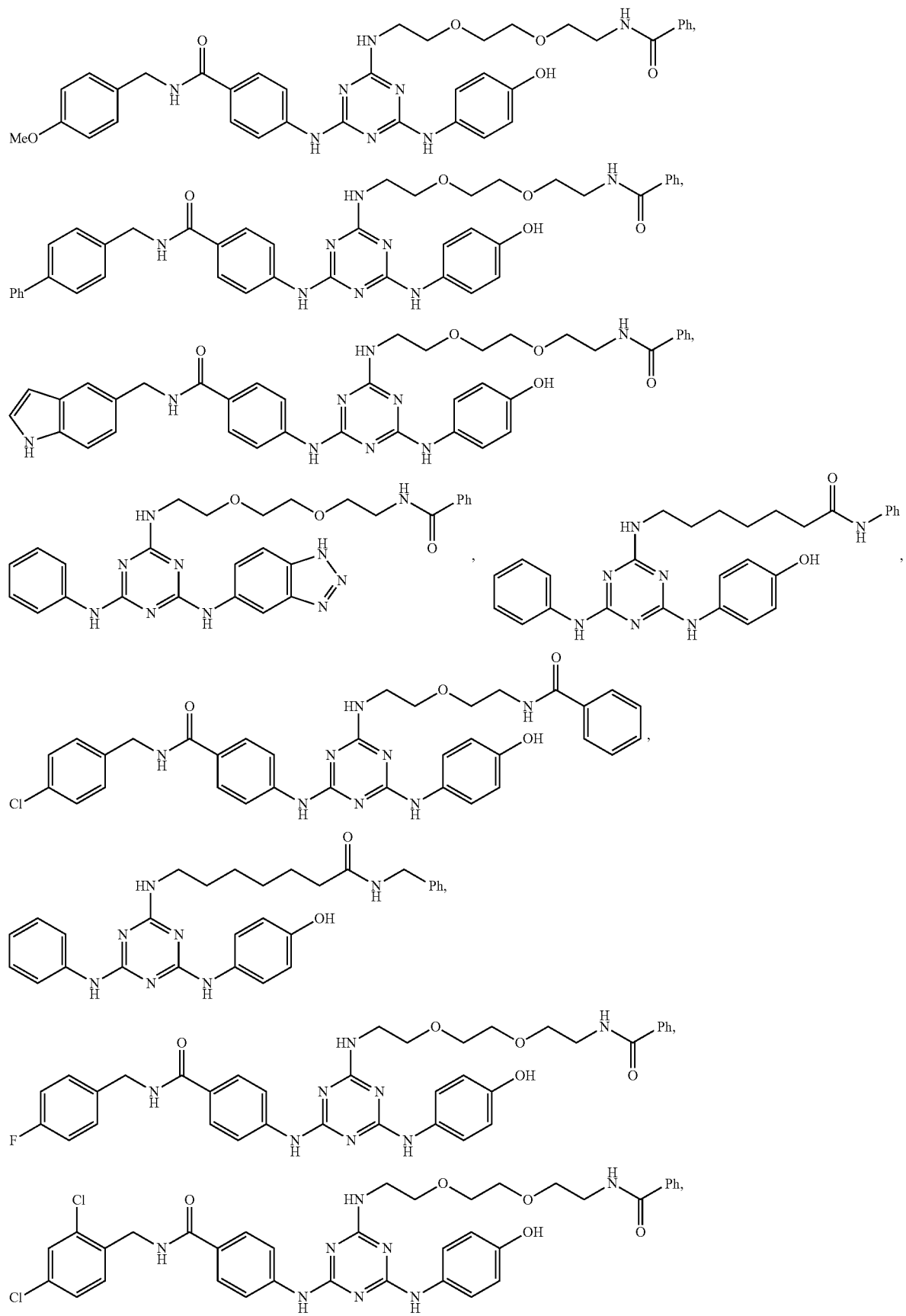

-continued
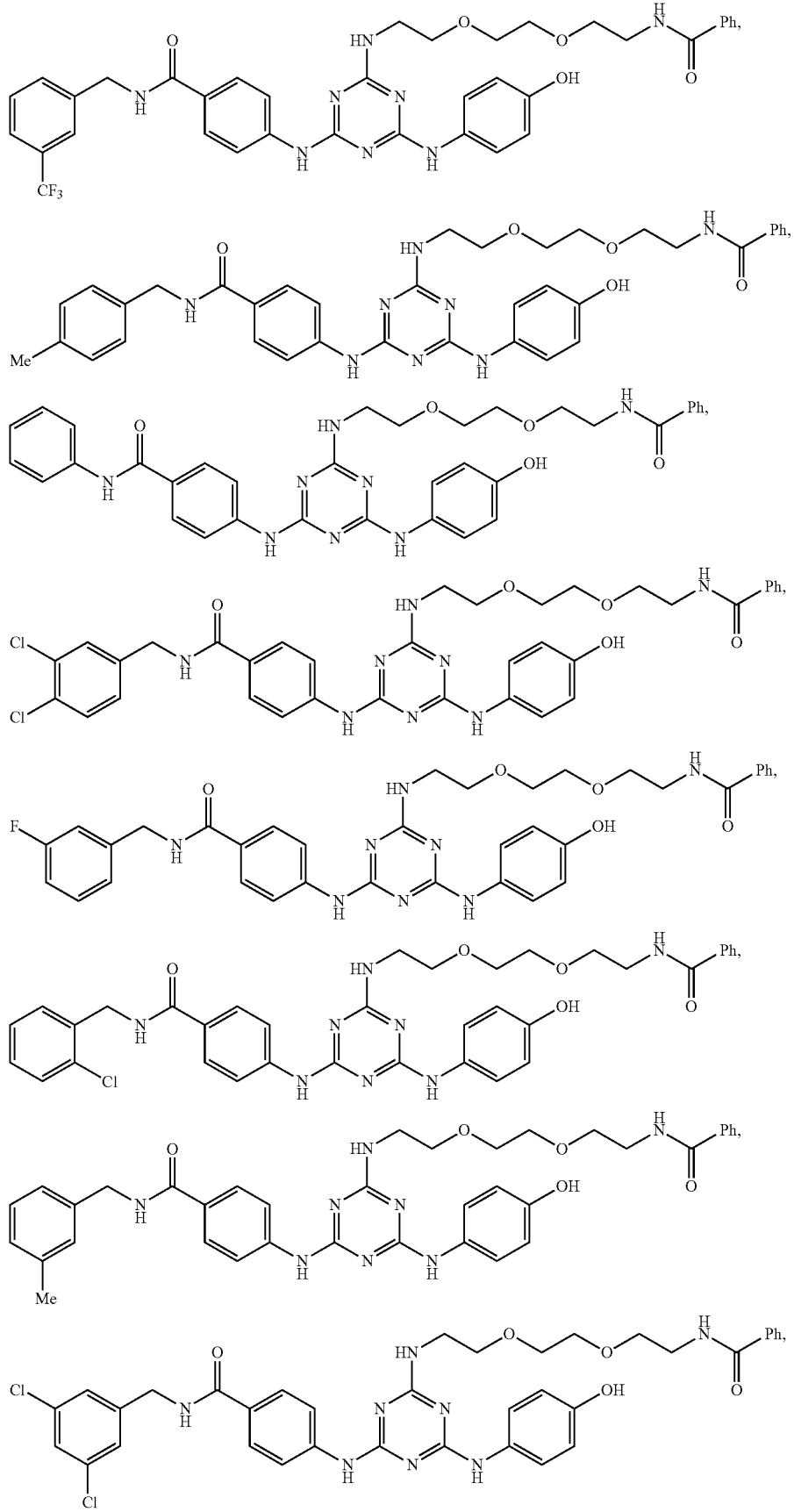

-continued
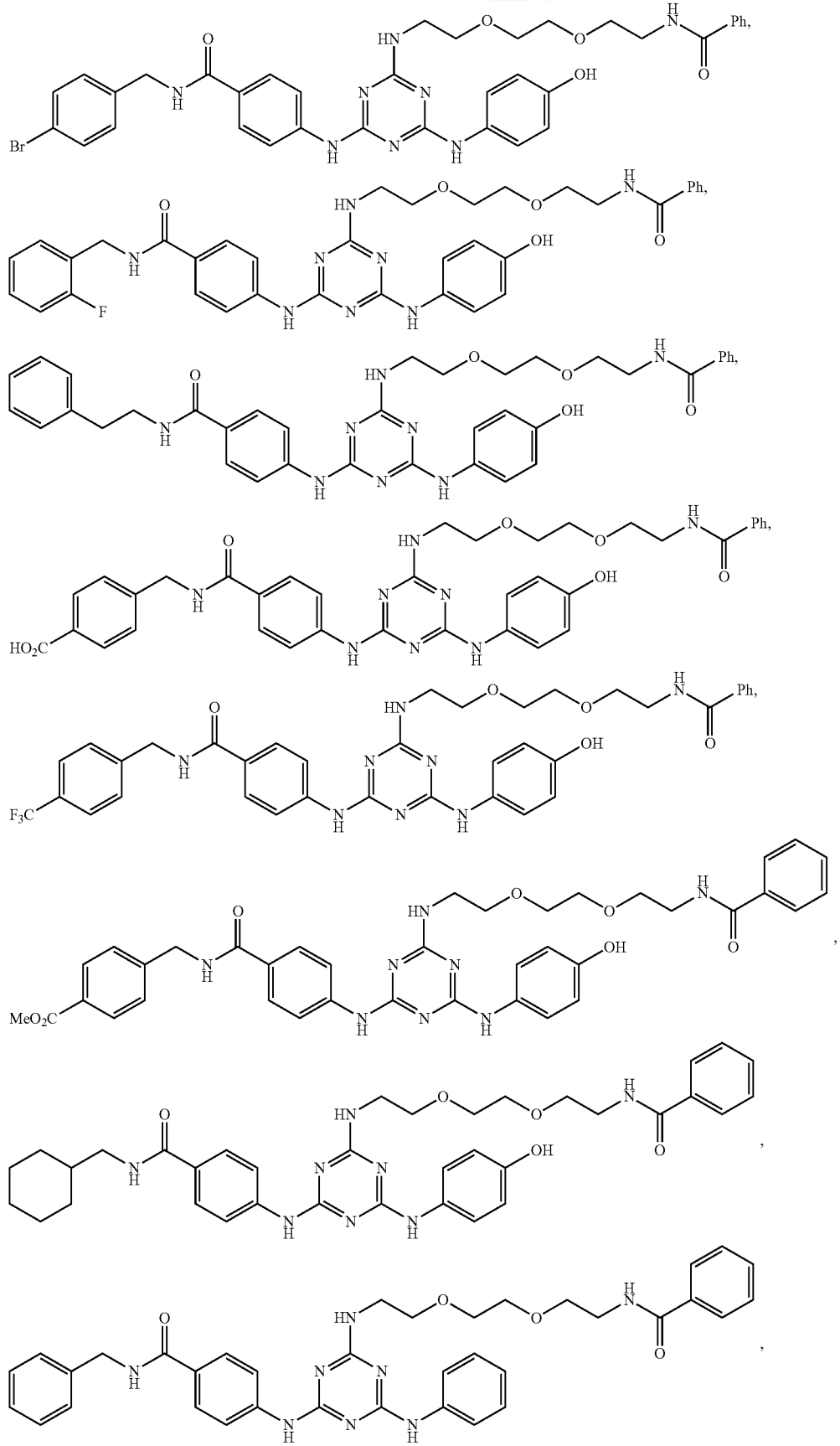

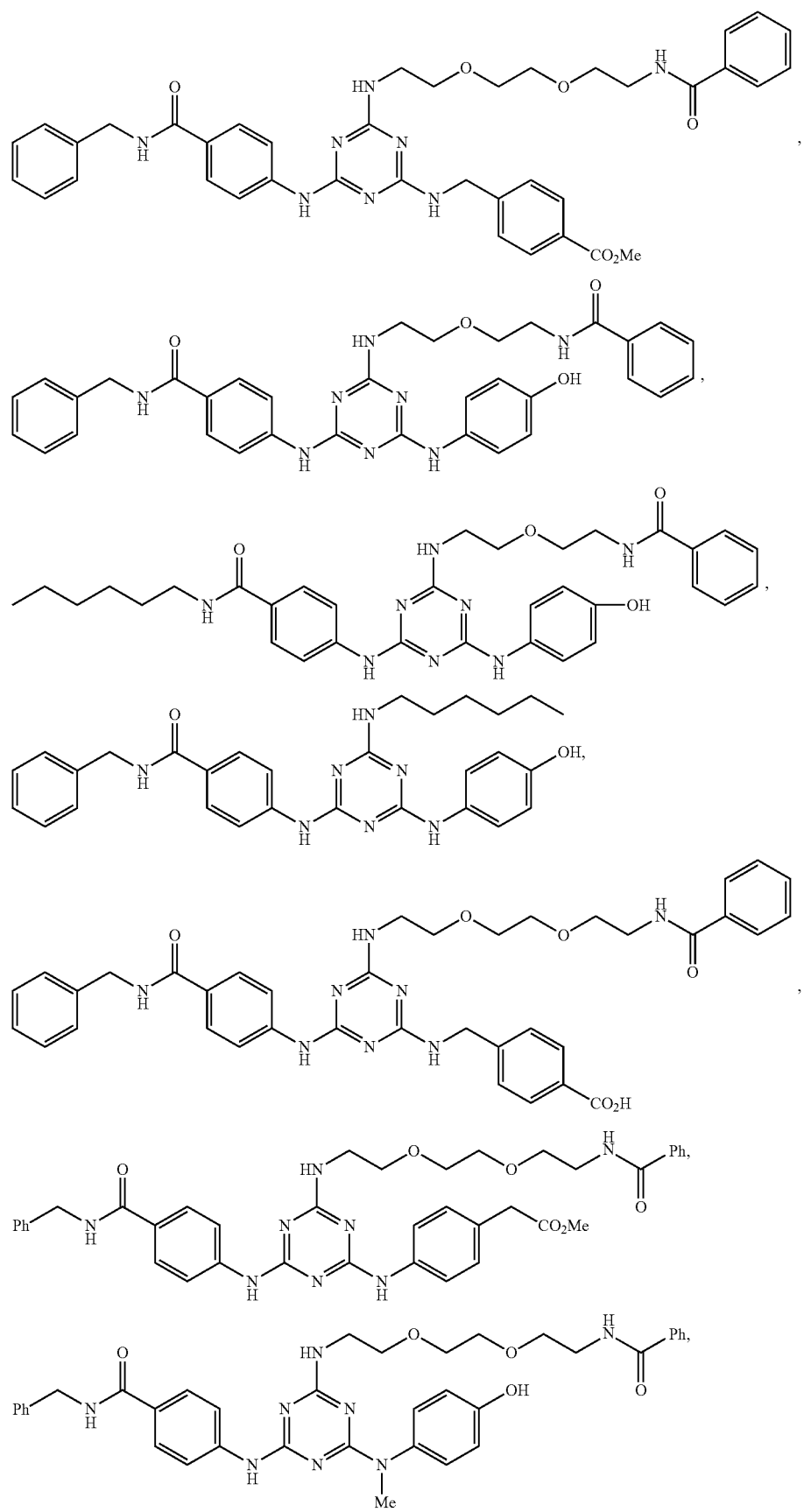

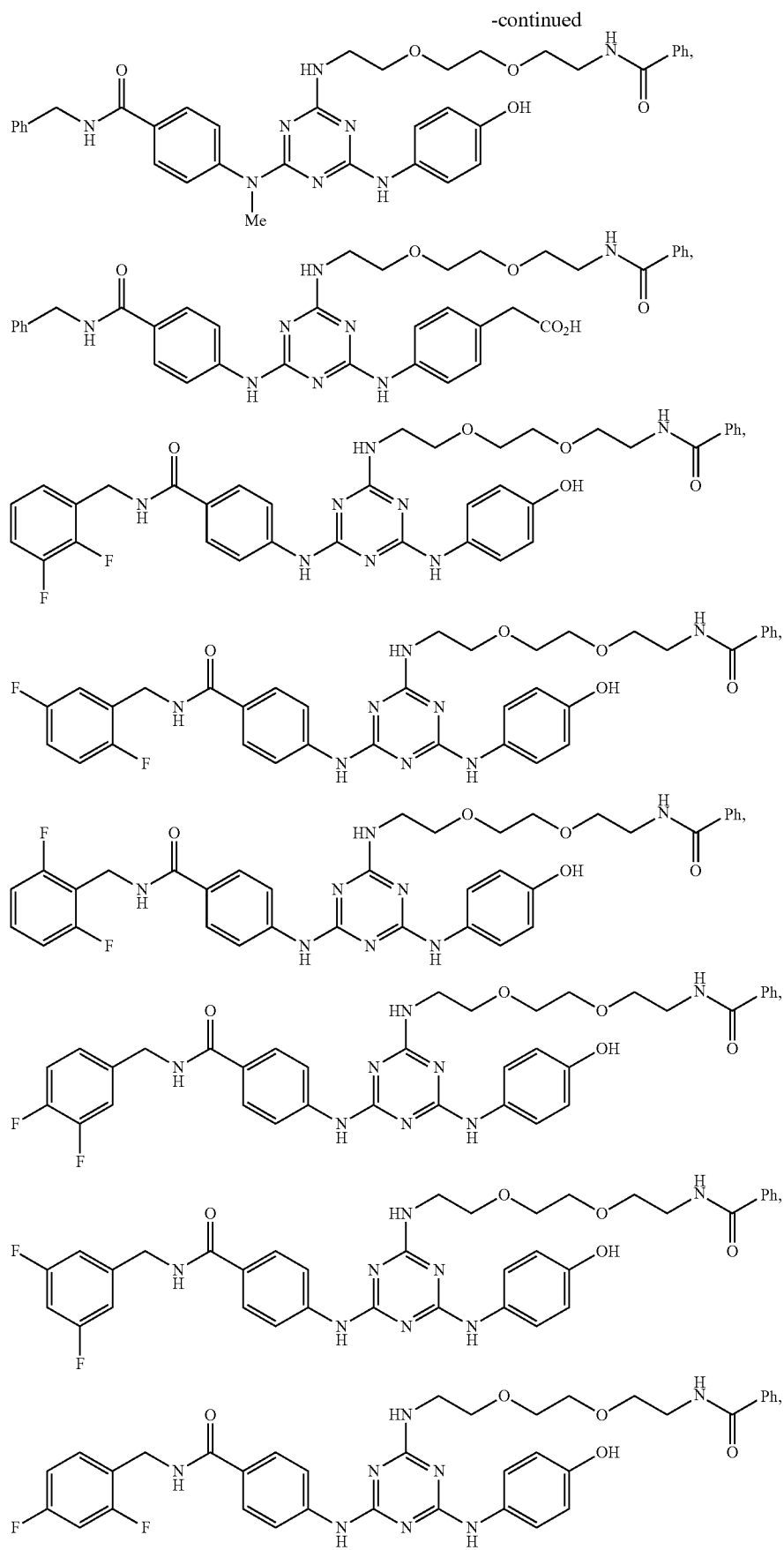

-continued
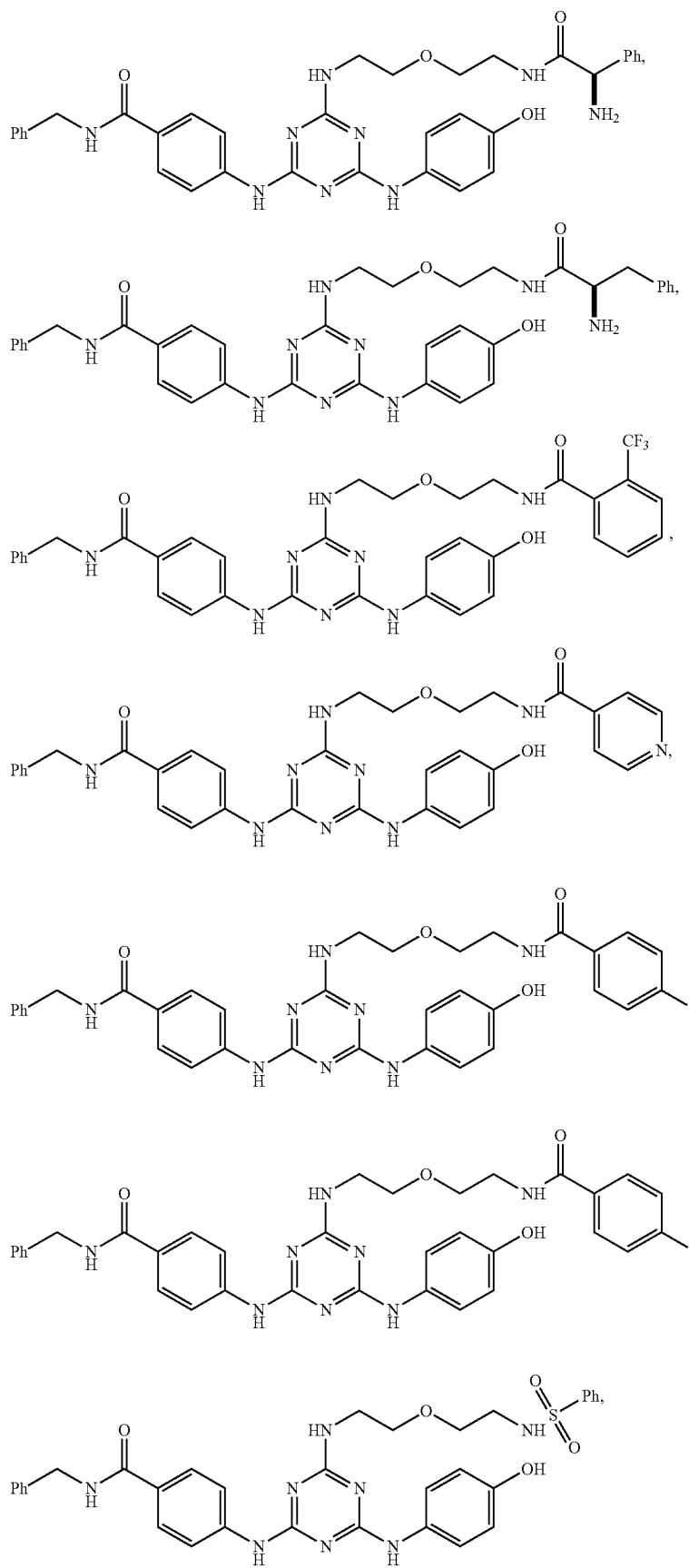

-continued
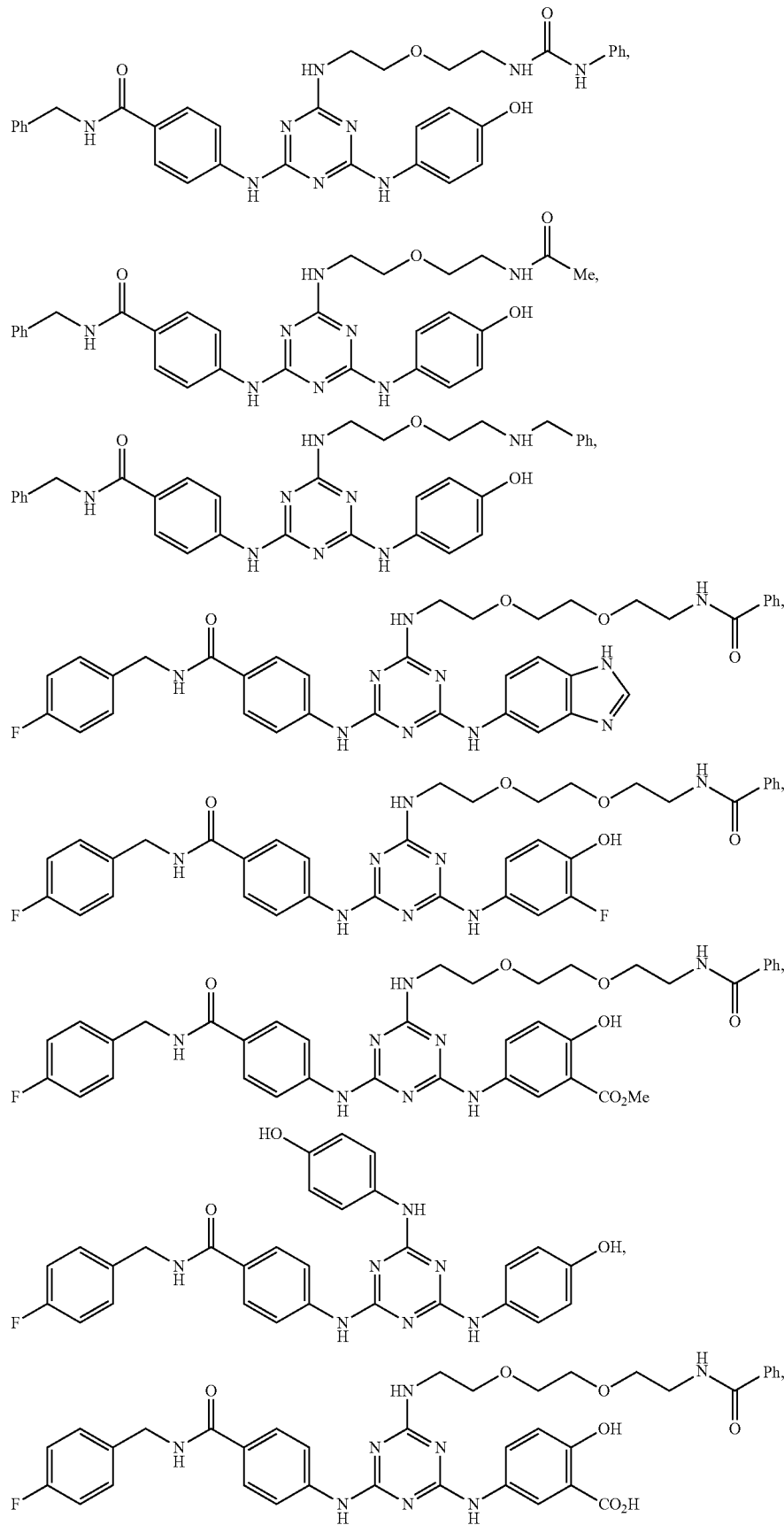

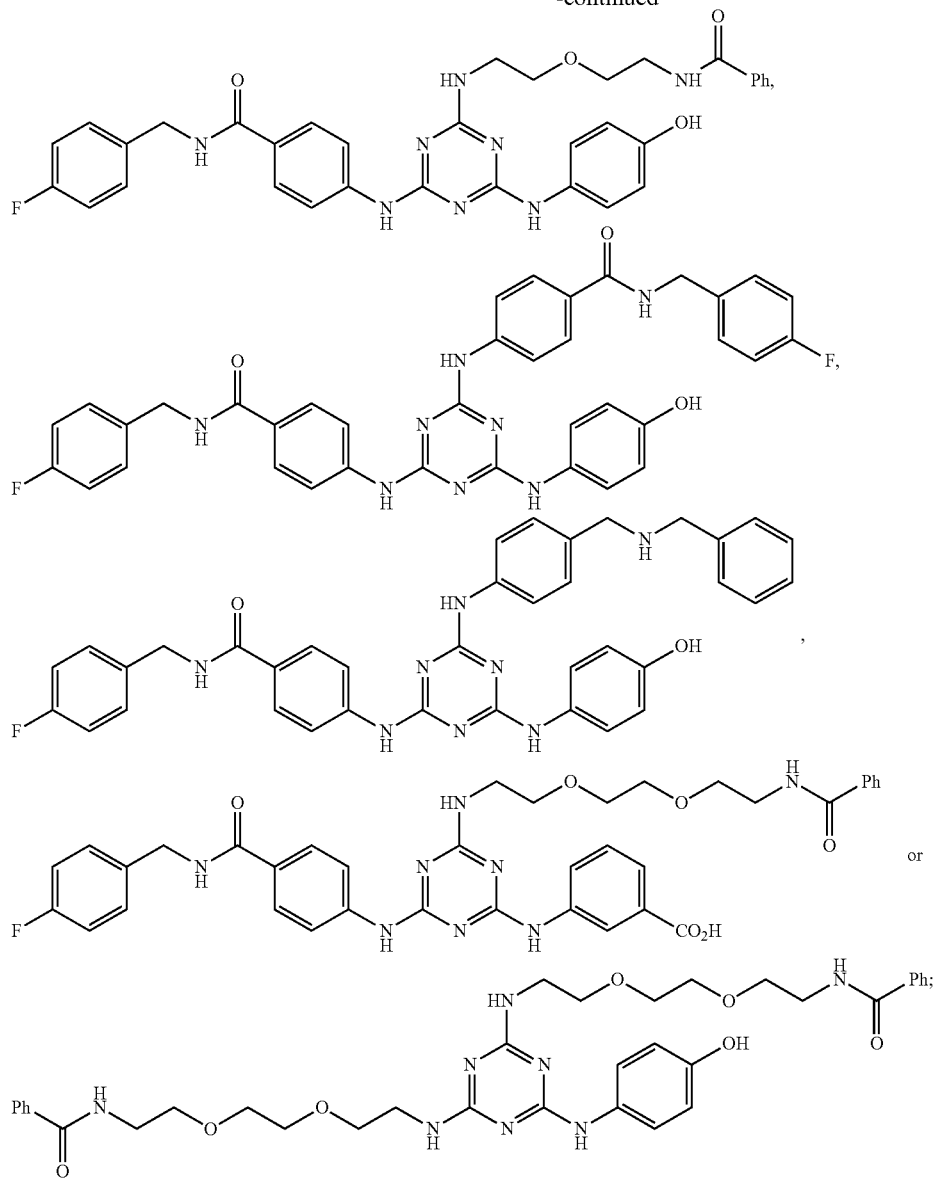
or a pharmaceutically acceptable salt thereof.
Preferred compounds include those having the structure:
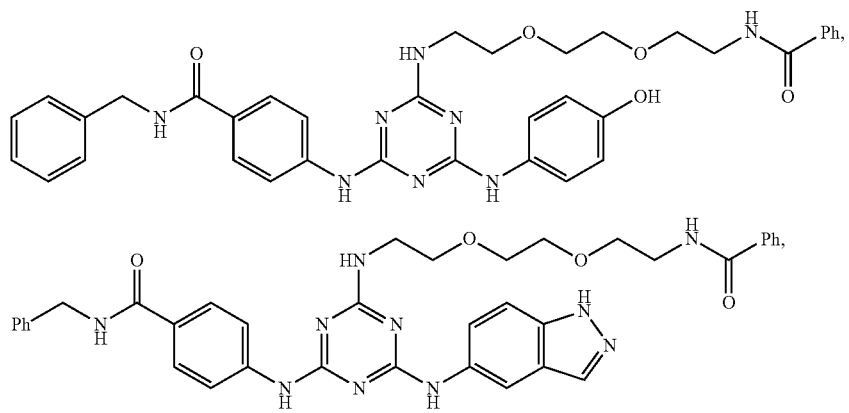

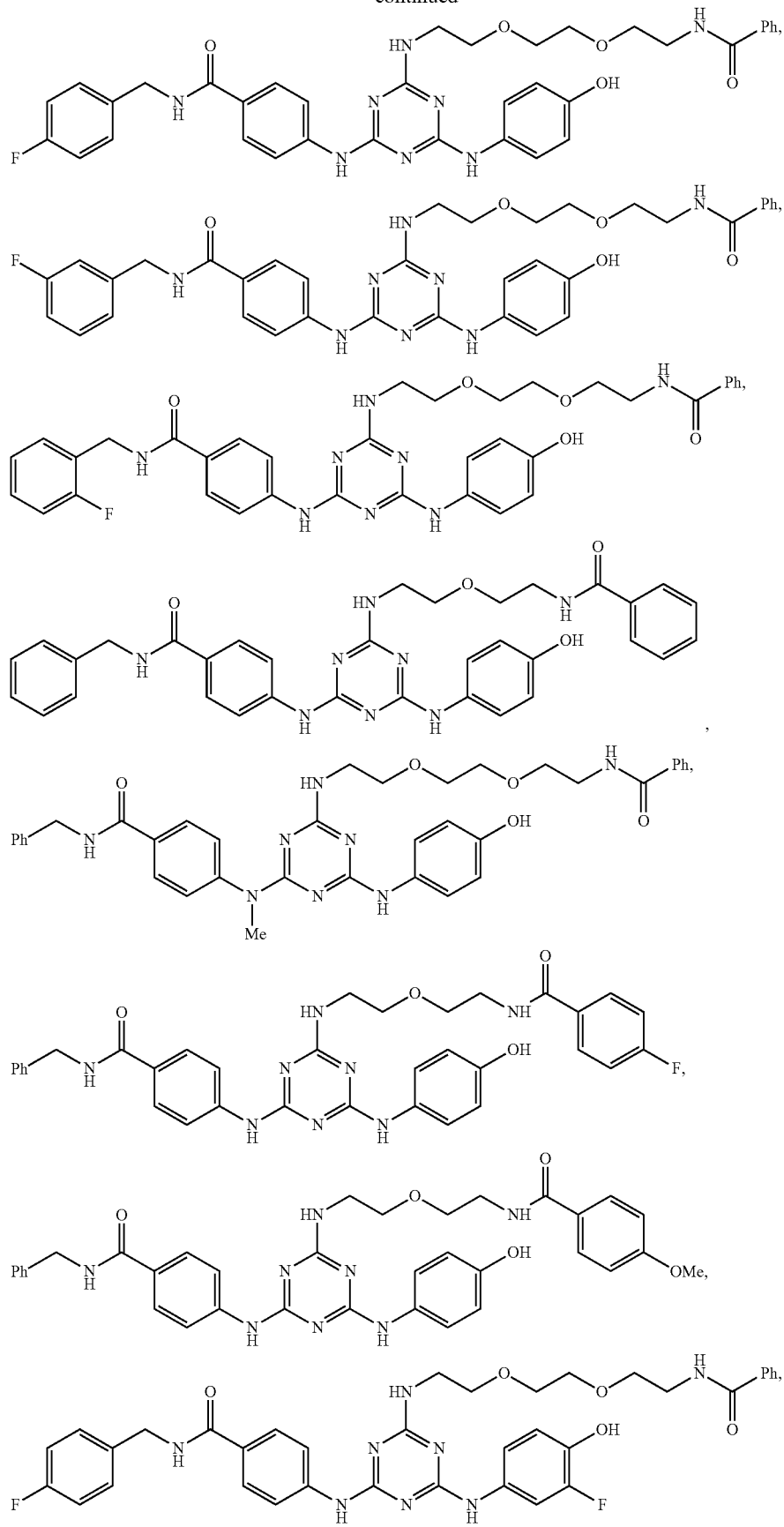

-continued

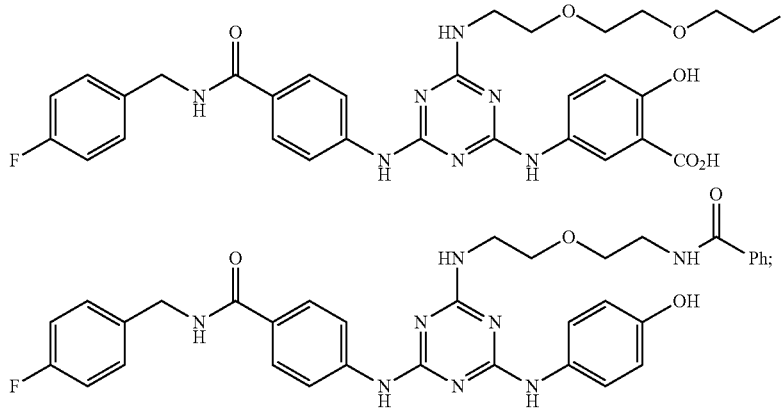

or a pharmaceutically acceptable salt thereof.

A most preferred compound has the structure:

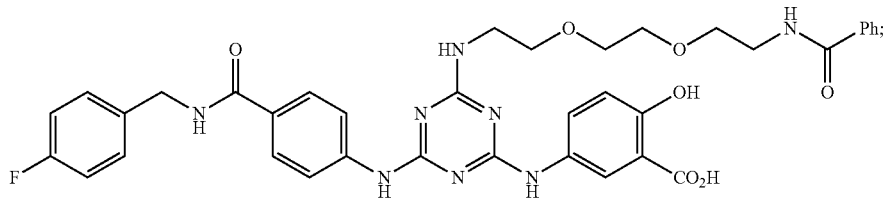 [SMILES: O=C(NCCOCCOCCNc1nc(Nc2ccc(C(=O)NCc3ccc(F)cc3)cc2)nc(Nc2ccc(O)c(C(=O)O)c2)n1)c1ccccc1]

or a pharmaceutically acceptable salt thereof.

The invention also provides a method of treating a condition selected from the group consisting of obesity and pulmonary arterial hypertension comprising administering to a subject having obesity and/or pulmonary arterial hypertension a prostaglandin transporter inhibitor in an amount effective to treat obesity and/or pulmonary arterial hypertension. PGT inhibitors include those described herein as well as, for example, in Chi et al., 2005; WO 2007/136638; US 2012/0238577.

The invention further provides a pharmaceutical composition for treating obesity and/or pulmonary arterial hypertension comprising a compound of formula (I) in an amount effective to treat obesity and/or pulmonary arterial hypertension and a pharmaceutically acceptable carrier.

The invention also provides a pharmaceutical composition for treating obesity and/or pulmonary arterial hypertension comprising a prostaglandin transporter inhibitor in an amount effective to treat obesity and/or pulmonary arterial hypertension and a pharmaceutically acceptable carrier.

By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The above-described compounds can be formulated without undue experimentation for administration to a mammal, including humans, as appropriate for the particular application. Additionally, proper dosages of the compositions can be determined without undue experimentation using standard dose-response protocols.

Accordingly, compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like. Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

Topical administration may be preferred for localized application of the compound, for example, for promoting wound healing or for ocular administration (e.g., eye drops).

The present invention includes nasally administering to the mammal a therapeutically effective amount of the compound, for example, as a nasal spray, nasal drop, suspension, gel, ointment, cream powder, or using a nasal tampon or nasal sponge.

Where the compound is administered peripherally such that it must cross the blood-brain barrier, the compound is preferably formulated in a pharmaceutical composition that enhances the ability of the compound to cross the blood-brain barrier of the mammal. Such formulations are known in the art and include lipophilic compounds to promote absorption. Uptake of non-lipophilic compounds can be enhanced by combination with a lipophilic substance. Lipophilic substances that can enhance delivery of the compound across the nasal mucus include but are not limited to fatty acids (e.g., palmitic acid), gangliosides (e.g., GM-1), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™ X-100, and sodium tauro-24,25-dihydrofusidate (STDHF).

In particular embodiments of the invention, the compound is combined with micelles comprised of lipophilic substances. Alternatively, the compound can be combined with liposomes (lipid vesicles) to enhance absorption. The compound can be contained or dissolved within the liposome and/or associated with its surface. Suitable liposomes include phospholipids (e.g., phosphatidylserine) and/or gangliosides (e.g., GM-1). Bile salts and their derivatives and detergent-like substances can also be included in the liposome formulation.

The invention also provides for the use of any of the compounds of formula (I) for treating obesity and/or pulmonary arterial hypertension in a subject.

As used herein, a person is considered obese when their body mass index (BMI), as obtained by dividing the person's weight in kilograms by the square of the person's height in meters, exceeds 30 kg/m$^2$.

Preferably, the compound or prostaglandin transporter inhibitor is administered to a subject in an amount that is effective to reverse, in whole or in part, changes in gene expression associated with pulmonary arterial hypertension, in particular changes in gene expression observed in the lung.

The present invention is illustrated in the following Experimental Details section, which is set forth to aid in the understanding of the invention, and should not be construed to limit in any way the scope of the invention as defined in the claims that follow thereafter.

Experimental Details

A. Preparation of Chemical Compounds

Compounds were made according to one of 11 generic schemes described in U.S. Patent Application Publication No. US 2012/0238577, the contents of which are herein incorporated by reference. As an example, one of the schemes is reproduced herein below from US 2012/0238577. A specific example with a corresponding experimental description is given. Other compounds made via that same scheme are listed in tabular form beneath the experimental description. Compounds were synthesized at Provid Pharmaceuticals, Inc., North Brunswick N.J.

General Procedures.

HPLC was performed on Rainin SD-300 or Varian ProStar equipped with a single wavelength UV detector at 214 nm and linear gradients. Analytical HPLC was performed on a Varian $C_{18}$ column (microsorb 60-8, 4.6×250 mm) at a flow rate of 1 mL/min. Semi-preparative HPLC was performed on a Varian $C_{18}$ column (microsorb 60-8, 10.0×250 mm) at a flow rate of 5 mL/min. Preparative HPLC was routinely performed on a Varian $C_{18}$ column (microsorb 60-8, 21.4×250 mm) at a flow rate of 20 mL/min. The solvent system used on linear gradients was water with 0.075% TFA (solvent A) vs Acetonitrile with 0.075% TFA (solvent B). Silica gel used in flash column chromatography was obtained from Sorbent Technologies (Atlanta, Ga.). LC-MS spectra were taken on Waters ZQ LC/MS-ESI or APCI.

Generic Scheme:

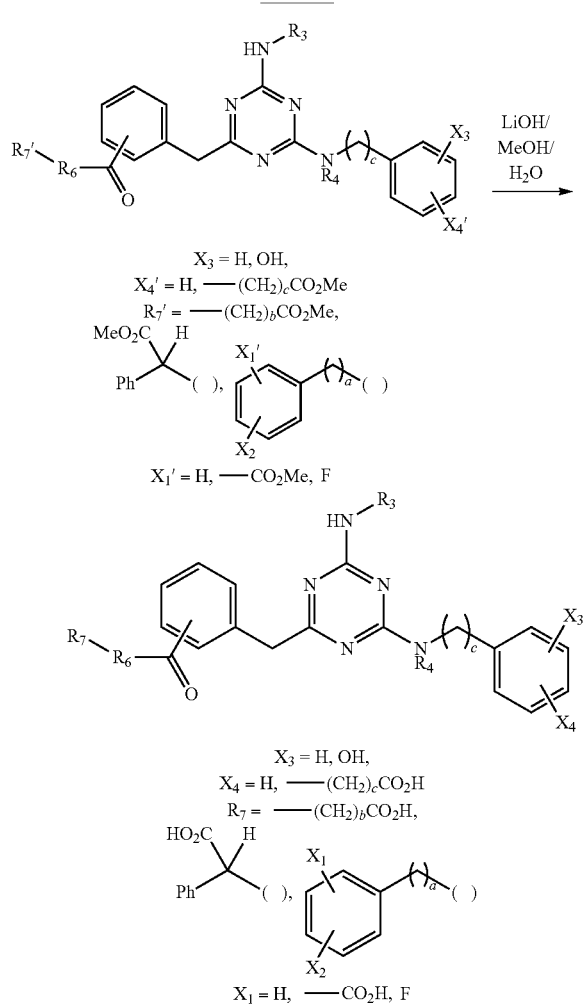

Experimental:

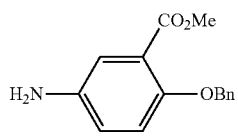

Preparation of aniline 9: To a solution of methyl 5-amino salicylate (1.0 eq.), in MeOH (10 mL) was added $Boc_2O$ (1.1 eqs.) followed by TEA (1.1 eqs.). The reaction mixture was allowed to stir for 1 hour. Subsequently, imidazole (0.5 eqs.) was added and the reaction mixture stirred for 10 mins at ambient temperature. The reaction mixture was concentrated in vacuo and the residue partitioned between $CH_2Cl_2$ and water. The layers were separated and the aqueous extracted with $CH_2Cl_2$ (3×). The combined organics were then washed with 0.1 M HCl (1×, aqueous), dried over $Na_2SO_4$, filtered and concentrated in vacuo. The residue was used without further purification.

To a solution of the residue (1.0 eq.) in DMF (10 mL) was added $K_2CO_3$ (1.2 eqs.) followed by BnBr (1.1 eqs.). The reaction mixture was heated to 60° C. and stirred overnight. The reaction mixture was concentrated in vacuo and the residue partitioned between $CH_2Cl_2$ and water. The layers were separated and the aqueous extracted with $CH_2Cl_2$ (3×). The combined organics were dried over $Na_2SO_4$, filtered and concentrated in vacuo. The residue was used without further purification.

The residue was dissolved EtOAc (3 mL) and concentrated HCl (3 mL) was added. The reaction mixture was stirred for 1 hour at ambient temperature before the reaction mixture was concentrated in vacuo. The residue was used without further purification.

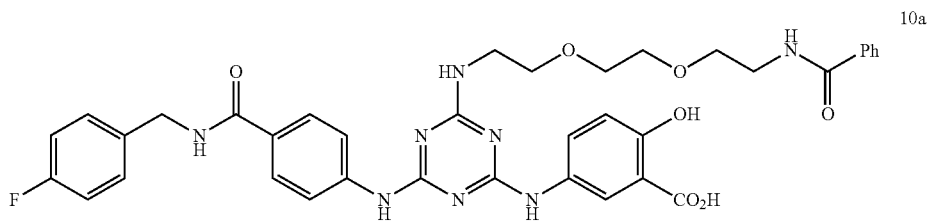 [SMILES: O=C(NCCOCCOCCNc1nc(Nc2ccc(C(=O)NCc3ccc(F)cc3)cc2)nc(Nc2ccc(O)c(C(=O)O)c2)n1)c1ccccc1]

To a solution of cyanuric chloride (1.14 eqs.) and ᵗbutyl 4-aminobenzoate (1.0 eq.) in THF (81 mL) was added ⁱPr₂NEt (1.1 eqs.). The reaction mixture was stirred at ambient temperature for 1 hour. The reaction mixture was partitioned between water and EtOAc. The aqueous layer was extracted with EtOAc (3×), and the combined organics were dried over Na₂SO₄, filtered and concentrated in vacuo. The residue was used without further purification.

To a solution of the residue (1.0 eq.) and aniline 9 (1.1 eqs.) in THF (52 mL) was added ⁱPr₂NEt (3.0 eqs). The reaction mixture was warmed to 50° C. and stirred overnight. The reaction mixture was cooled to ambient temperature and partitioned between water and EtOAc. The aqueous layer was extracted with EtOAc (3×), and the combined organics were dried over Na₂SO₄, filtered and concentrated in vacuo. The residue was used without further purification.

To a solution of the residue (1.0 eq.) and amine 1 (1.2 eqs.) in THF (1.5 mL) was added ⁱPr₂NEt (3.0 eqs.). The reaction mixture was warmed to 65° C. and stirred overnight. The reaction mixture was concentrated in vacuo and the residue was purified via column chromatography over silica gel (2:1/hexanes:EtOAc→98:2/CH₂Cl₂:MeOH). The obtained residue (0.116 g, 78% yield over 3 steps) was used without further purification.

The residue (1.0 eq.) was dissolved in TFA (1.0 mL) and DMS (1.0 mL). The reaction mixture was warmed to 50° C. and stirred overnight. The reaction mixture was concentrated in vacuo and the residue used without further purification.

To a mixture of the residue (1.0 eq.), 4-fluorobenzylamine (1.1 eqs.), EDAC.HCl (1.2 eqs.) and anhydrous HOBT (1.2 eqs.) was added DMF (1 mL). Subsequently, ⁱPr₂NEt (3.0 eqs.) was added to the reaction mixture and the resulting solution stirred overnight. The reaction mixture was then concentrated in vacuo and the residue purified via reverse phase HPLC to yield triazine 8iii (25.0 mg, 18% yield over 2 steps).

A heterogeneous mixture of triazine 8iii (1.0 eq.) and LiOH (30 eq.) in THF (0.3 mL), MeOH (0.3 mL) and H₂O (0.3 mL) was stirred at ambient temperature overnight. The reaction mixture was then concentrated in vacuo and the residue purified via reverse phase HPLC to yield triazine 10a (13.0 mg, 59% yield):MS (ESI): m/z=725 (M+H)⁺; analytical HPLC (10-90% MeCN in H₂O, 20 mins, flow rate=1.0 mL/min.) R$_f$=14.91 mins (>96% pure).

The following compounds were or could be made by the procedure described for triazine 10a:

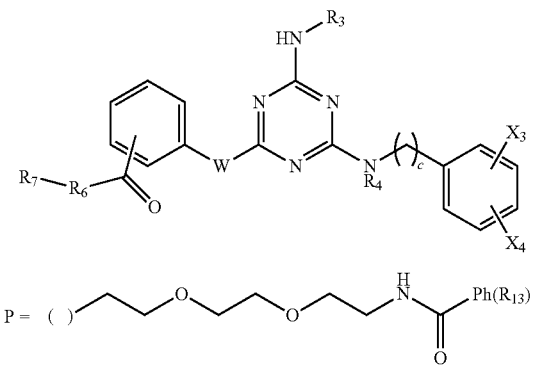

| Compound | W | X3 | X4 | C | R3 | R4 | R6 | R7 | (M + H)⁺ |
|---|---|---|---|---|---|---|---|---|---|
| 10b | NH | OH | H | 0 | P | H | NH | CO₂H(CH₂)₆— | 701 |
| 10c | NH | OH | H | 0 | P | H | NH | HO₂C—CH(Ph)—( ) | 707 |
| 10d | NH | OH | H | 0 | P | H | NH | HO₂C—CH(Ph)—( ) | 707 |
| 10e | NH | OH | H | 0 | P | H | NH | (4-HO₂C-C₆H₄)CH₂—( ) | 707 |
| 10f | NH | CO₂H | H | 1 | P | H | NH | Bn— | 705 |
| 10g | NH | CH₂CO₂H | H | 0 | P | H | NH | Bn— | 705 |
| 10h | NH | CO₂H | H | 0 | P | H | NH | (4-F-C₆H₄)CH₂—( ) | 709 |

B. Inhibitory Properties of Compounds

Inhibitory properties of the compounds were described in U.S. Patent Application Publication No. US 2012/0238577. The results are reproduced herein below from US 2012/0238577.

MDCK cells stably transfected with rat PGT (Endo et al., 2002) were seeded at 15-20% confluence on 24-well plates. The day on which the cells were seeded was considered day 1. $PGE_2$ uptake experiments were conducted on day 4. All of the $PGE_2$ uptake experiments were conducted at room temperature. On day 4, cells were washed twice with Waymouth buffer (135 mM NaCl, 13 mM H-Hepes, 13 mM Na-Hepes, 2.5 mM $CaCl_2$, 1.2 mM $MgCl_2$, 0.8 mM $MgSO_4$, 5 mM KCl, and 28 mM D-glucose). Then 200 µL of Waymouth buffer containing [$^3$H]$PGE_2$ (purchased from Perkin Elmer) was added to each well. At the designed time, the uptake of [$^3$H]$PGE_2$ was stopped by aspiration of uptake buffer; this was followed by immediate washing twice with 500 µL of chilled Waymouth buffer. Cells were then lysed with 100 µL lysis buffer containing 0.25% SDS and 0.05 N NaOH. 1.5 mL of scintillation solution was added to each well, and intracellular [$^3$H]$PGE_2$ was counted by MicroBeta Counter.

For preliminary testing of the compounds, 20 µL of Waymouth buffer containing the compound was added to each well; this was immediately followed by the addition of 180 L of Waymouth buffer containing [$^3$H]$PGE_2$. In each well, the total volume of uptake medium was 200 µL. Organic compounds were first dissolved in EtOH and then diluted in Waymouth buffer. The percent inhibition of [$^3$H]$PGE_2$ uptake by compounds was calculated as [(uptake$_{vehicle}$−uptake$_{inhibitor}$)÷(uptake$_{vehicle}$)]×100.

To determine IC50 of each compound, 20 µL of Waymouth buffer containing various concentrations of the compound was added to each well; this was immediately followed by the addition of 180 µL of Waymouth buffer containing [$^3$H]$PGE_2$. IC50 was calculated by fitting an equation of y=m1−m1*(m0/(m2+m0)).

Results for the compounds are presented in Table 1, Inhibitory Activities of PGT Inhibitors. Abbreviations: Bn=benzyl (—$CH_2$Ph), Bz=benzoyl (—(C=O)Ph), Me=methyl (—$CH_3$), Ph=phenyl.

TABLE 1

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| T26A | 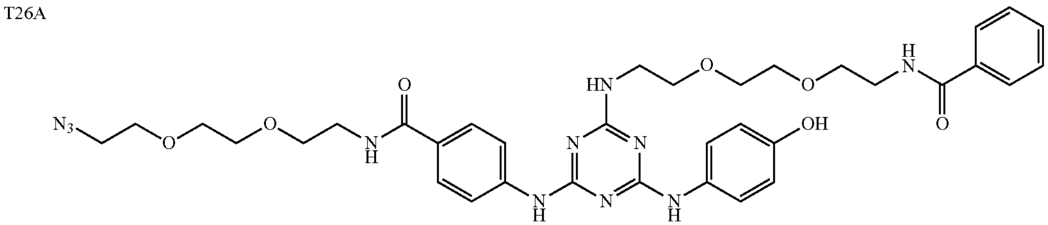 | | 378 | | 72.65 | | | | |
| 1 | 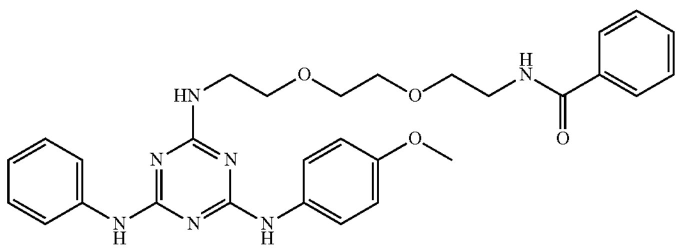 [SMILES: COc1ccc(Nc2nc(NCCOCCOCCNC(=O)c3ccccc3)nc(Nc3ccccc3)n2)cc1] | 543.62 | | | 9.6 | | | 8.5 | |
| 2 | 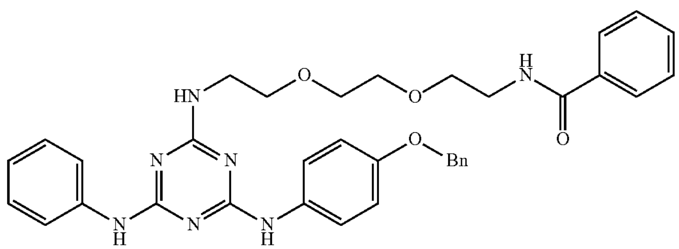 [SMILES: O=C(NCCOCCOCCNc1nc(Nc2ccccc2)nc(Nc2ccc(OCc3ccccc3)cc2)n1)c1ccccc1] | 619.71 | | | 1.6 | | | 6.5 | |

TABLE 1-continued

| | Structure | MW | | | |
|---|---|---|---|---|---|
| 3 | (structure) | 563.05 | 0.4 | | 1.7 |
| 4 | (structure) | 529.59 | 4850 | 7.0 | 32.4 | 67.6 | 81.5 |
| 5 | (structure) | 571.67 | | 6.6 | | 9.6 |
| 6 | (structure) | 587.67 | | 3.6 | | 11.7 |

TABLE 1-continued
| | | | | |
|---|---|---|---|---|
| 7 | 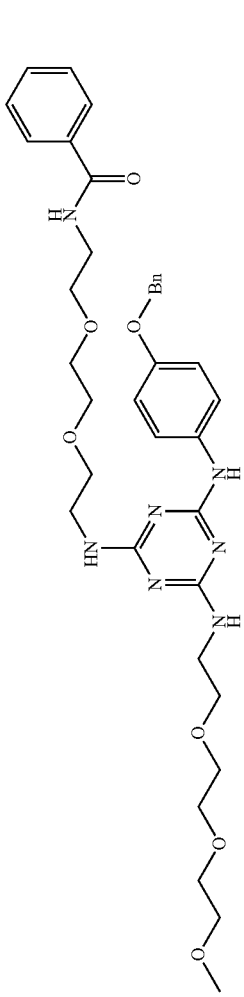 | 689.80 | 4.8 | 22.5 |
| 8 | 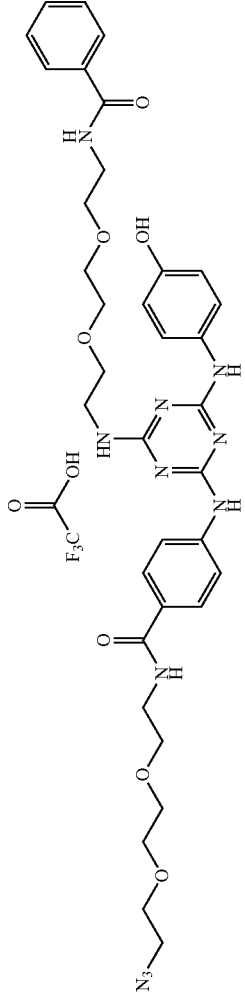 | 843.81 | 223.8 | 52.3 |
| 9 | 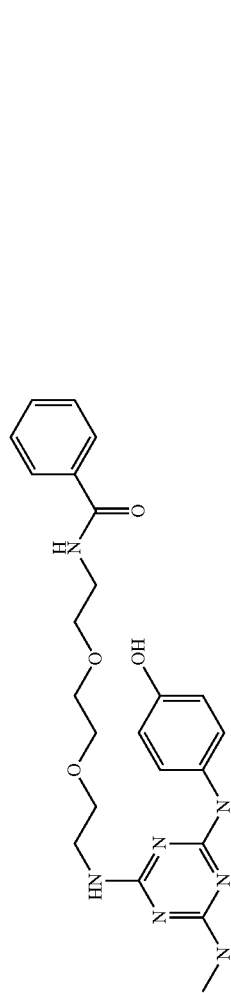 | 481.55 | 1.3 | 18.8 |
| 10 | 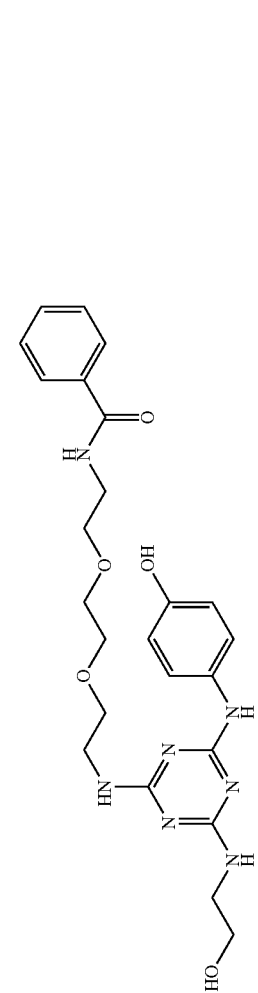 | 497.55 | 1.4 | 15.0 |

TABLE 1-continued
| | | | |
|---|---|---|---|
| 11 | 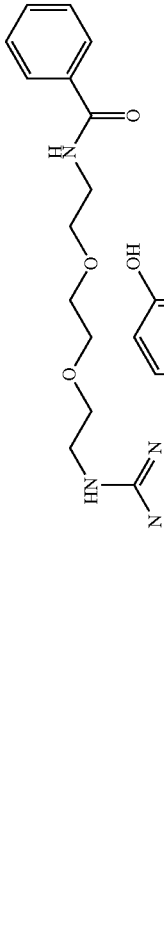 | 599.68 | 11.4 | 29.9 |
| 12 | 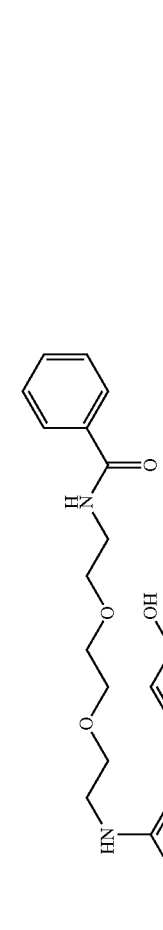 | 568.05 | 2.8 | 4.7 |
| 13 | 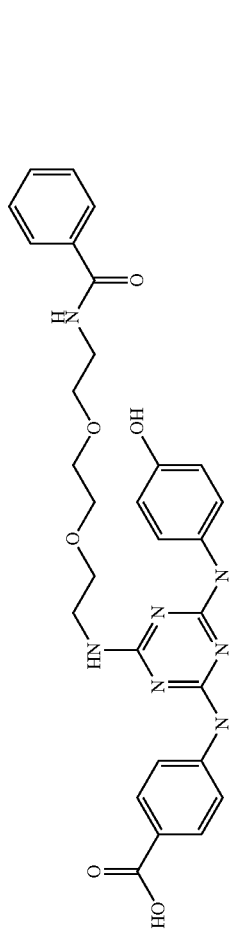 | 687.62 | 19.2 | 19.3 |
| 14 | 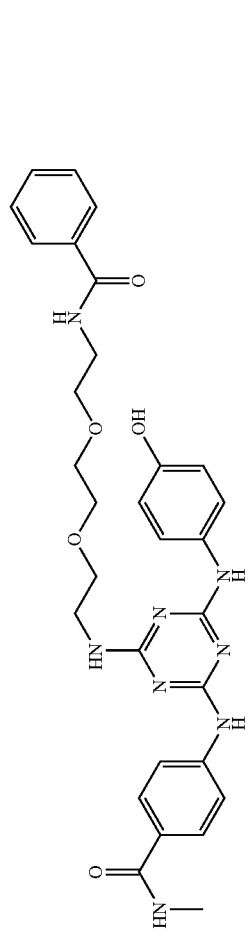 | 700.66 | 10.6 | 35.9 |

TABLE 1-continued

| | Structure | MW | A | B |
|---|---|---|---|---|
| 15 | | 714.69 | 15.0 | 16.6 |
| 16 | | 742.74 9770 | 11.8 | 44.8 |
| 17 | | 701.65 6570 | 22.0 | 55.6 |
| 18 | | 774.74 | 21.1 | 48.9 |

TABLE 1-continued

| # | Structure | MW | | |
|---|---|---|---|---|
| 19 | | 832.82 | 41.3 | 75.0 |
| 20 | | 686.63 | 9.6 | 14.4 |
| 21 | | 730.69 | 15.7 | 68.2 |
| 22 | | 776.76 | 42.7 | 62.4 | 88.1 | 95.5 |
| 23 | | 673.64 | 14.4 | 38.4 |

TABLE 1-continued

| | Structure | MW | | |
|---|---|---|---|---|
| 24 | (structure) | 728.71 | 1.7 | 9.2 |
| 25 | (structure) | 658.62 | 12.9 | 27.7 |
| 26 | (structure) | 673.64 | 2.6 | 35.2 |
| 27 | (structure) | 649.66 | 28.2 | 53.8 |
| 28 | (structure) | 659.61 | 2.4 | 56.5 |

TABLE 1-continued

| # | Structure | | | |
|---|---|---|---|---|
| 29 | (pyridyl amide derivative) | 758.62 | 15.9 | 49.6 |
| 30 | (4-F phenyl amide derivative) | 661.6 | 26.1 | 78.25 |
| 31 | (4-Br phenyl amide derivative) | 722.51 | 12.2 | 69.2 |
| 32 | (4-OMe phenyl amide derivative) | 673.64 | 29.0 | 71.0 |

TABLE 1-continued

| # | Structure | MW | Val1 | Val2 |
|---|---|---|---|---|
| 33 | pyridin-3-yl amide derivative | 758.62 | 13.2 | 54.6 |
| 34 | 3-fluorobenzamide derivative | 661.6 | 25.8 | 81 |
| 35 | 3,5-difluorobenzamide derivative | 679.59 | 20.4 | 75.6 |
| 36 | 3-bromobenzamide derivative | 722.51 | 30.3 | 81.1 |

TABLE 1-continued

| # | Structure | MW | | |
|---|---|---|---|---|
| 37 | (3-OMe-benzamide derivative) | 673.64 | 32.4 | 79.0 |
| 38 | (phenylsulfonamide derivative) | 679.66 | 22.8 | 63.0 |
| 39 | (thiophene-2-carboxamide derivative) | 649.64 | 42.9 | 86.2 |
| 40 | (4-Ph-benzamide derivative) | 719.71 | 16.3 | 46.9 |

TABLE 1-continued
| | Structure | MW | | | |
|---|---|---|---|---|---|
| 41 | 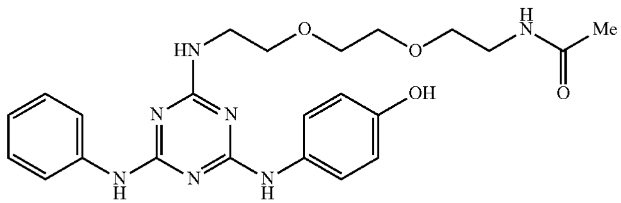 | 581.54 | | 0.3 | 6.6 |
| 42 | 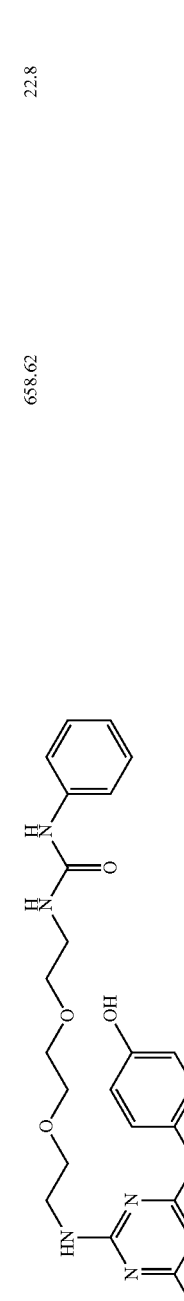 | 658.62 | | 22.8 | 57.6 |
| 43 | 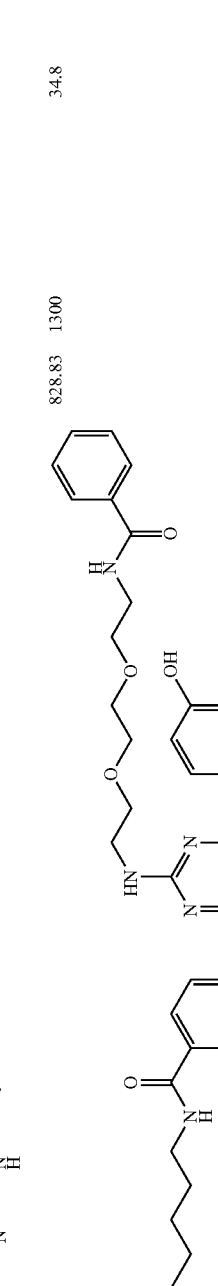 | 828.83 | 1300 | 34.8 | 84.1 |
| 44 | 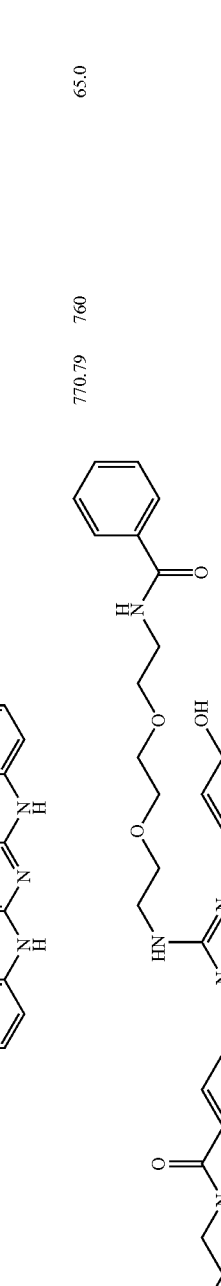 | 770.79 | 760 | 65.0 | 77.5 |
| 45 | 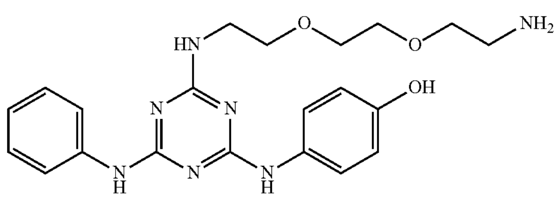 | 653.52 | | 5.0 | 12.9 |

TABLE 1-continued

| # | Structure | MW | A | B |
|---|---|---|---|---|
| 46 | 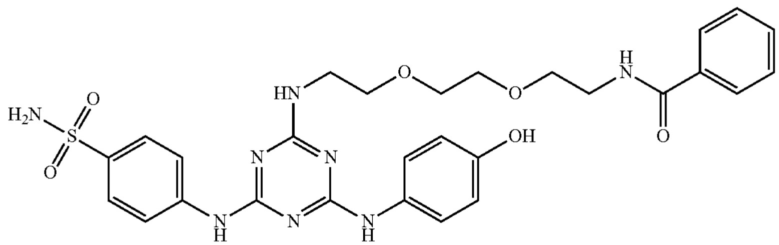 | 722.69 | 4.1 | 32.4 |
| 47 | 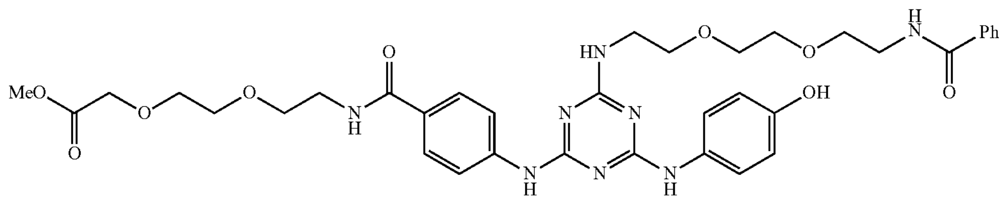 | 846.8 | 22.6 | 76.5 |
| 48 | 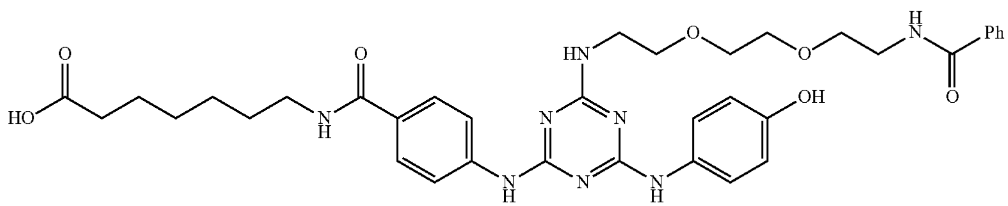 | 700.78 | 14.2 | 62.8 |
| 49 | 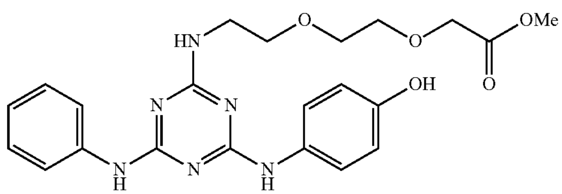 | 568.5 | 1.7 | 12.5 |

TABLE 1-continued

| # | Structure | MW | | | |
|---|---|---|---|---|---|
| 50 | (structure) | 550.53 | 9.3 | | 15.1 |
| 51 | (structure) | 440.45 | 17.4 | | 29.8 |
| 52 | (structure) | 422.48 | 0.1 | | 1.8 |
| 53 | (structure) | 667.63 | 4040 | 65.2 | 83.4 | 86.4 |

TABLE 1-continued

| # | Structure | MW | A | B |
|---|---|---|---|---|
| 54 | | 695.65 | 33.7 | 52.2 |
| 55 | | 492.49 | 12.7 | 26.1 |
| 56 | | 678.06 | 38.0 | 80.5 |
| 57 | | 571.63 | 27.4 | 29.5 |
| | | 5570 | | 56.6 |

TABLE 1-continued

| # | Structure | | | |
|---|---|---|---|---|
| 58 | (structure) | 557.6 | 16.25 | 41.0 | 52.5 |
| 59 | (structure) | 599.56 2460 | 36.8 | | 75.8 |
| 60 | (structure) | 699.67 | 7.2 | | 34.5 |
| 61 | (structure) | 685.65 | 7.5 | | 46.1 |
| 62 | (structure) | 611.61 | 20.4 | | 50.1 |

TABLE 1-continued

| | Structure | MW | | | |
|---|---|---|---|---|---|
| 63 | | 625.64 | 11.0 | | 44.1 |
| 64 | | 800.78 | 15.5 | 71.6 | 77.2 | 90.2 |
| 65 | | 794.82 | 18.4 | 66.4 | 84.0 | 90.0 |
| 66 | | 804.81 | 10.9 | | 64.4 | |
| 67 | | 891.77 | 13.4 | | 76.1 | |

TABLE 1-continued

| # | Structure | MW | | | |
|---|---|---|---|---|---|
| 68 | (structure) | 790.78 | 15.0 | | 70.8 |
| 69 | (structure) | 777.74 | 890 | 24.9 | 83.2 |
| 70 | (structure) | 891.77 | 1050 | 21.2 | 84.0 |
| 71 | (structure) | 891.77 | | 16.7 | 78.4 |
| 72 | (structure) | 711.61 | | 19.7 | 66.1 | 75.3 |

TABLE 1-continued

| # | Structure | MW | | | | |
|---|---|---|---|---|---|---|
| 73 | (structure) | 834.79 | | 45.0 | 51.6 | 38.9 | 75.3 |
| 74 | (structure) | 834.79 | | 56.9 | 82.0 | | |
| 75 | (structure) | 667.63 | | | 8.4 | 10.1 | 12.5 |
| 76 | (structure) | 769.81 | | 13.5 | 39.9 | 70.5 | |
| 77 | (structure) | 712.63 | | 1.8 | 4.3 | 23.2 | |

TABLE 1-continued

| # | Structure | MW | | | |
|---|---|---|---|---|---|
| 78 | (structure) | 776.76 | 15.5 | 24.5 | 83.2 |
| 79 | (structure) | 706.75 | 5.4 | 29.2 | 54.9 |
| 80 | (structure) | 706.75 | 0.7 | 21.8 | 57.2 |
| 81 | (structure) | 806.78 | 0.4 | 16.2 | 80.1 |
| 82 | (structure) | 844.76 | 2.1 | 5.0 | 47.6 |

TABLE 1-continued

| # | Structure | MW | a | b | c | d | e |
|---|---|---|---|---|---|---|---|
| 83 | | 777.74 | 609 | | 4.1 | 10.4 | 42.0 |
| 84 | | 583.56 | | | | | |
| 85 | | 597.58 | | | | 13.7 | 37.1 |
| 86 | | 806.78 | 870 | 50.0 | 70.7 | 81.4 | 86.4 |
| 87 | | 826.82 | 710 | 55.1 | 71.8 | 83.5 | 90.6 |

(Additional values visible: 5.7, 7.6, 12.2, 49.6)

TABLE 1-continued

| | Structure | | | | | |
|---|---|---|---|---|---|---|
| 88 | (triazine structure with MeO-phenyl benzyl amide) | 852.85 | 820 | 61.8 | 67.6 | 82.6 | 88.2 |
| 89 | (triazine structure with naphthyl benzyl amide) | 811.2 | | | 33.8 | 76.5 | 86.0 |
| 90 | (triazine structure with Ph-phenyl benzyl amide) | 806.78 | | | 23.4 | 60.6 | 72.7 |
| 91 | (triazine structure with Cl-phenyl benzyl amide) | 852.85 | 620 | 60.8 | 72.1 | 84.0 | 88.0 |
| 92 | (triazine structure with MeO-phenyl benzyl amide) | 815.79 | | | 33.7 | 71.3 | 80.6 |

TABLE 1-continued

| # | Structure | MW | | | | |
|---|---|---|---|---|---|---|
| 93 | (structure) | 806.78 | 24.6 | | 43.3 | 51.1 |
| 94 | (structure) | 826.82 | 36.0 | | 66.7 | 76.1 |
| 95 | (structure) | 668.62 | | 1.9 | 23.4 | 50.4 |
| 96 | (structure) | 611.61 | | 8.6 | 23.9 | 51.9 |
| 97 | (structure) | 625.64 | | 13.1 | 19.4 | 30.8 |

TABLE 1-continued

| | Structure | MW | | | | |
|---|---|---|---|---|---|---|
| 98 | (4-chlorobenzyl benzamide triazine phenol ether ethyl benzamide) | 767.15 | 23.7 | 41.1 | 6.7 | 24.9 | 75.1 |
| 99 | (4-fluorobenzyl benzamide triazine phenol Ph-CO-NH ether) | 794.75 | | 81.3 | 61.8 | 77.1 | 89.4 |
| 100 | (2,4-dichlorobenzyl benzamide triazine phenol Ph-CO-NH ether) | 845.65 | | 47.4 | 56.4 | 57.6 | 86.0 |
| 101 | (3-CF3-benzyl benzamide triazine phenol Ph-CO-NH ether) | 844.76 | | 47.4 | 54.0 | 71.0 | 91.4 |

TABLE 1-continued
| | | | | | |
|---|---|---|---|---|---|
| 102 | 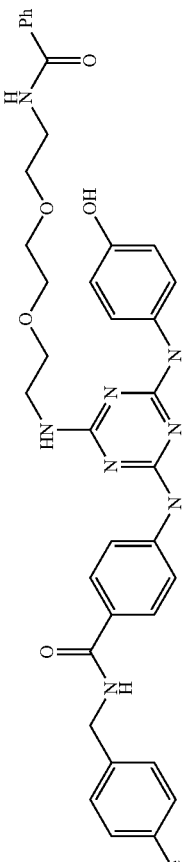 | 790.78 | | 41.9 | 65.7 | 88.0 |
| 103 | 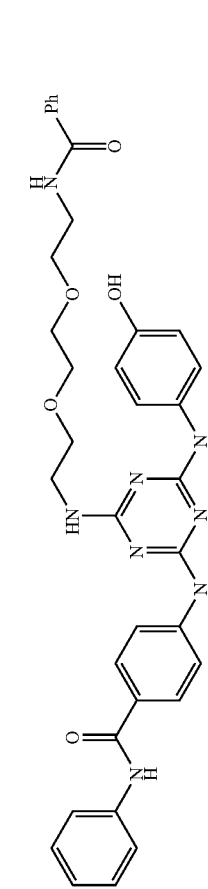 | 762.73 | | 38.3 | 62.2 | 83.7 |
| 104 | 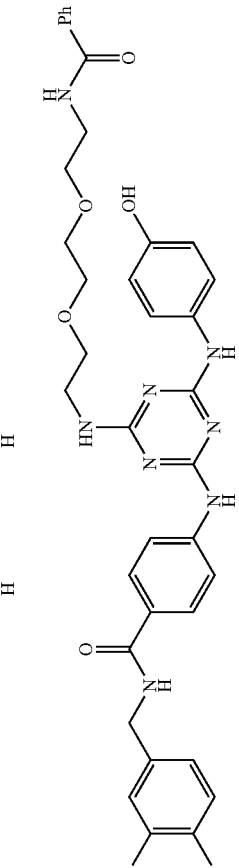 | 845.65 | 46.6 | 61.6 | 87.8 | 91.6 |
| 105 | 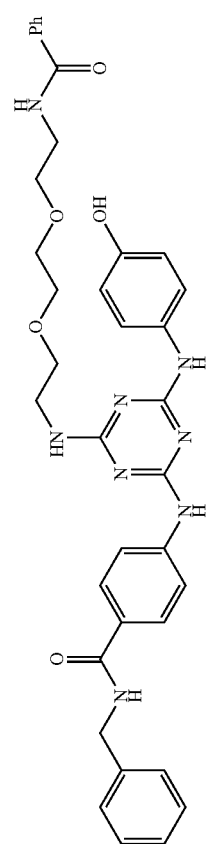 | 794.75 | 47.5 | 67.9 | 64.6 | 81 | 92.45 |
| 106 | 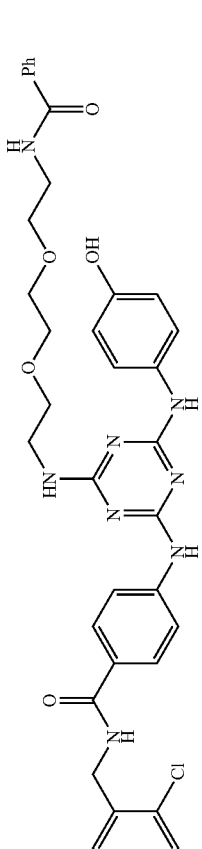 | 811.2 | | 68.4 | 64.8 | 68.8 | 93.1 |

TABLE 1-continued
| | | | | | | |
|---|---|---|---|---|---|---|
| 107 | 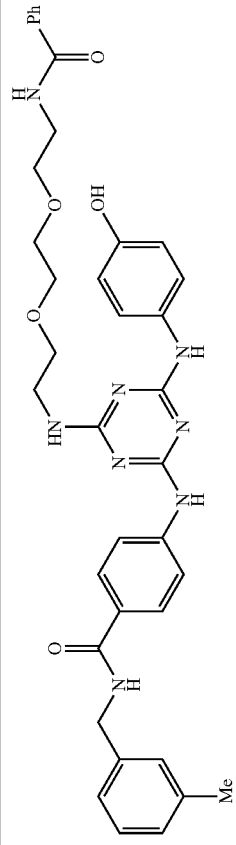 | 790.78 | 65.2 | 56.3 | 80.7 | 91.3 |
| 108 | 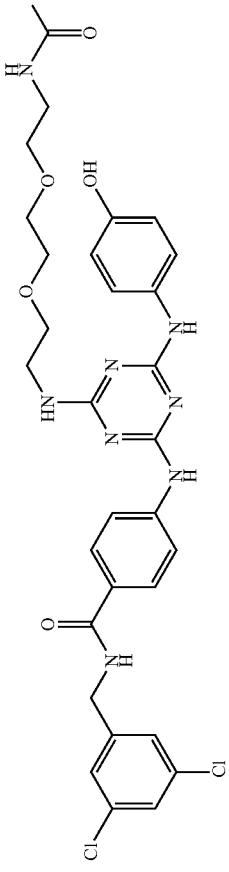 | 845.65 | 70.3 | 60.8 | 78.3 | 76.6 |
| 109 | 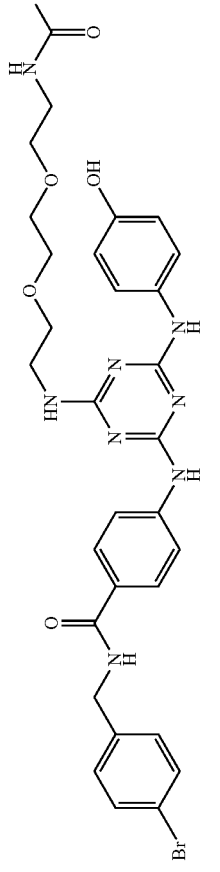 | 855.65 | 49.5 | 55.6 | 59.8 | 85.1 |
| 110 | 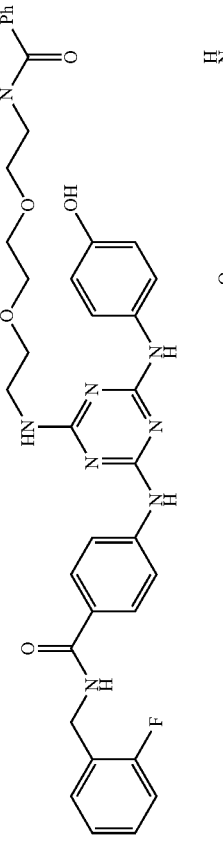 | 794.75 31.3 | 69.6 | 60.6 | 78.3 | 93.6 |
| 111 | 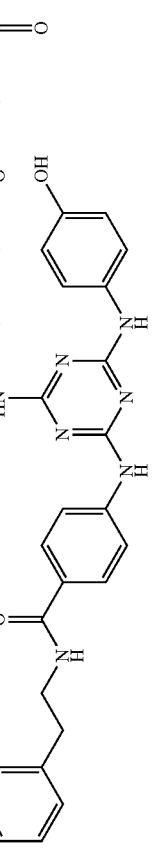 | 790.78 | 52.2 | 59.1 | 81.5 | 93.2 |

TABLE 1-continued

| | | | | | |
|---|---|---|---|---|---|
| 112 | [structure] | 706.75 | 36.8 | 17.5 | 32.2 | 49.4 |
| 113 | [structure] | 844.76 | 49.2 | 36.8 | 84.1 | 92.4 |
| 114 | [structure] | 834.79 | 41.0 | 61.4 | | |
| 115 | [structure] | 782.81 | 54.4 | 76.8 | | |

TABLE 1-continued

| | Structure | MW | | | |
|---|---|---|---|---|---|
| 116 | (structure) | 760.76 | 36.4 | 59.4 | |
| 117 | (structure) | 832.82 | 8.1 | 36.7 | |
| 118 | (structure) | 732.7 | 20.9 | 74.2 | 90.7 |
| 119 | (structure) | 726.74 | 57.2 | 81.4 | |

TABLE 1-continued

| # | Structure | MW | A | B |
|---|---|---|---|---|
| 120 | 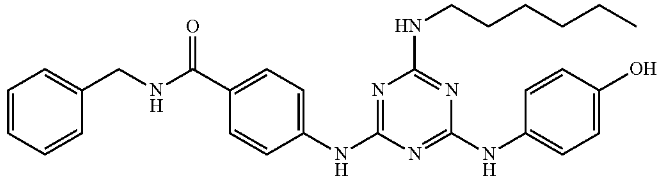 | 625.64 | 11.2 | 29.1 |
| 121 | 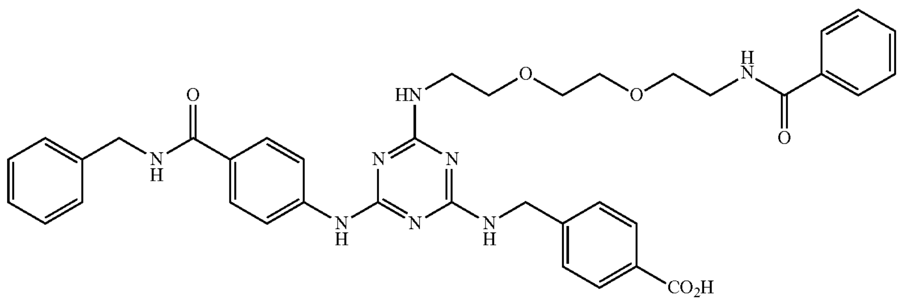 | 704.77 | 1.0 | 28.8 |
| 122 | 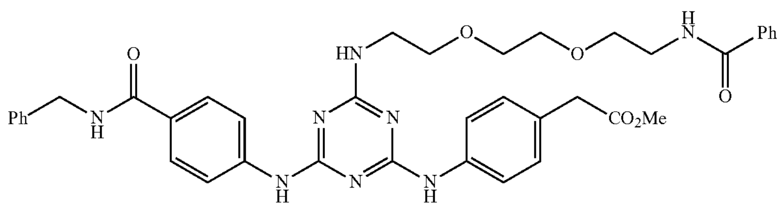 | 832.82 | 5.8 | 38.1 |
| 123 | 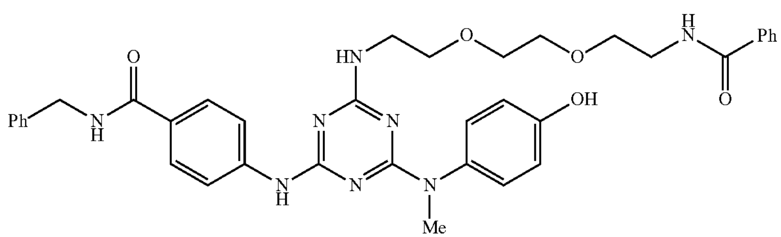 | 790.78 | 12.0 | 36.6 |

TABLE 1-continued

| | Structure | MW | a | b | c |
|---|---|---|---|---|---|
| 124 | | 790.78 | 34 | 68.8 | 85.4 |
| 125 | | 704.77 | 3.2 | 24.3 | |
| 126 | | 812.74 | 24.0 | 56.3 | 70.0 |
| 127 | | 812.74 | 17.0 | 52.3 | 70.2 |
| 128 | | 812.74 | 36.6 | 71.8 | 82.2 |

TABLE 1-continued

| Cpd ID | Structure | Mol. Weight | IC$_{50}$ (nM) | Inh (% of Ctl) 0.01 μM | Inh (% of Ctl) 0.05 μM | Inh (% of Ctl) 0.1 μM | Inh (% of Ctl) 2.5 μM | Inh (% of Ctl) 5 μM | Inh (% of Ctl) 10 μM |
|---|---|---|---|---|---|---|---|---|---|
| 129 | 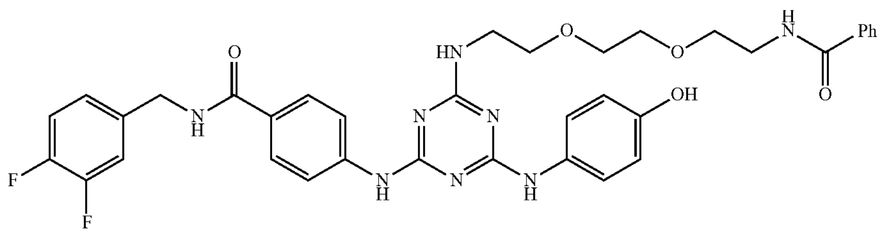 | 812.74 | 8.9 | | 45.1 | 65.6 | | | |
| 130 | 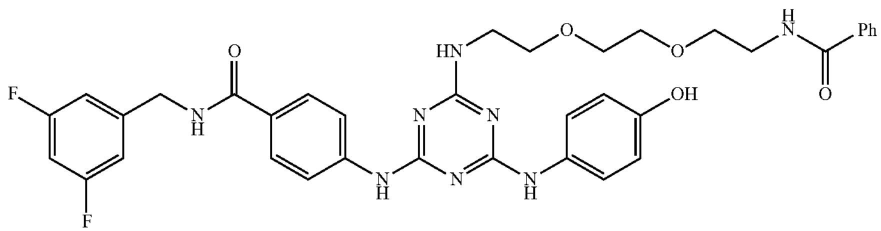 | 812.74 | 41.6 | 73.2 | 81.7 | | | | |
| 131 | 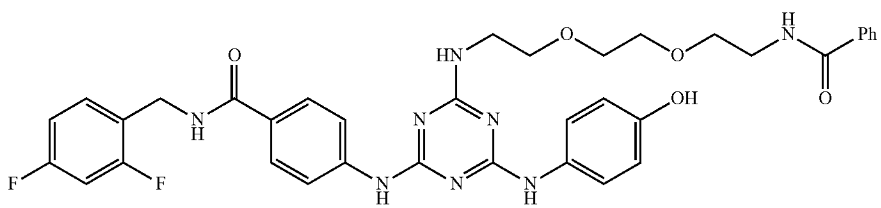 | 812.74 | 22.3 | 47.0 | 74.3 | | | | |
| 132 | 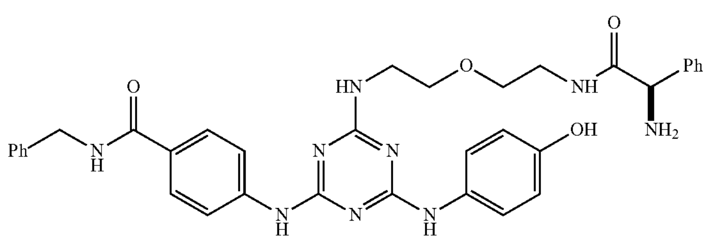 | 875.77 | 15.0 | 22.1 | 32.4 | | | | |

TABLE 1-continued

| | Structure | MS | | | |
|---|---|---|---|---|---|
| 133 | (L-phenylalanine amide linked triazine with 4-hydroxyphenyl and 4-(benzylcarbamoyl)phenyl substituents) | 889.79 | 4.3 | 12.6 | 19.4 |
| 134 | (2-CF3-benzamide linked triazine with 4-hydroxyphenyl and 4-(benzylcarbamoyl)phenyl substituents) | 800.7 | 14.0 | 27.7 | 46.7 |
| 135 | (isonicotinamide linked triazine with 4-hydroxyphenyl and 4-(benzylcarbamoyl)phenyl substituents) | 847.71 | 13.2 | 28.4 | 49.6.6 |
| 136 | (4-F-benzamide linked triazine with 4-hydroxyphenyl and 4-(benzylcarbamoyl)phenyl substituents) | 750.7 23.9 | 33.3 | 64.1 | 77.9 |

TABLE 1-continued

| # | Structure | MW | | | | |
|---|---|---|---|---|---|---|
| 137 | [structure with 4-methoxybenzamide] | 762.73 | 36.7 | 42.0 | 64.9 | 75.6 |
| 138 | [structure with phenylsulfonamide] | 768.76 | 17.8 | 22.5 | 34.5 | |
| 139 | [structure with phenylurea] | 747.72 | 16.3 | 30.7 | 39.0 | |
| 140 | [structure with acetamide] | 670.64 | 11.5 | 4.5 | 10.9 | |

TABLE 1-continued

| | | | | | |
|---|---|---|---|---|---|
| 141 | | 718.72 | 12.7 | 22.0 | 43.5 |
| 142 | | 932.79 | 8.4 | 20.1 | 39.2 |
| 143 (85% pure) | | 812.74 | 16.5 | 33.7 | 57.8 | 69.5 |
| 144 | | 852.78 | 3.4 | 5.8 | 10.8 |
| 145 | | 651.56 | 7.1 | 3.1 | 6.9 |

TABLE 1-continued

| | Structure | MW | | | |
|---|---|---|---|---|---|
| 146 | (structure) | 724.74 | 44.8 | 28.5 | 59.8 | 70.4 |
| 147 | (structure) | 750.7 | 31.7 | 44.5 | 70.2 | 79.5 |
| 148 | (structure) | 786.7 | | 8.4 | 12.9 | 20.7 |

TABLE 1-continued

| | | | | | |
|---|---|---|---|---|---|
| 149 | [structure] | 868.75 | 3.8 | 9.1 | 17.6 |
| 150 | [structure] | 708 | 4.2 | 14.3 | 23.9 |
| 151 | [structure] | | 0.7 | | 8.4 |

C. Treatment of Obesity

Introduction

Vegiopoulos et al. reported that overexpression of cyclooxygenase 2 (COX2) prevented high fat diet (HFD) induced body weight gain by recruiting brown adipocytes (Vegiopoulos et al., 2010), which could increase energy expenditure in the form of heat release. COX is the enzyme controlling the synthesis of prostaglandins (PGs), such as PGI2 and PGE2. Further investigation by the same group revealed that PGI2 analogue induced the differentiation of white adipose tissue (WAT) toward brown adipose tissue (BAT), serving as a molecular mechanism mediating COX2 triggered recruitment of inducible BAT. The biological level of PGs is regulated by their synthesis and catabolism. One of the critical regulators of PG catabolism is prostaglandin transporter (PGT). Global deletion or systemic inhibition of PGT raises PG levels (Chang et al., 2010; Chi et al., 2011). Thus, it was hypothesized that PGT regulates BAT recruitment and thereby modulates energy homeostasis

Methods and Results

Wild type (WT) C57BL6/J mice (purchased from Jackson lab) at 5-6 weeks of age were fed with chow diet (CD) (providing calories 28.5%, 13.5% and 58% from protein, fat and carbohydrate) or high fat diet (HFD) (providing calories 20%, 60% and 20% from protein, fat and carbohydrate). CD and HFD were purchased from Purina LabDiet (Framingham, Mass.), and Research Diets (New Brunswick, N.J.), respectively. PGT global knockout (KO) mice were fed with HFD at 5-6 weeks of age. Simultaneously, WT-CD, WT-HFD, and PGTKO-HFD mice were treated with vehicle (0.4% DMSO+0.4% cremophore) or 0.2 mM Compound 146 from Table 1. To prepare Compound 146 solution, Compound 146 was dissolved in 100% DMSO at a concentration of 50 mM. Two mL of either DMSO or 50 mM Compound 146 were transferred into 500 mL drinking water; 2 mL cremophore were added into the mixture. The mixture was homogenous. Mice were housed individually and fed with CD or HFD, and water (with or without Compound 146) ad libitum. Food and water intakes and body weight were recorded every other day.

FIG. 1A shows that HFD feeding resulted in substantial weight gain as compared to CD feeding. Both PGT deletion and inhibition with Compound 146 ("PV" in FIG. 1) blunted HFD induced weight gain (FIG. 1A), without affecting food or water intake (FIG. 1B, 1C).

Figure 2:
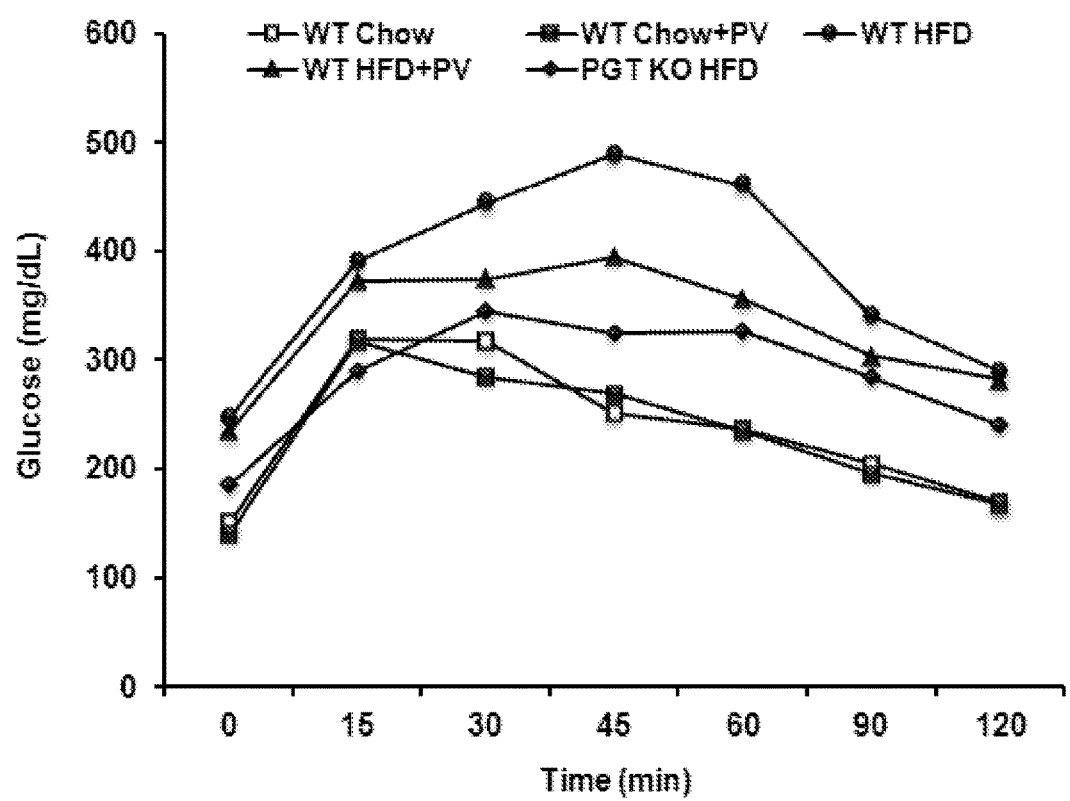
FIG. 2. Glucose tolerance test. WT C57BL6 and PGT KO mice were fed with CD or HFD and treated with vehicle (0.4% DMSO+0.4% cremophore) or 0.2 mM Compound 146 ("PV") in drinking water for 67 days (n=3-4).

Glucose intolerance is often associated with obesity and HFD causes glucose intolerance. Glucose tolerance tests were conducted of mice as shown in FIG. 2. Mice were fasted for 12 hours. Glucose was injected intraperitoneally (20% glucose in saline, 2 g/kg body weight), and plasma glucose levels were measured at various time points by tail cut. FIG. 2 shows that HFD indeed induced glucose intolerance, and both PGT deletion and inhibition improved HFD induced glucose intolerance.

D. Treatment of Pulmonary Arterial Hypertension

Introduction

Studies were designed to test the efficacy of compounds in preventing pathology in a classic rodent model of pulmonary arterial hypertension (PAH). Studies were conducted using Compound 146 from Table 1. Hemodynamic indices of PAH were assessed in the rat monocrotaline (MCT) model. The MCT model of PAH is a routinely used model to evaluate the major pathophysiological features related to PAH and serves as a front-line assay for examining potentially therapeutic compounds (e.g., Li et al., 2013; Paffett et al., 2012). Key pathophysiological variables directly related to mortality and morbidity of PSH were evaluated, including right ventricular systolic pressure (RVSP) and right ventricle to left ventricle plus septum weight (RV/LV+S) ratio.

Materials and Methods

Animals.

These studies were conducted at the University of New Mexico (UNM).

The study complied with all applicable sections of the Final Rules of the Animal Welfare Act regulations (9 CFR Parts 1, 2, and 3) and the *Guide for the Care and Use of Laboratory Animals* (National Research Council, 1996). The protocol was reviewed and approved by the University of New Mexico Institutional Animal Care and Use Committee (IACUC) before the initiation of the study. Sprague-Dawley rats approximately 12 weeks old (300-325 g) from Charles River Laboratories were used in the study.

Tolerability.

In the first arm of the project, the tolerability of compounds was assessed with twice daily (b.i.d) injections in the naive rodent. Following one week of acclimatization to the UNM housing environments, rats at this time weighing approximately 200-225 g were randomly assigned to either receive a 50 mg/kg injection b.i.d. of Compound 146 (n=4) or an equivalent weight-based volume of vehicle (Cremophor-NMP) b.i.d. (n=4). Rats received test article or saline for a total of 7 consecutive days. Blood draws were conducted immediately before the 2nd day of injections, before the 4th day, before the 6th day, and at sacrifice. Body weights were obtained at the same times as the blood draws. On the 7th day, blood from both cohorts was collected via cardiac puncture while under anesthesia. Lungs, heart, liver and kidney were collected and snap frozen in liquid nitrogen for post-mortem bioassays.

Administration of Test Compound Prior to Efficacy Testing.

Monocrotaline (MCT) (Sigma-Aldrich) was formulated by standardized procedures, by first dissolving in an acidic solution (HCl), diluting with distilled $H_2O$, then raising the pH to physiological levels (7.35-7.45) with NaOH. MCT (60 mg/kg) or a volume-matched saline solution was injected intraperitoneally once at the beginning of the study. Body weights were collected on day 0, 5, 7, 11, 14, 18, and 21.

MCT and saline-injected rats (Day 1) were equally and randomly assigned to receive either vehicle (Cremophor-NMP), low dose Compound 146 or high dose Compound 146 via subcutaneous injections (Days 1-21). Injections were administered subcutaneously at 12 hour intervals throughout the study (actual range was 10-14 h).

Efficacy Testing.

After 21 days of twice daily subq injections of either vehicle or two concentrations of Compound 146, rats were anesthetized (1.5-2.5% isoflurane; 2 ml/min $O_2$), shaved and positioned in dorsal recumbence. Anesthesia was maintained at an appropriate depth, with a target heart rate of ~350 bpm to ensure minimal cardio-depressant effects during collection of RVSP.

Upon absent deep pain reflex, a thoracotomy was performed to reveal the right ventricle and a fluid-filled catheter was inserted beyond the right ventricular free wall to permit recording of right ventricular hemodynamics (ADI Instruments). A digital trace of 10-30 seconds was obtained from which to derive right ventricular diastolic, mean, and systolic pressures, along with heart rate and related hemodynamic measures. Blood was then drawn via cardiac puncture and centrifuged to obtain EDTA plasma. Hearts were removed and the right ventricle dissected free from the septal wall. Each piece was weighed and reported as RV/LV+S. Tissues (plasma, heart, and lung) were excised and frozen in liquid nitrogen for later biochemical analysis. Additionally, kidneys and liver were snap frozen and stored for subsequent analysis.

Dose Preparation and Administration. General:

Compound 146 was stored dry at −20° C. Once formulated, solutions were stored at −20° C. When necessary, redissolution was attained through warming (37° C.) and sonication. The compound dissolves in 15% NMP/10% CremophorEL/PBS pH 7.4. The pH of the final solution of Compound 146 should be about <8; therefore, the PBS is still buffering these solutes.

CremophorEL was purchased from Acros Organics (Fisher Scientific) Cat #39728 (250 g). N-methyl pyrrolidinone (NMP) was purchased from Sigma-Aldrich Cat 328634 (100 mL).

The study was initiated with a more dilute formulation. Within about a week of dosing, it was clear that even Vehicle-treated rats were having dermal tolerability issues with the subcutaneous injections. Thus, solutions were reformulated to reduce the concentration of Cremophor and NMP for each injection, which ultimately worked well. The following steps were taken for the first formulation:
1. A solution of Cremophor EL/PBS (pH 7.4) was made by weighing 130 mg of Cremophor and dilute to 1 mL with PBS to make a 13% Cremophor(w/v) solution. When this was added to the compound NMP solution the final Cremophor solution was ~10%. Necessary volumes were modified proportionally depending on the amount of Compound 146 being formulated. Cremophor solution required sonication and heating to 37° C. until homogenous (several minutes).
2. 15 mg of Compound 146 was dissolved in 150 µL of N-methyl pyrrolidinone with sonication to ensure that compound is dissolved (or mixed at proportional level for larger batches).
3. While sonicating, 0.85 mL of the Cremophor/PBS solution was added to the compound/NMP solution. The white precipitate was noted for a few seconds but with continued sonication/heating it readily redissolved.
4. Stock solutions were frozen in aliquots and sonicated/heated for a few minutes prior to loading syringes daily.
5. The final solutions were filtered through 0.2 micron filters for sterilization.

After 11 days and observing a likely Vehicle-related toxicity, solutions were reformulated with a greater proportion of Compound 146 in NMP (proportional to 5 g in 20 ml NMP). This enabled a reduced total volume of single injections from roughly 1 ml to 0.4 ml per rat.

Daily Observations.

Animals were examined twice per day (morning and evening) on each day of the study. Examinations focused on (1) identifying dead, weak, or moribund animals, and (2) documenting the onset and progression of any abnormal clinical signs, especially dermal lesions. Animals found dead were necropsied as soon as possible; for those subjects RV/LVS weight ratios were obtained, but no other parameters were collected.

Statistics.

All data were analyzed by a one-way ANOVA with Newman-Keuls post-hoc multiple comparison test. Probability values less than 0.05 were accepted as significant. Normality of distribution was assumed but for all data sets. All data were analyzed with GraphPad Prism v5.02.

Results

Tolerability.

In this abbreviated mock protocol of the efficacy study, several aspects were noted of concern. For one, the rats dosed with the 50 mg/kg dose of Compound 146 formulated in NMP and Cremophor demonstrated a heterogeneous failure to thrive, while Vehicle treated rats grew consistently over the 7 days period. The 2 rats in the Compound 146 group that did not ultimately gain weight over the 7 day period were noted as each having a 1.5-2.0 cm diameter cutaneous lesion on their back, close to injection sites.

Mortality and Body Weight Changes.

Body weights were captured more frequently than originally planned due to concerns related to vehicle tolerability. However, when the reformulation allowed for a reduced volume of injection (and thus lower dose of the vehicle), growth curves re-established quickly. Recovery of body weight growth was consistent in a general improvement in behavior.

Mortality was observed in several groups, including saline/vehicle. The overall trends were consistent with what is expected for MCT pathology. Importantly, in groups receiving any dose of Compound 146, there were no lethalities. Specific numbers for lethalities are as follows:

| Group | Deaths/Total N |
| --- | --- |
| Saline/vehicle | 1/5 |
| Saline/146hi | 0/5 |
| MCT/vehicle | 2/8 |
| MCT/146lo | 0/8 |
| MCT/146hi | 0/8 | where Compound 146 low dose ("146lo")=15 mg/kg b.i.d., and Compound 146 high dose ("146hi")=50 mg/kg, b.i.d.

Hemodynamics.

Figure 3:
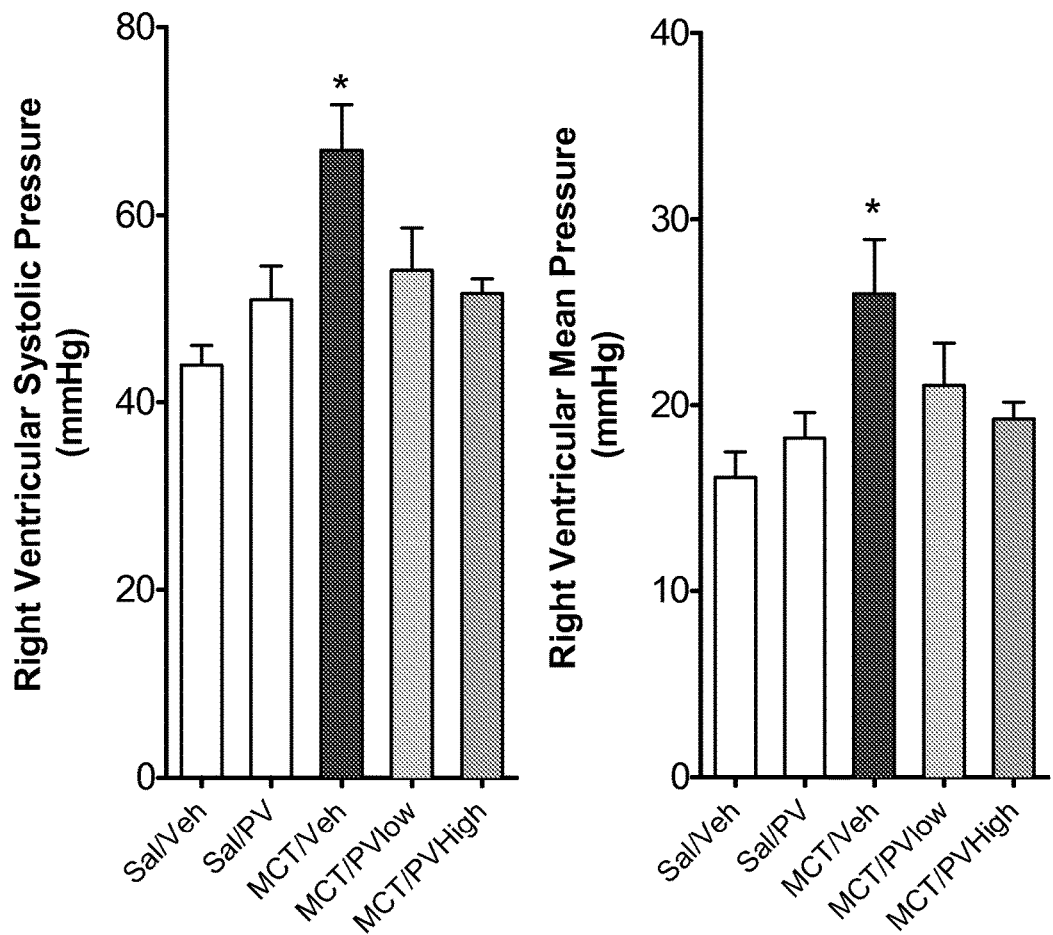
FIG. 3. Right ventricular systolic (RVSP; left) and mean (RVMP; right) pressures in the study subjects. Bars represent mean±S.E. Asterisks represent significant difference from control groups (P<0.05) by ANOVA with Newman-Keuls Multiple Comparison Test. PV=Compound 146; Compound 146 low dose ("PVlow")=15 mg/kg b.i.d.; Compound 146 high dose ("PVHigh")=50 mg/kg, b.i.d.

Right ventricular pressures were obtained on all surviving rats using an open chest method. As expected, MCT caused a significant increase in RV systolic and mean pressures (FIG. 3). In rats receiving either dose of Compound 146, MCT induced no significant effect compared to control rats. However, RV pressures for MCT+Vehicle rats were not statistically different from MCT+Compound 146-treated rats, by ANOVA. Using a restricted analysis of MCT–vehicle compared to MCT–Compound 146, there was a significant reduction by one-tailed unpaired Student's t-test ($P=0.046$ and 0.002 for the low and high dose, respectively).

Figure 4:
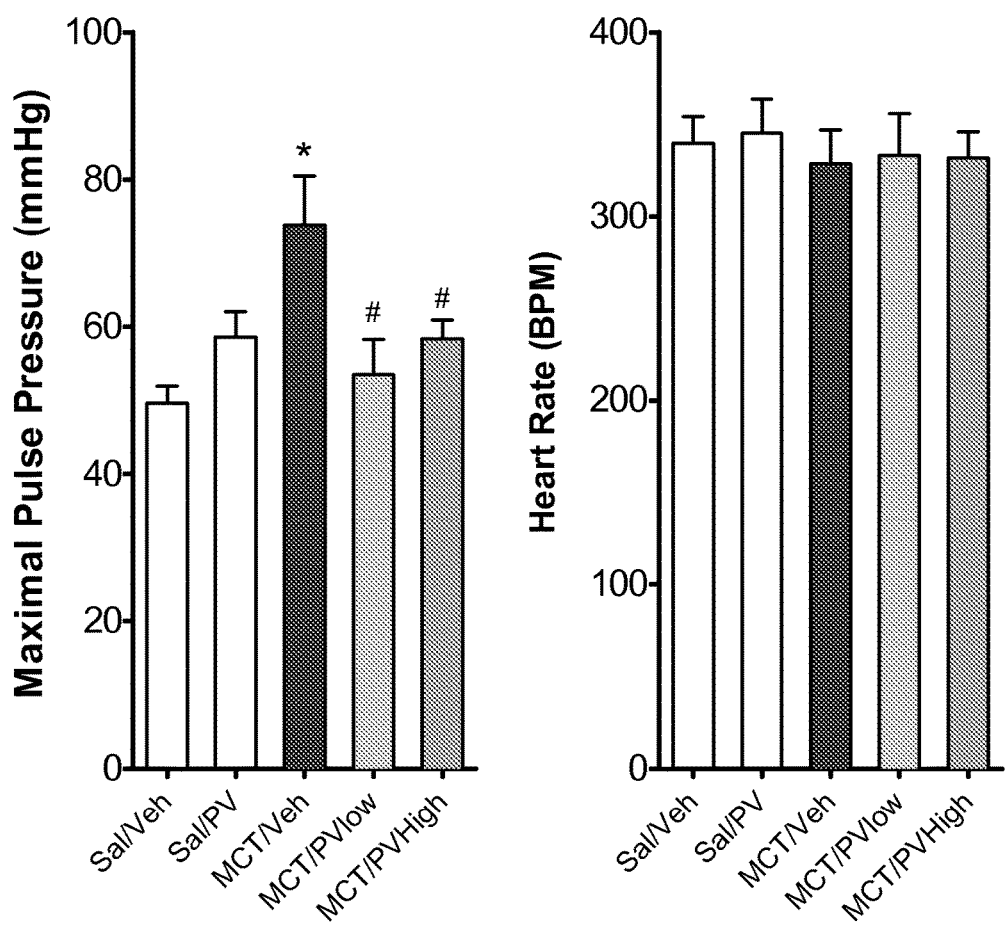
FIG. 4. Right ventricular pulse pressure (left) and heart rate (right) in the study subjects, obtained at sacrifice. Bars represent mean±S.E. The asterisk represents significant difference between the MCT+Vehicle and all other groups (P<0.05) by ANOVA with Newman-Keuls Multiple Comparison Test. Hash mark indicates that MCT+Compound 146 were significantly reduced compared to MCT+Vehicle. PV=Compound 146; Compound 146 low dose ("PVlow")=15 mg/kg b.i.d.; Compound 146 high dose ("PVHigh")=50 mg/kg, b.i.d.

RV pulse pressure (difference from systolic to diastolic blood pressure) was calculated to reduce potential variability related to positioning of the force transducer or catheter tip, which can cause small variations in the zero value. Similar to RVSP and RVMP, MCT caused a significant increase in Vehicle-treated rats compared to saline controls (FIG. 4). Again, in rats receiving either dose of Compound 146, MCT induced no significant effect compared to control rats. For pulse pressure, however, MCT+Vehicle rats were also statistically different from MCT+Compound 146-treated rats, by ANOVA. Lastly, heart rate (HR) was derived from the RV pressure traces in all subjects for the primary purpose of validating that all rats were within a consistent range of anesthesia during the collection of RV pressure data.

Heart Weight and Contractility.

Figure 5:
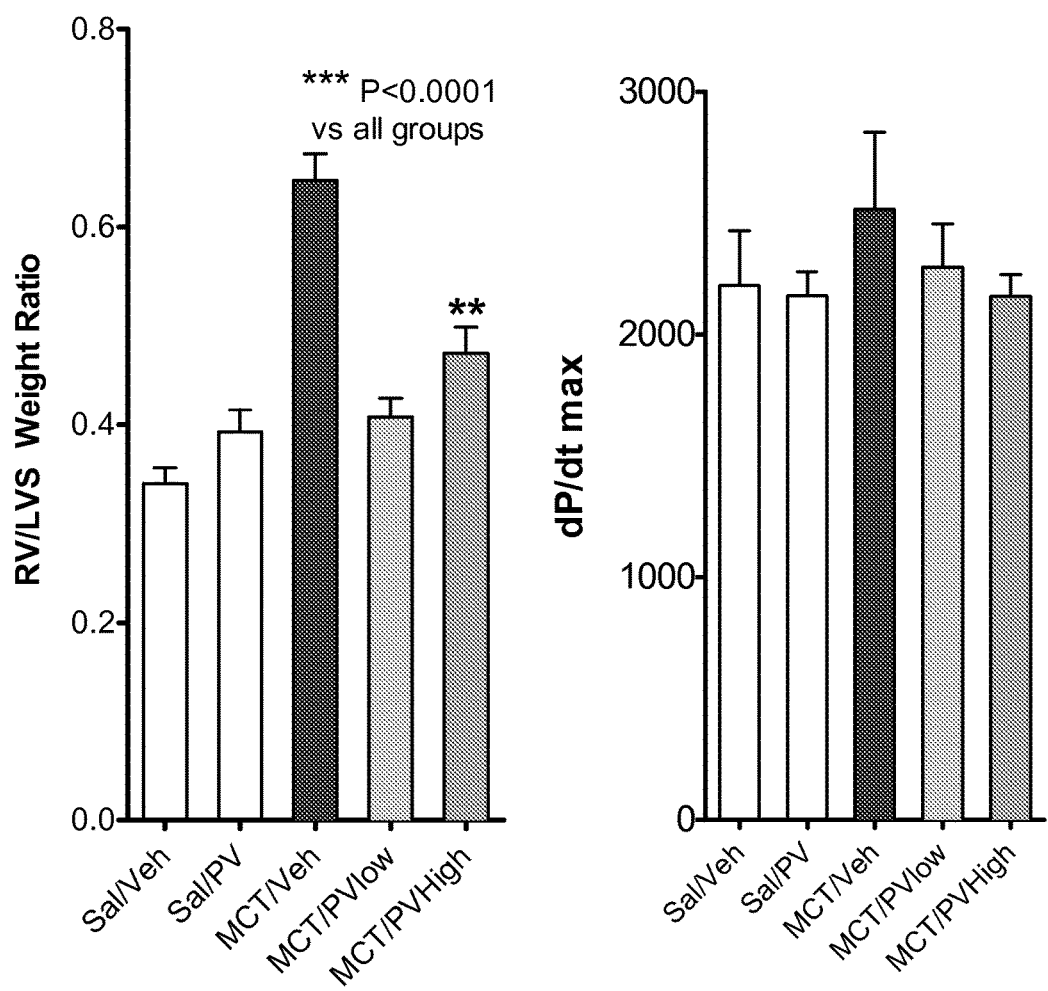
FIG. 5. Right ventricular hypertrophy (RV/LVS, left) and contractility (max dP/dt, right) in the study subjects, obtained at sacrifice. Bars represent mean±S.E. Three asterisks (***) represents significant difference between the MCT-Vehicle groups and all others by ANOVA with Newman-Keuls Multiple Comparison Test (P<0.05). Two asterisks denotes significant difference between MCT-Compound 146 high group and Saline-Vehicle controls (P<0.01). PV=Compound 146; Compound 146 low dose ("PVlow")=15 mg/kg b.i.d.; Compound 146 high dose ("PVHigh")=50 mg/kg, b.i.d.

As expected, MCT induced significant right ventricular hypertrophy, as assessed by the ratio of right ventricle weight divided by left ventricle plus septum weight (RV/LVS, or the Fulton Index; FIG. 5). RV/LVS ratios from saline-treated rats, including those treated with test article, demonstrated mean values of 0.34 to 0.39. MCT-only rats exhibited a mean value of 0.65, which was significantly higher than all saline-treated rats. Both doses of Compound 146 induced a significant inhibition of this RV hypertrophic response, with values of 0.41 and 0.47 in the low and high dose groups, respectively.

Right ventricular contractility did not display conclusive differences between groups and was mainly used to discriminate MCT-treated rats that might have transitioned from hypertrophic to failing conditions, which would impact RVSP values in a manner counter to the study objectives. In this case, we noted that rat #18, a MCT-vehicle subject, had a RVSP value of 42.4 and a +dP/dt value of 1362, which was well below the mean of 2514 for the group. This subject has been removed from all data analysis, as it was suspected that cardiac failure was ongoing.

Figure 6:
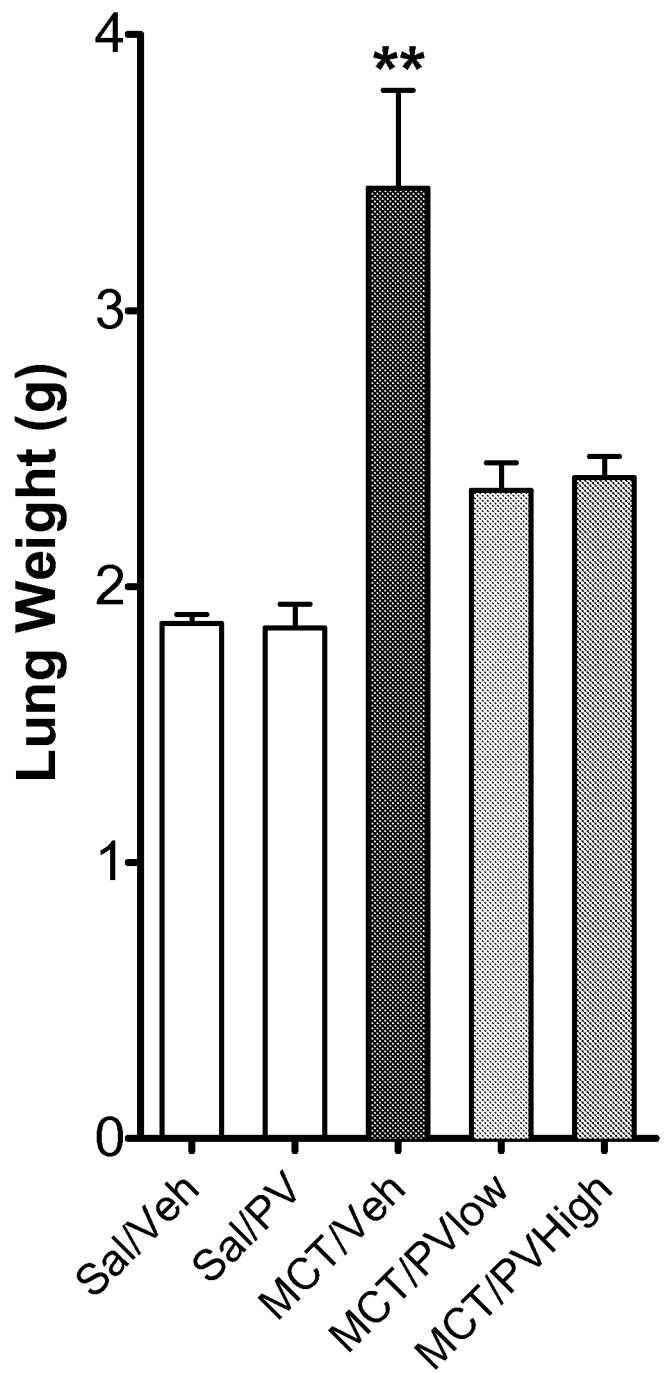
FIG. 6. Total lung weights in all treatment groups. MCT alone increased lung weights compared to all other groups. Asterisks (**) indicate significant difference from control and PV-02076 groups by ANOVA with Newman-Keuls Multiple Comparison Test (P<0.01). PV=Compound 146; Compound 146 low dose ("PVlow")=15 mg/kg b.i.d.; Compound 146 high dose ("PVHigh")=50 mg/kg, b.i.d.

Lastly, as cardiac dissections were not conducted with full operator blinding, FIG. 6 shows the RV and LVS weights were determined for all subjects. Net RV weights were increased by MCT, and the effect blunted by Compound 146. Moreover, there was not an offset in reduced LVS weight. That is, had RV sections been biased, greater LVS weights would be present in the group treated with Compound 146.

Lung Weights.

Figure 7:
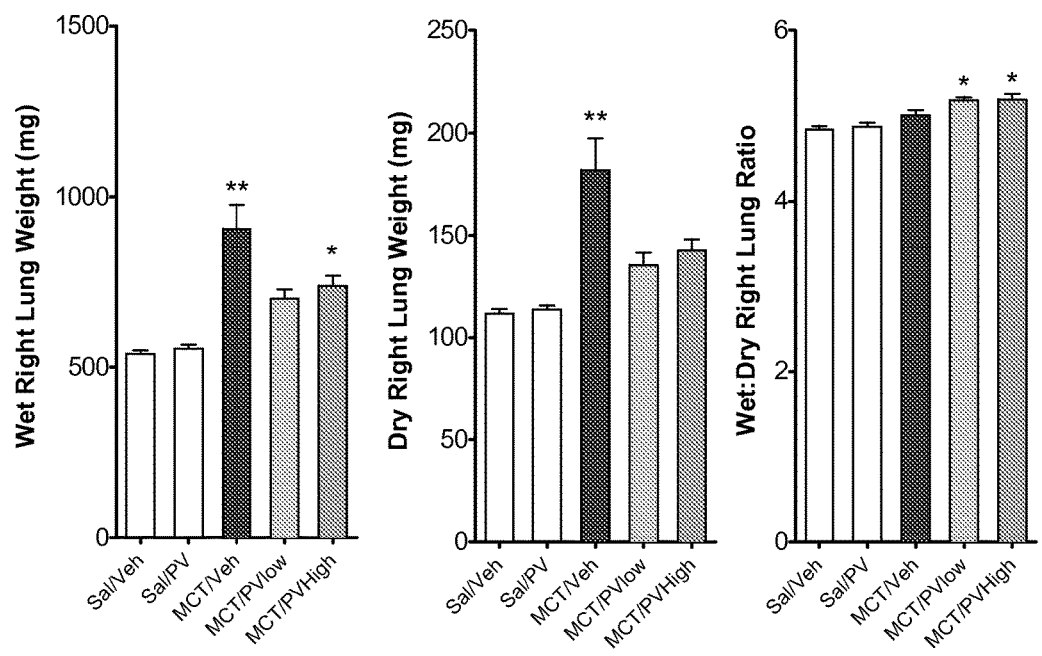
FIG. 7. Right lung lobe wet (left), dry (center) weights and the wet:dry ratio (right) data from all subjects. Two asterisks (**) indicate significant difference from control and PV-02076 groups by ANOVA with Newman-Keuls Multiple Comparison Test (P<0.01). Single asterisks (*) indicate significant different between MCT-PV-02076 groups and Saline-Vehicle. PV=Compound 146; Compound 146 low dose ("PVlow")=15 mg/kg b.i.d.; Compound 146 high dose ("PVHigh")=50 mg/kg, b.i.d.

MCT induced a significant increase in total lung weight that was inhibited by Compound 146 at both doses (FIG. 6). To better understand the nature of this weight gain, the right lobe was dissected away, the wet weight of this single lobe was captured, the lobe was then dried for 5 days, and re-weighed. Wet weights were consistent with the whole lung wet weight data (FIG. 7). Interestingly, dry weights were also consistent with wet weight data, suggesting that MCT treatment led to an increase in structural components of the lung, and that Compound 146 abrogated this remodeling. When the ratio of wet:dry weights were considered, it actually appeared that Compound 146 led to slightly more lung water per mass of tissue in the MCT subjects (but not the saline controls).

Summary

Overall, it was evident that the test article, Compound 146, had a positive outcome in this commonly-used rodent model of pulmonary arterial hypertension. Most cardiopulmonary outcomes showed a significant amelioration of MCT effects by Compound 146. Four principal outcomes measured suggest a benefit from the test article: RVSP, RV/LVS, lung weight, and mortality.

REFERENCES

Agarwal R, Gomberg-Maitland M. Prognostication in pulmonary arterial hypertension. *Heart Fail Clin.* 2012 July; 8(3):373-83.

Alm A (1998) Prostaglandin derivatives as ocular hypotensive agents. *Progress in Retinal and Eye Research* 17:291-312.

Bao Y, Pucci M L, Chan B S, Lu R, Ito S and Schuster V L (2002) Prostaglandin transporter PGT is expressed in cell types that synthesize and release prostanoids. *American Journal of Physiology* 282:F1103-1110.

Bito L Z and Salvador E V (1976) Effects of anti-inflammatory agents and some other drugs on prostaglandin biotransport. *J. Pharmacol. Exp. Ther.* 198:481-488.

Blatteis C M and Sehic E (1997) Fever: How may circulating pyrogens signal the brain?*News in Physiological Sciences.* 12:1-9.

Bley K R, Hunter J C, Eglen R M and Smith J A (1998) The role of IP prostanoid receptors in inflammatory pain. *Trends Pharmacol Sci* 19:141-147.

Bos C L, Richel D J, Ritsema T, Peppelenbosch M P and Versteeg H H (2004) Prostanoids and prostanoid receptors in signal transduction. *Int J Biochem Cell Biol* 36:1187-1205.

Carter R, Mouralidarane A, Ray S, Soeda J, Oben J. Recent advancements in drug treatment of obesity. Clin Med. 2012 October; 12(5):456-60.

Chang, H. Y., Locker, J., Lu, R., and Schuster, V. L. (2010). Failure of postnatal ductus arteriosus closure in prostaglandin transporter-deficient mice. Circulation 121, 529-536.

Chi Y, Khersonsky S M, Chang Y T, Schuster V L. Identification of a new class of prostaglandin transporter inhibitors and characterization of their biological effects on prostaglandin E2 transport. J Pharmacol Exp Ther. 2006 March; 316(3):1346-50. Epub 2005 Nov. 3.

Chi, Y., Min, J., Jasmin, J. F., Lisanti, M. P., Chang, Y. T., and Schuster, V. L. (2011). Development of a high-affinity inhibitor of the prostaglandin transporter. The Journal of Pharmacology and Experimental Therapeutics 339, 633-641.

Clyman R I, Mauray F, Roman C and Rudolph A M (1978) PGE2 is a more potent vasodilator of the lamb ductus arteriosus than is either PGI2 or 6 keto PGF1alpha. *Prostaglandins* 16:259-264.

Coceani F and Olley P M (1988) The control of cardiovascular shunts in the fetal and perinatal period. *Can J Physiol Pharmacol* 66:1129-1134.

Endo S, Nomura T, Chan B S, Lu R, Pucci M L, Bao Y and Schuster V L (2002) Expression of PGT in MDCK cell monolayers: polarized apical localization and induction of active PG transport. *American Journal of Physiology* 282:F618-F622.

Epstein M (1986) *Prostaglandins and the kidney. American journal of medicine; v. 80, no. 1A,* 1986. Technical Publishing, New York, N.Y.

Ferrara N and Davis-Smyth T (1997) The biology of vascular endothelial growth factor. Endocr Rev 18: 4-25.

Helliwell R J, Adams L F and Mitchell M D (2004) Prostaglandin synthases: recent developments and a novel hypothesis. *Prostaglandins Leukotrienes and Essential Fatty Acids* 70:101-113.

Holes-Lewis K A, Malcolm R, O'Neil P M. Pharmacotherapy of obesity: clinical treatments and considerations. Am J Med Sci. 2013 April; 345(4):284-8.

Jacquemin E, Hagenbuch B, Stieger B, Wolkoff A W and Meier P J (1994) Expression cloning of a rat liver $Na^+$-independent organic anion transporter. *Proc Natl Acad Sci USA* 91:133-137.

Kanai N, Lu R, Satriano J A, Bao Y, Wolkoff A W and Schuster V L (1995) Identification and characterization of a prostaglandin transporter. *Science* 268:866-869.

Li J, Long C, Cui W, Wang H. Iptakalim ameliorates monocrotaline-induced pulmonary arterial hypertension in rats. J Cardiovasc Pharmacol Ther. 201318(1):60-9. Epub 2012 Sep. 4.

Mann J R, Backlund M G, Buchanan F G, Daikoku T, Holla V R, Rosenberg D W, Dey S K, and DuBois R N (2006) Repression of prostaglandin dehydrogenase by epidermal growth factor and snail increases prostaglandin E2 and promotes cancer progression. Cancer Res 66: 6649-56.

Narumiya S, Sugimoto Y and Ushikubi F (1999) Prostanoid receptors: structures, properties, and functions. *Physiological Reviews* 79:1193-1226.

Nomura T, Lu R, Pucci M L and Schuster V L (2004) The two-step model of prostaglandin signal termination: in vitro reconstitution with the prostaglandin transporter and prostaglandin 15 dehydrogenase. *Mol Pharmacol* 65:973-978.

Paffett M L, Hesterman J, Candelaria G, Lucas S, Anderson T, Irwin D, Hoppin J, Norenberg J, Campen M J. Longitudinal in vivo SPECT/CT imaging reveals morphological changes and cardiopulmonary apoptosis in a rodent model of pulmonary arterial hypertension. *PLoS One.* 2012; 7(7):e40910, 9 pages, Epub 2012 Jul. 17.

Patel R, Aronow W S, Patel L, Gandhi K, Desai H, Kaul D, Sahgal S P. Treatment of pulmonary hypertension. *Med Sci Monit.* 2012 April; 18(4):RA31-9.

Samad T A, Sapirstein A and Woolf C J (2002) Prostanoids and pain: unraveling mechanisms and revealing therapeutic targets. *Trends Mol Med* 8:390-396.

Santo Domingo L, Scheimann A O. Overview of the epidemiology and management of childhood obesity. *Minerva Pediatr.* 2012 December; 64(6):607-13.

Seybold V S, Jia Y P, and Abrahams L G. Cyclo-oxygenase-2 contributes to central sensitization in rats with peripheral inflammation. *Pain.* 2003 September; 105(1-2):47-55.

Schuster V L (2002) Prostaglandin Transport. *Prostaglandins and Other Lipid Mediators* 68-69:633-647.

Shao J, Sheng G G, Mifflin R C, Powell D W, and Sheng H (2006) Roles of myofibroblasts in prostaglandin E2-stimulated intestinal epithelial proliferation and angiogenesis. *Cancer Res* 66: 846-55.

Sheng H, Shao J, Washington M K, and DuBois R N (2001) Prostaglandin E2 increases growth and motility of colorectal carcinoma cells. *J Biol Chem* 276: 18075-81.

Smith G C S, Coleman R A and McGrath J C (1994) Characterization of dilator prostanoid receptors in the fetal rabbit ductus arteriosus. *Journal of Pharmacology & Experimental Therapeutics* 271:390-396.

Southall M D and Vasko M R (2000) Prostaglandin E(2)-mediated sensitization of rat sensory neurons is not altered by nerve growth factor. *Neurosci Lett* 287: 33-36.

Southall M D and Vasko M R (2001) Prostaglandin receptor subtypes, EP3C and EP4, mediate the prostaglandin E2-induced cAMP production and sensitization of sensory neurons. *J Biol Chem* 276: 16083-91.

Stjernschantz J (1995) Prostaglandins as ocular hypotensive agents; development of an analogue for glaucoma treatment. *Advances in Prostaglandin Thromboxane and Leukotriene Research* 23:63-68.

Stjernschantz J (2004) Studies on ocular inflammation and development of a prostaglandin analogue for glaucoma treatment. *Experimental Eye Research* 78:759-766.

Susanna R, Jr., Chew P and Kitazawa Y (2002) Current status of prostaglandin therapy: latanoprost and unoprostone. *Survey in Ophthalmology* 47 Suppl 1:S97-104.

Sweet D H, Wolff N A and Pritchard J B (1997) Expression cloning and characterization of ROAT1. The basolateral organic anion transporter in rat kidney. *J. Biol. Chem.* 272:30088-30095.

Tsujii M, Kawano S, Tsuji S, Sawaoka H, Hori M, and DuBois R N (1998) Cyclooxygenase regulates angiogenesis induced by colon cancer cells. *Cell* 93: 705-716.

Ulmann A, Silvestre L, Chemama L, Rezvani Y, Renault M, Aguillaume C J. and Baulieu E E (1992) Medical termination of early pregnancy with mifepristone (R U 486) followed by a prostaglandin analogue. Study in 16,369 women. *Acta Obstet. Gynec. Scand.* 71:278-283.

Vanegas H and Schaible H G (2001) Prostaglandins and cyclooxygenases [correction of cycloxygenases] in the spinal cord. *Prog Neurobiol* 64:327-363.

Vegiopoulos, A., Muller-Decker, K., Strzoda, D., Schmitt, I., Chichelnitskiy, E., Ostertag, A., Berriel Diaz, M., Rozman, J., Hrabe de Angelis, M., Nusing, R. M., et al. (2010). Cyclooxygenase-2 controls energy homeostasis in mice by de novo recruitment of brown adipocytes. Science 328, 1158-1161.

Wang J L, Cheng H F, Zhang M Z, McKanna J A and Harris R C (1998) Selective increase of cyclooxygenase-2 expression in a model of renal ablation. *Am. J. Physiol.* 275:F613-F622.

Yao A. Recent advances and future perspectives in therapeutic strategies for pulmonary arterial hypertension. *J Cardiol.* 2012 November; 60(5):344-9. Epub 2012 Oct. 12.

Yokoyama C, Yabuki T, Shimonishi M, Wada M, Hatae T, Ohkawara S, Takeda J, Kinoshita T, Okabe M and Tanabe T (2002) Prostacyclin-deficient mice develop ischemic renal disorders, including nephrosclerosis and renal infarction. *Circulation* 106:2397-2403.

Young M R (2004) Tumor-derived prostaglandin E2 and transforming growth factor-beta stimulate endothelial cell motility through inhibition of protein phosphatase-2A and involvement of PTEN and phosphatidylinositide 3-kinase. Angiogenesis 7: 123-131.

U.S. Pat. No. 5,792,851, issued Aug. 11, 1998, Human Prostaglandin Transporter, Schuster et al.

U.S. Patent Application Publication No. US 2012/0238577, published Sep. 20, 2012, Prostaglandin Transporter Inhibitors and Uses Thereof, Schuster et al.

PCT International Patent Application Publication No. WO 2007/136638 A2, published Nov. 29, 2007, Prostaglandin Transporter Inhibitors.

What is claimed is:

1. A method of treating a condition selected from the group consisting of obesity and pulmonary arterial hypertension comprising administering to a subject having obesity and/or pulmonary arterial hypertension a compound of formula (I) in an amount effective to treat obesity and/or pulmonary arterial hypertension, wherein if the subject has obesity, the compound is administered in an amount effective to reduce glucose intolerance, wherein if the subject has pulmonary arterial hypertension, the compound is administered in an amount effective to reduce right ventricular pulse pressure, and wherein formula (I) is:

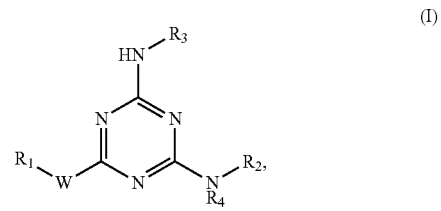

wherein
W is O or NR5;
R1 is H, —CH$_3$, —(CH$_2$)$_2$OH,

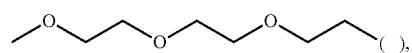

-continued
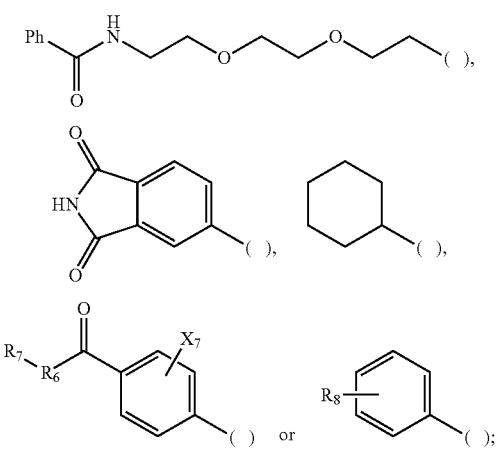
R2 is
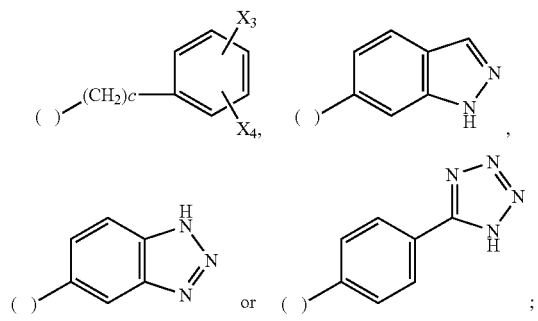
R3 is —(CH₂)₅CH₃, —(CH₂)₆CO₂H, —(CH₂)₆CO₂CH₃,
—(CH₂)$_d$NHCO-Ph, —(CH₂)₆CONH-Ph,
—(CH₂)₆CONHCH₂-Ph,
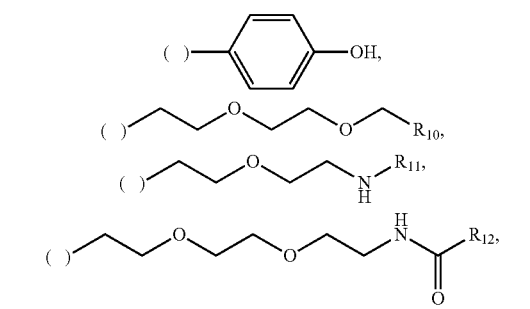
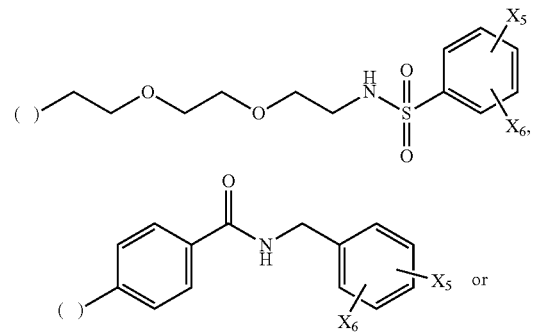
-continued
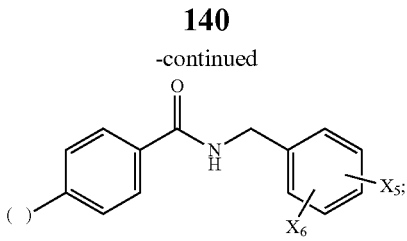
R4 and R5 are independently H or —CH₃;
R6 is O or NR9;
R7 is H, —CH₃, —C(CH₃)₃, —CH₂OH, —(CH₂)₂OH,
—(CH₂)₂O(CH₂)₂OH, —(CH₂CH₂O)₃CH₃,
—(CH₂CH₂O)₂CH₂CO₂CH₃, —(CH₂)₅CH₃,
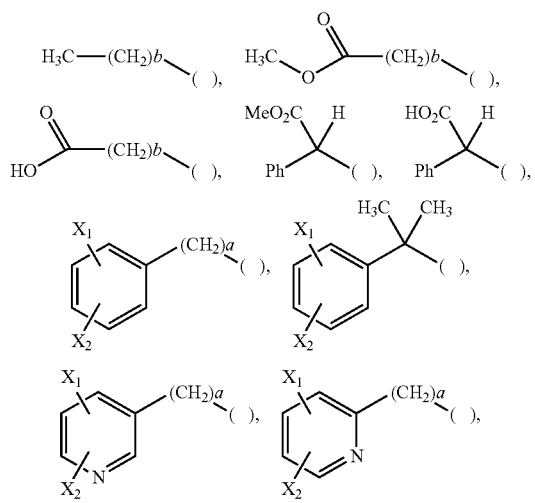
R8 is H, —OH, —CH₂OH, —CO₂H, —CO₂CH₂CH₃,
—CO(CH₂)₆CH₃, —OCH₃, —NH₂, —SO₂NH₂,
—CONH-Bn or
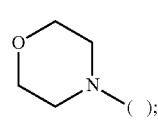
R9 is H or —CH₃;
R10 is —CH₂NH₂, —CO₂H or —CO₂CH₃;
R11 is —SO₂-Ph, —CH₂-Ph, —CONH-Ph, —COCH₃,

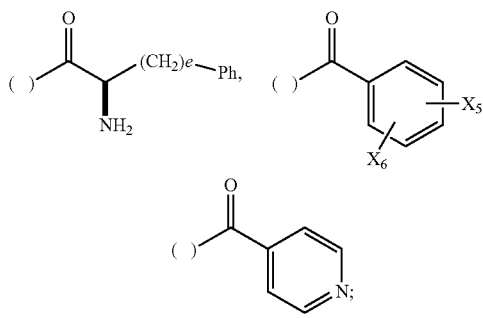

and

R12 is —CH$_3$

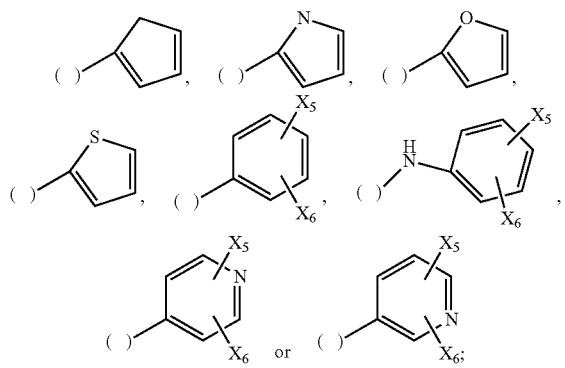

where X1, X2, X3, X4, X5, X6 and X7 are independently H, halogen, —OH, —CH$_3$, —CF$_3$, —OCH$_3$, —CO$_2$H, —CO$_2$CH$_3$, —CH$_2$CO$_2$H, —CH$_2$CO$_2$CH$_3$, phenyl or —O-Bn; and where a=0-2; b=1-6; c=0-1; d=4-7; and e=0-1; or a pharmaceutically acceptable salt thereof.

2. The method of claim 1, wherein W is NR5.
3. The method of claim 1, wherein R6 is NR9.
4. The method of claim 1, wherein at least one of R4, R5 and R9 is H.
5. The method of claim 1, wherein all of R4, R5 and R9 are H.
6. The method of claim 1, wherein one of X1 and X2 is H, and the other is halogen, —CF$_3$, —CH$_3$, —CO$_2$H, —CO$_2$CH$_3$, —OCH$_3$ or phenyl.
7. The method of claim 1, wherein one of X3 and X4 is —OH, and the other is halogen, —CO$_2$H or —CO$_2$CH$_3$.
8. The method of claim 1, wherein X7 is H, —CF$_3$ or —OCH$_3$.
9. The method of claim 1, wherein X1 is located in meta position and X2 is located in para position.
10. The method of claim 1, wherein X1 is located in ortho position and X2 is located in para position.
11. The method of claim 1, wherein X3 is in meta position and X4 is in para position.
12. The method of claim 1, wherein X5 or X6 is in meta position.
13. The method of claim 1, wherein X5 or X6 is in para position.
14. The method of claim 1, wherein the compound has the structure:

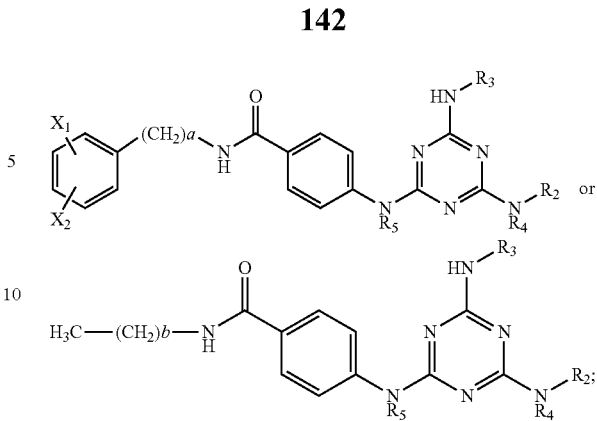

or a pharmaceutically acceptable salt thereof.

15. The method of claim 1, wherein the compound has the structure:

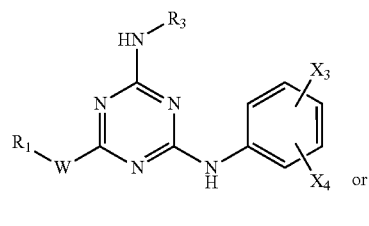

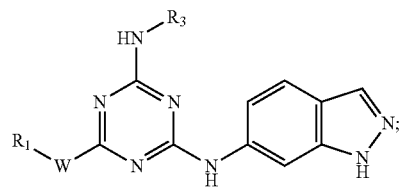

or a pharmaceutically acceptable salt thereof.

16. The method of claim 1, wherein the compound has the structure:

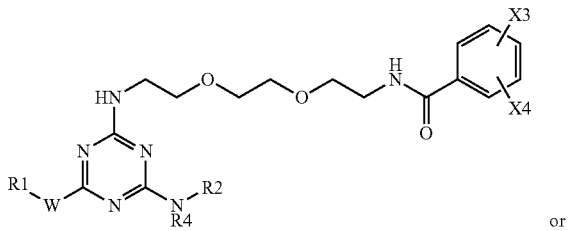

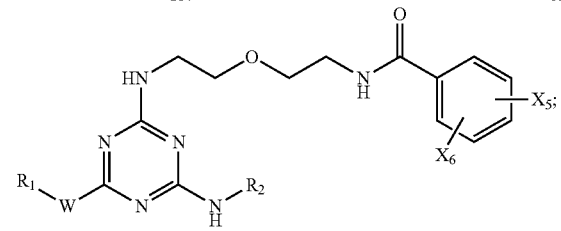

or a pharmaceutically acceptable salt thereof.

17. The method of claim 1, wherein
R1 is

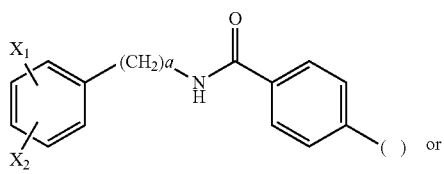

or

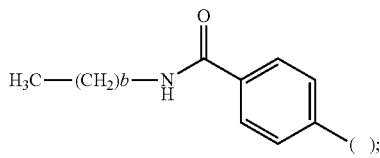

;

R2 is

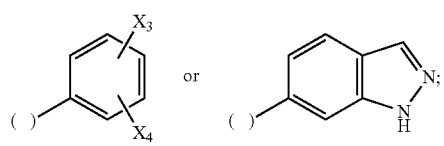

and
R3 is

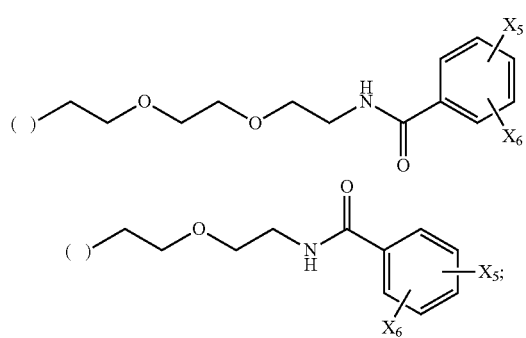

and
where X1, X2, X3, X4, X5 and X6 are independently H, halogen, —OH, —CH$_3$, —CF$_3$, —OCH$_3$, —CO$_2$H, —CO$_2$CH$_3$, —CH$_2$CO$_2$H or —CH$_2$CO$_2$CH$_3$, and
where a=1-2; and b=1-5;
or a pharmaceutically acceptable salt thereof.

18. The method of claim 1, wherein
R1 is

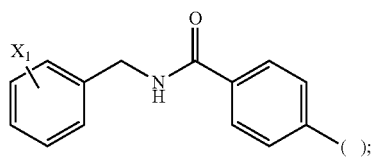

;

R2 is

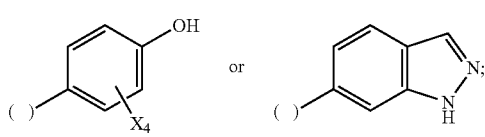

and
R3 is

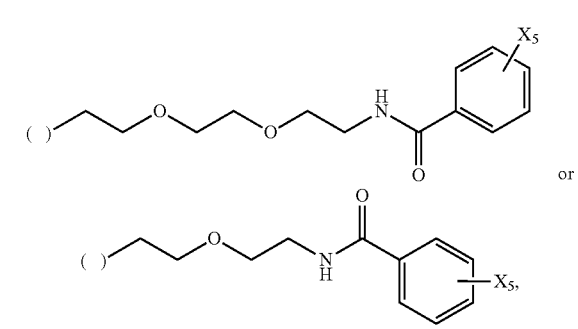

and
where X1 is H or halogen;
where X4 is H, halogen or —CO$_2$H; and
where X5 is H, halogen or —OCH$_3$;
or a pharmaceutically acceptable salt thereof.

19. The method of claim 1, where R5 is H.

20. The method of claim 1, wherein the compound has the structure:

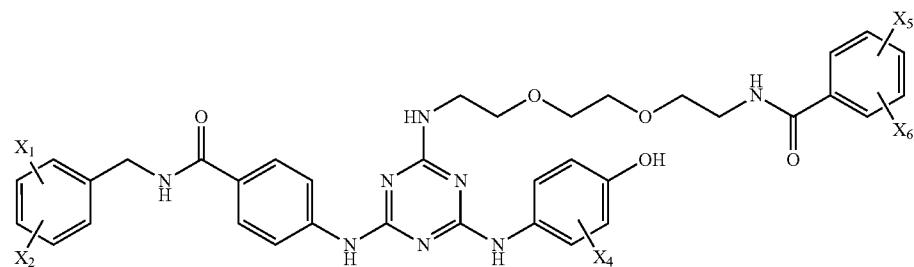

or a pharmaceutically acceptable salt thereof.

21. The method of claim 1, wherein the halogen is Br, Cl or F.

22. The method of claim 1, wherein the compound has the structure:

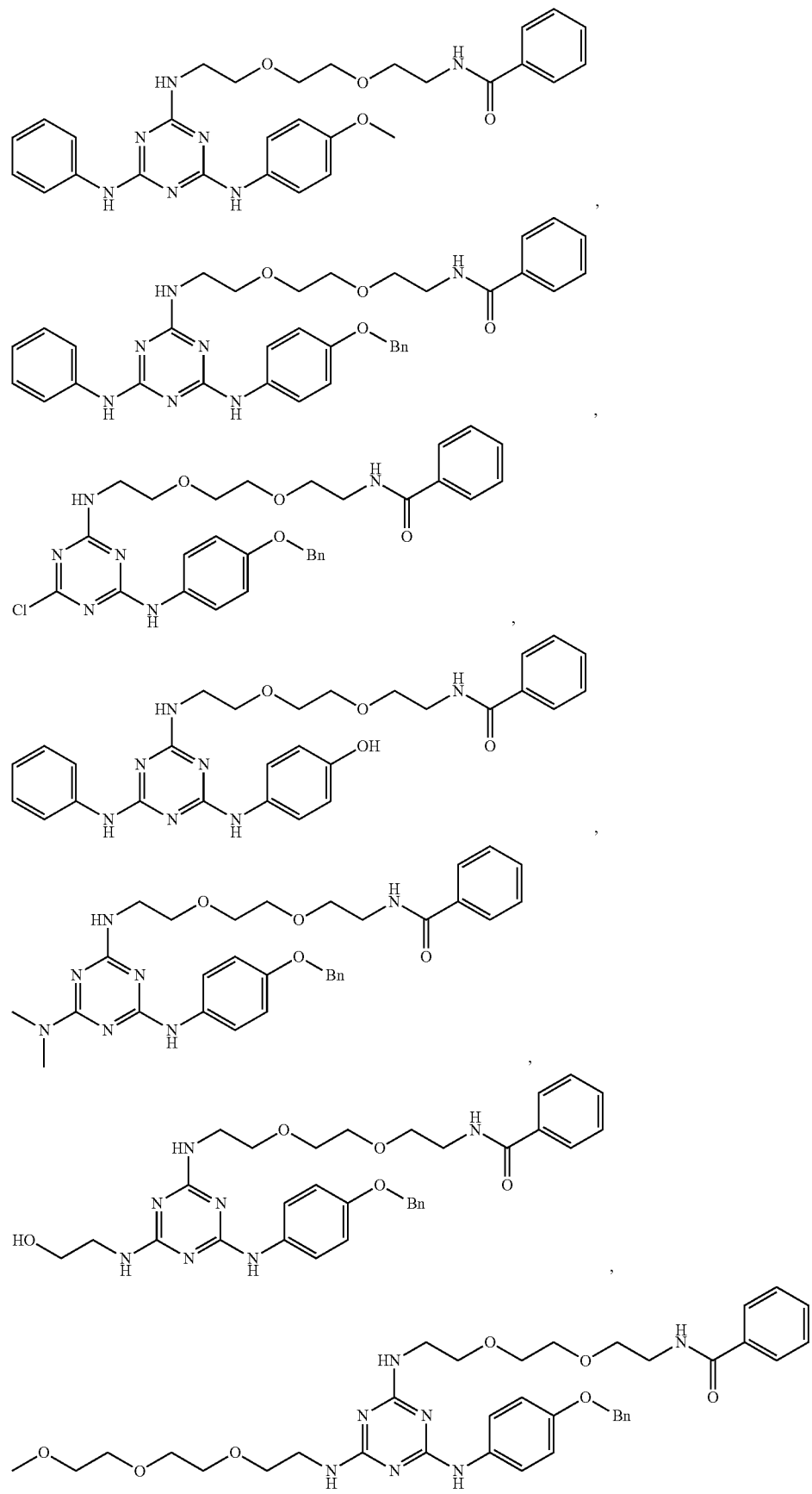

-continued
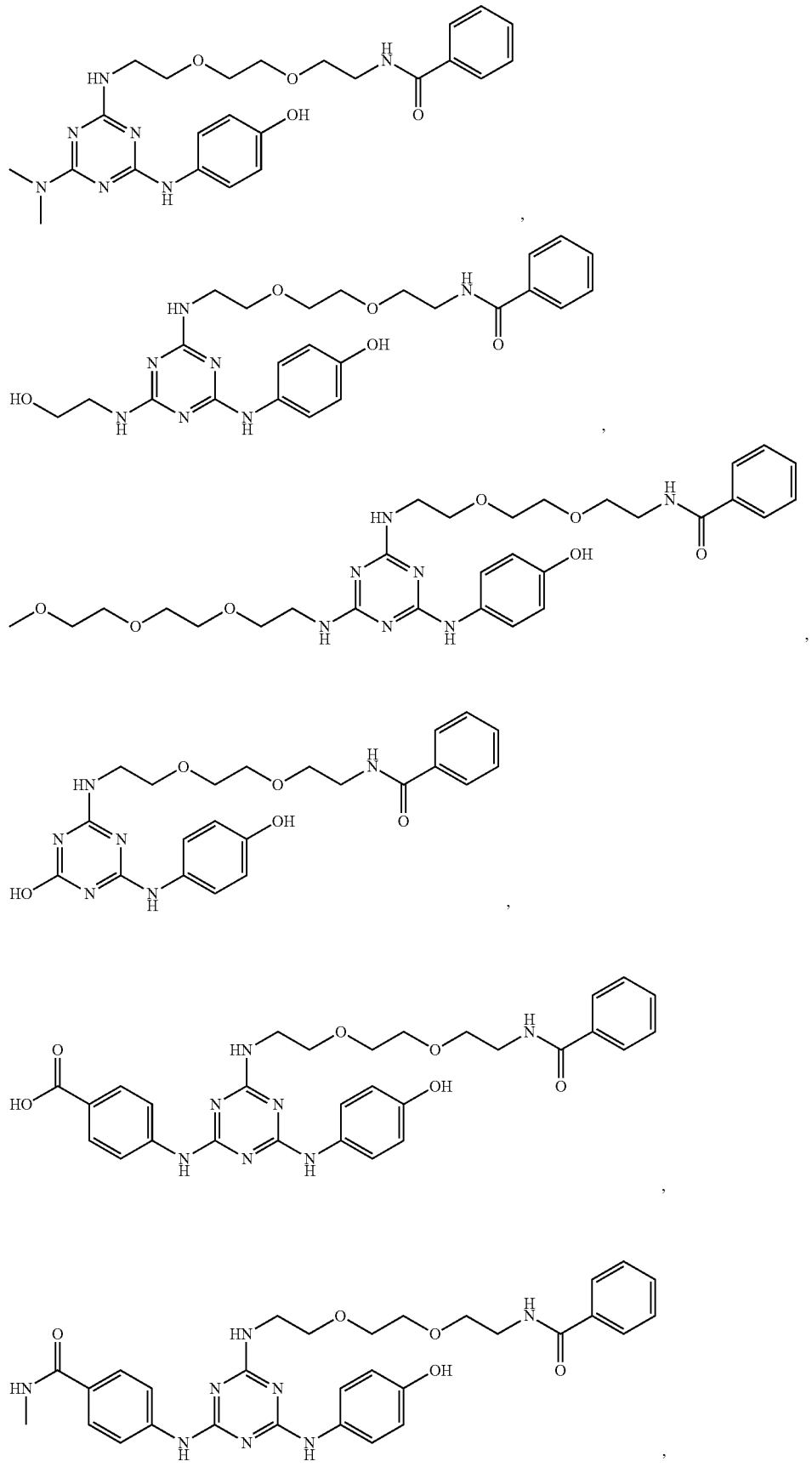

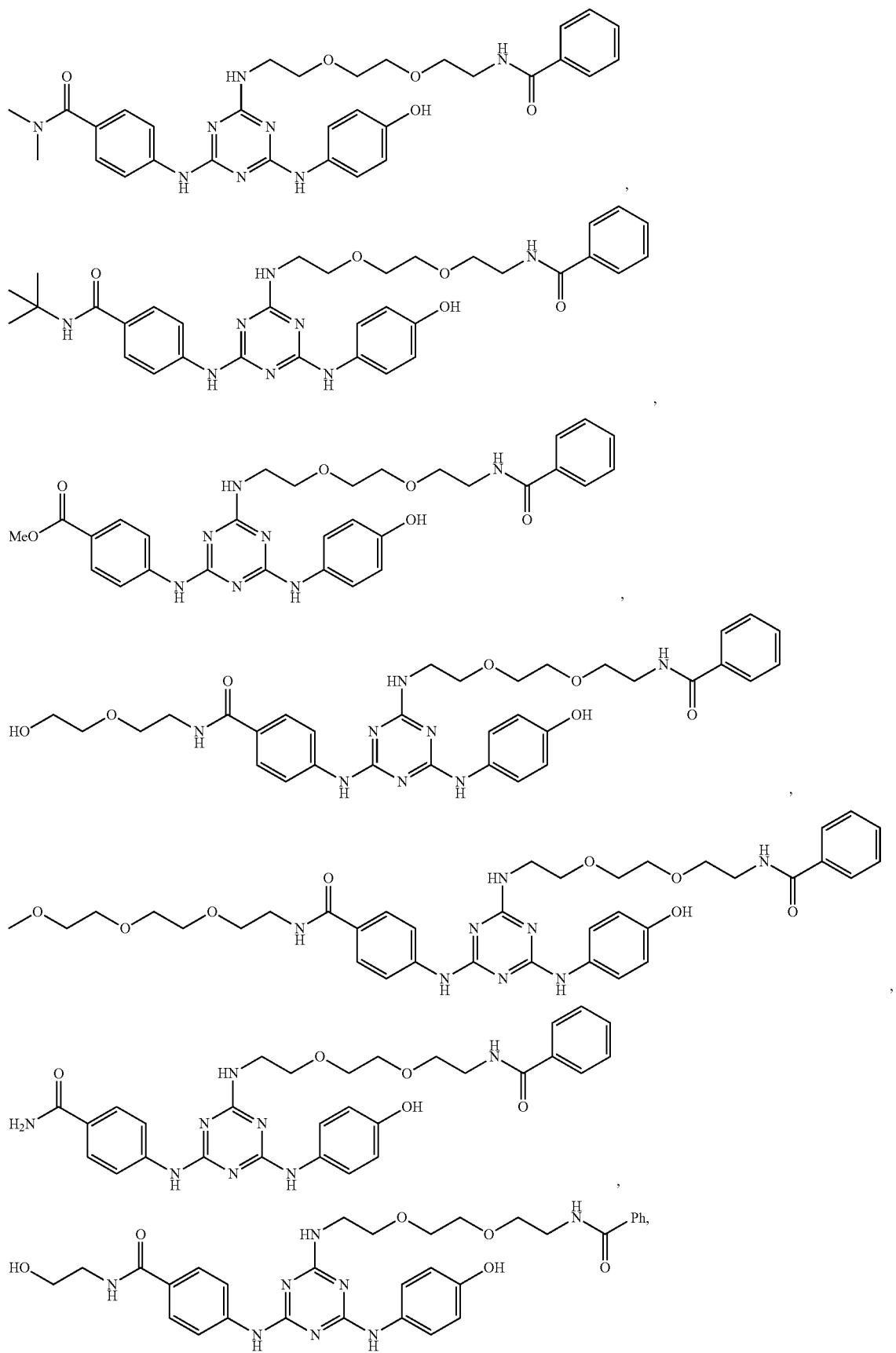

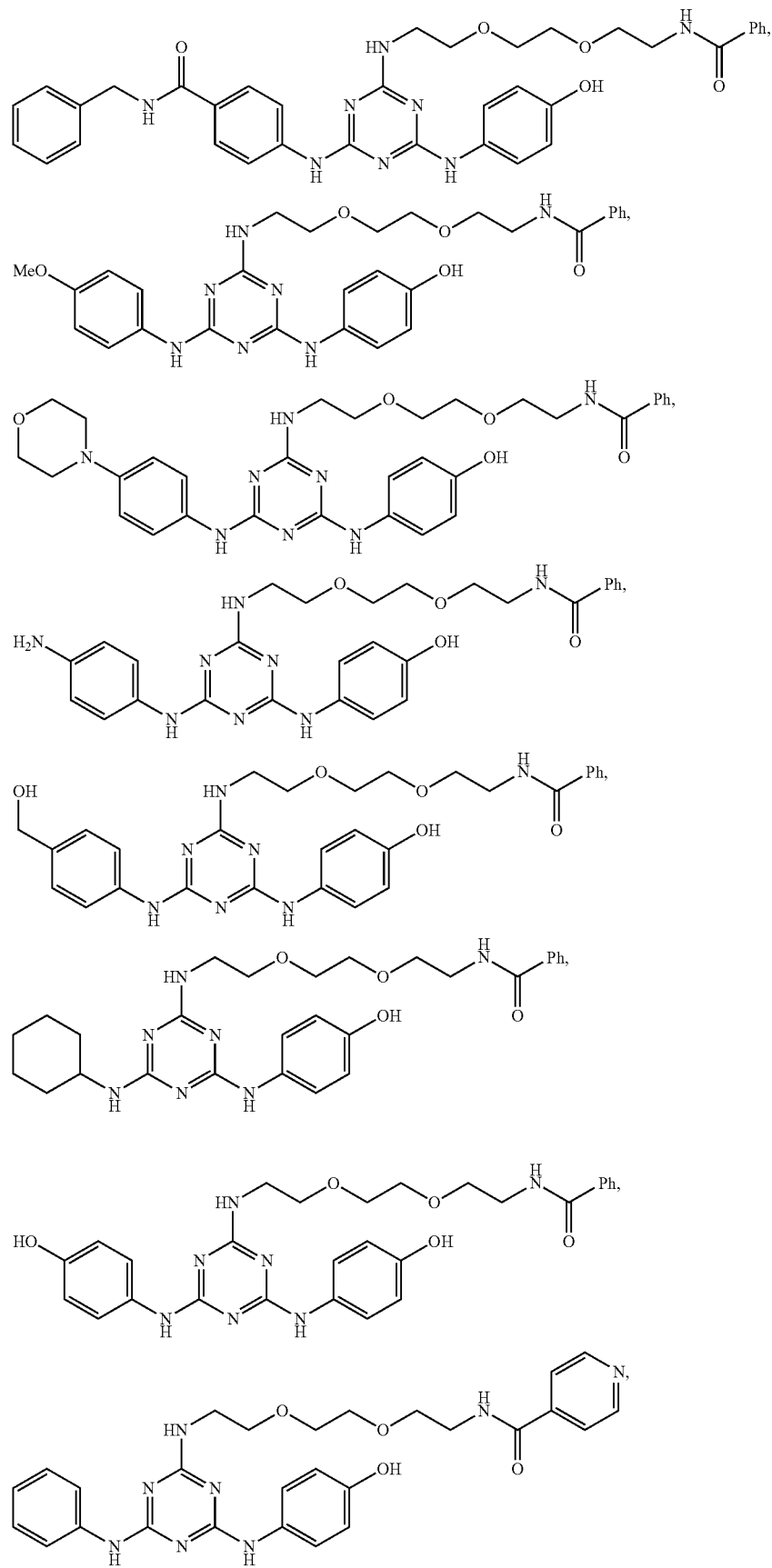

-continued
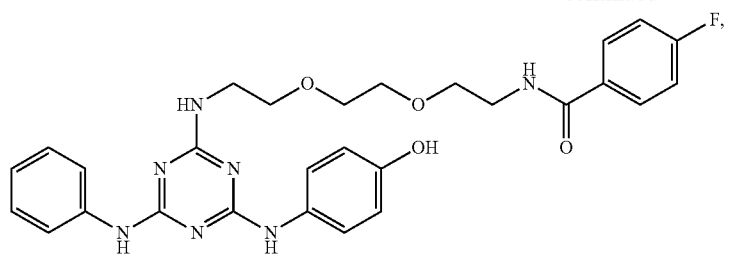 [SMILES: O=C(NCCOCCOCCNc1nc(Nc2ccccc2)nc(Nc2ccc(O)cc2)n1)c1ccc(Br)cc1]
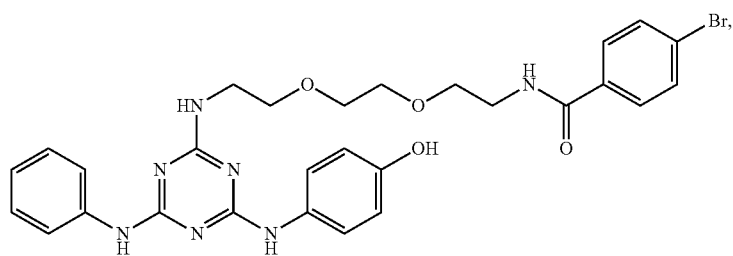
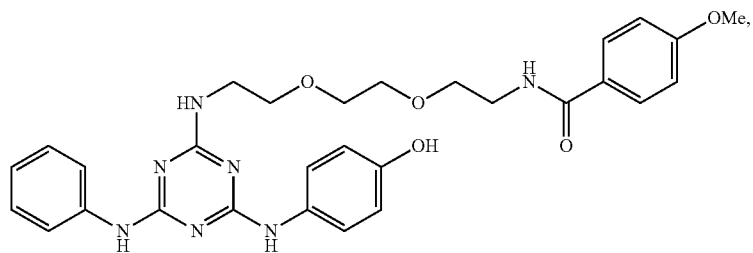 [SMILES: COc1ccc(C(=O)NCCOCCOCCNc2nc(Nc3ccccc3)nc(Nc3ccc(O)cc3)n2)cc1]
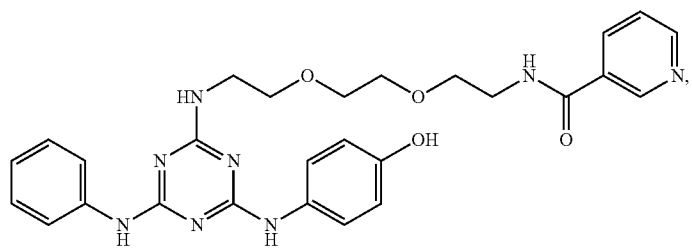 [SMILES: O=C(NCCOCCOCCNc1nc(Nc2ccccc2)nc(Nc2ccc(O)cc2)n1)c1cccnc1]
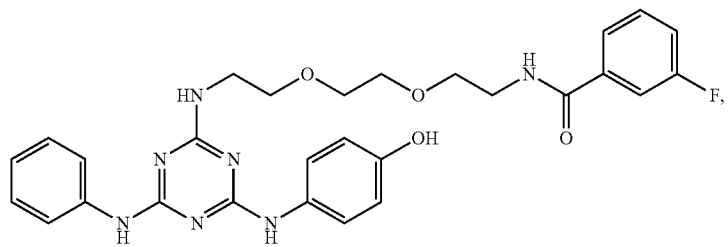
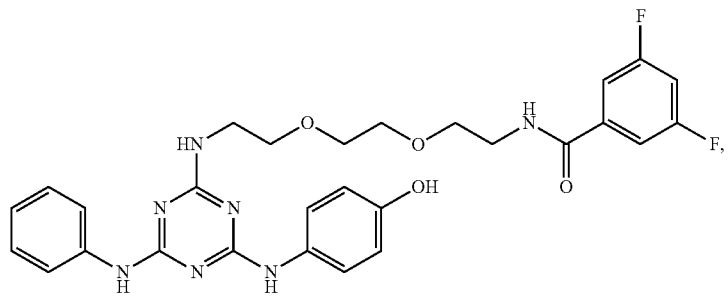 [SMILES: O=C(NCCOCCOCCNc1nc(Nc2ccccc2)nc(Nc2ccc(O)cc2)n1)c1cc(F)cc(F)c1]

-continued
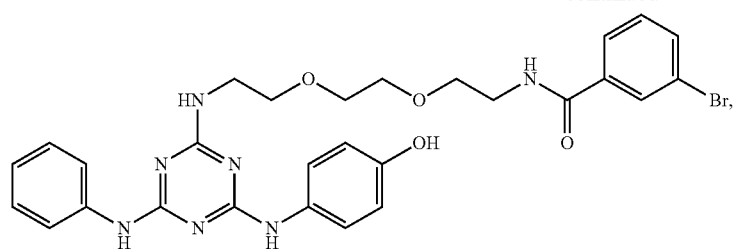 [SMILES: O=C(NCCOCCOCCNc1nc(Nc2ccccc2)nc(Nc2ccc(O)cc2)n1)c1cccc(Br)c1]
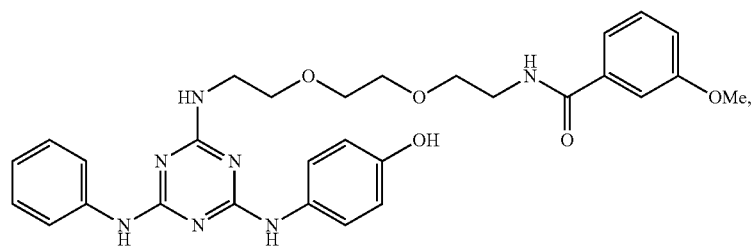 [SMILES: COc1cccc(C(=O)NCCOCCOCCNc2nc(Nc3ccccc3)nc(Nc3ccc(O)cc3)n2)c1]
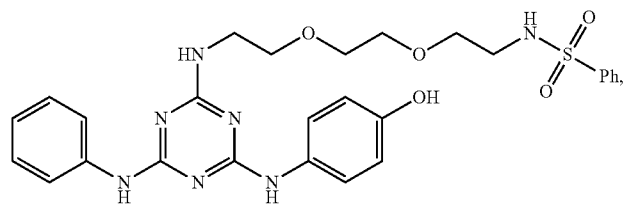 [SMILES: O=S(=O)(NCCOCCOCCNc1nc(Nc2ccccc2)nc(Nc2ccc(O)cc2)n1)c1ccccc1]
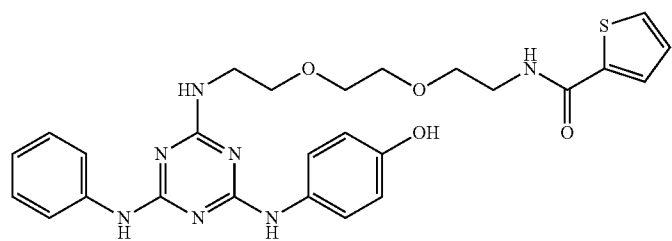 [SMILES: O=C(NCCOCCOCCNc1nc(Nc2ccccc2)nc(Nc2ccc(O)cc2)n1)c1cccs1]
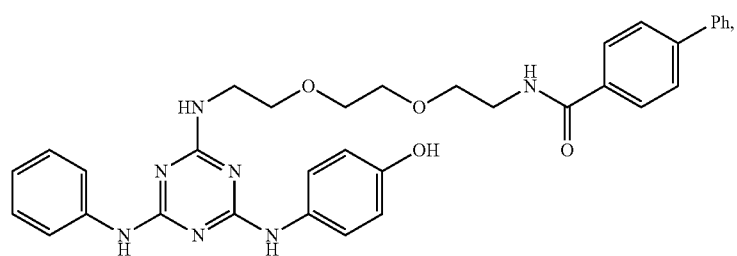
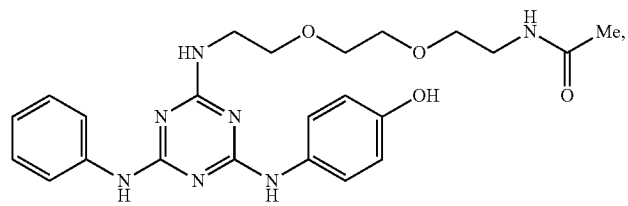
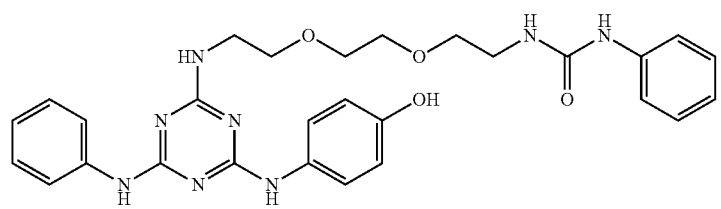 [SMILES: O=C(NCCOCCOCCNc1nc(Nc2ccccc2)nc(Nc2ccc(O)cc2)n1)Nc1ccccc1]

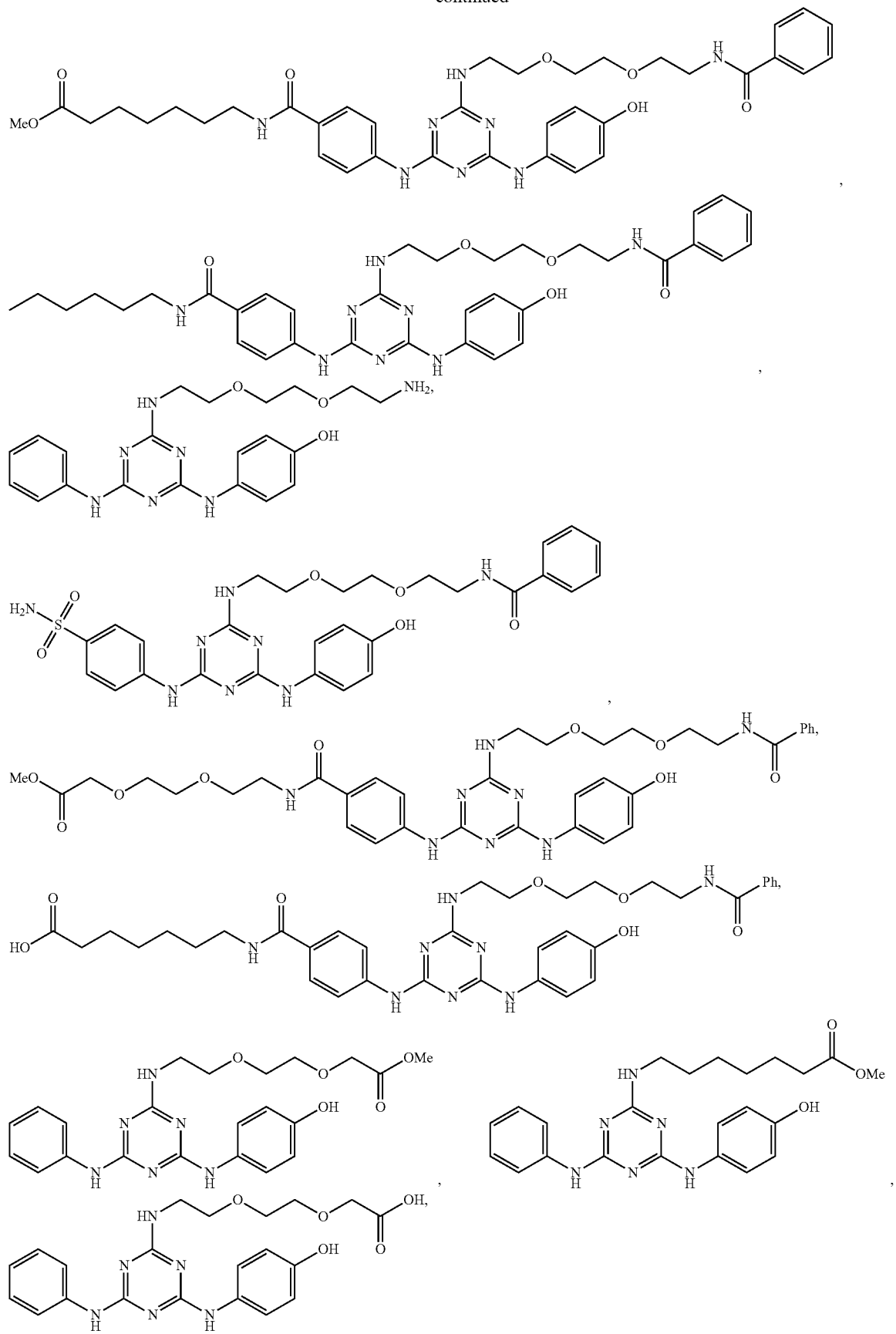

-continued
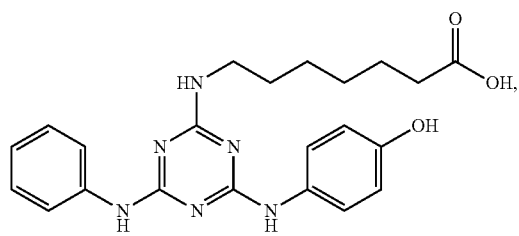
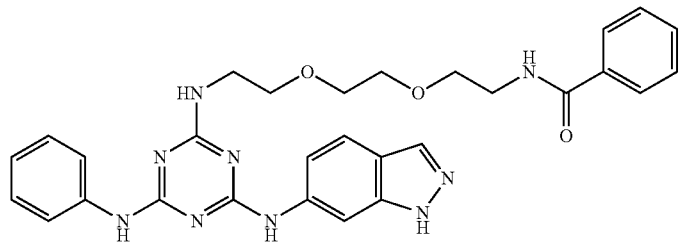 [SMILES: O=C(NCCOCCOCCNc1nc(Nc2ccccc2)nc(Nc2ccc3cn[nH]c3c2)n1)c1ccccc1]
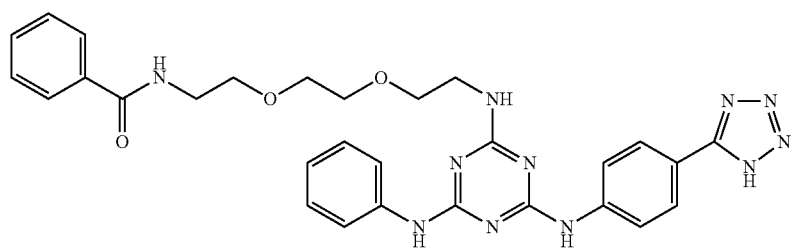 [SMILES: O=C(NCCOCCOCCNc1nc(Nc2ccccc2)nc(Nc2ccc(-c3nnn[nH]3)cc2)n1)c1ccccc1]
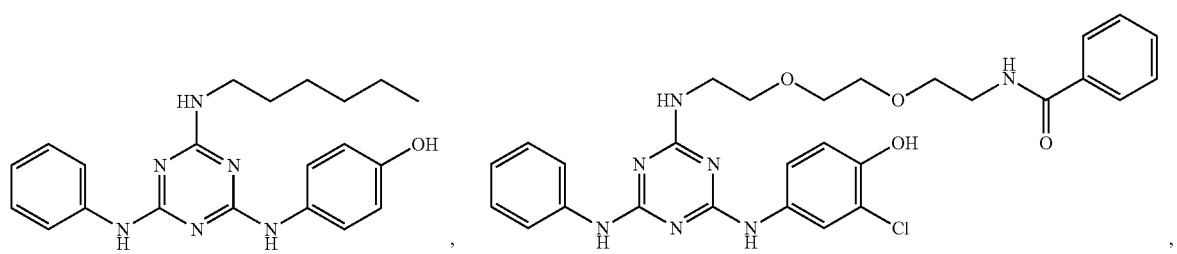
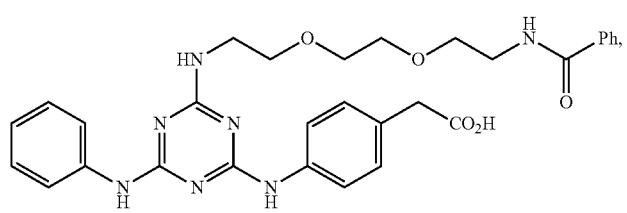 [SMILES: O=C(O)Cc1ccc(Nc2nc(NCCOCCOCCNC(=O)c3ccccc3)nc(Nc3ccccc3)n2)cc1]
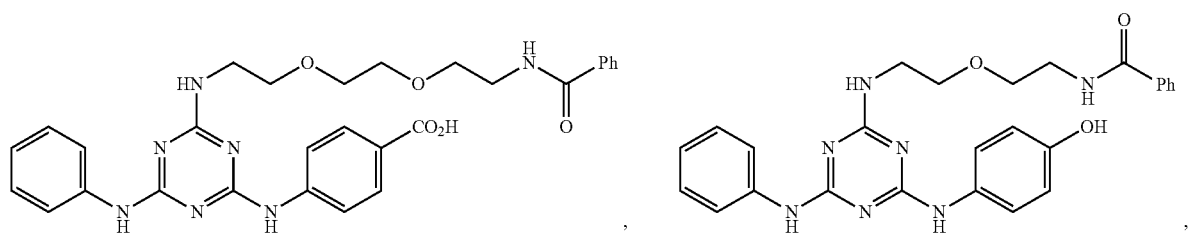
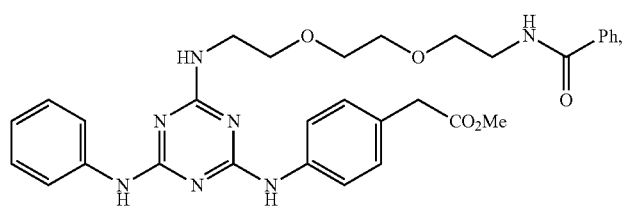

161 162
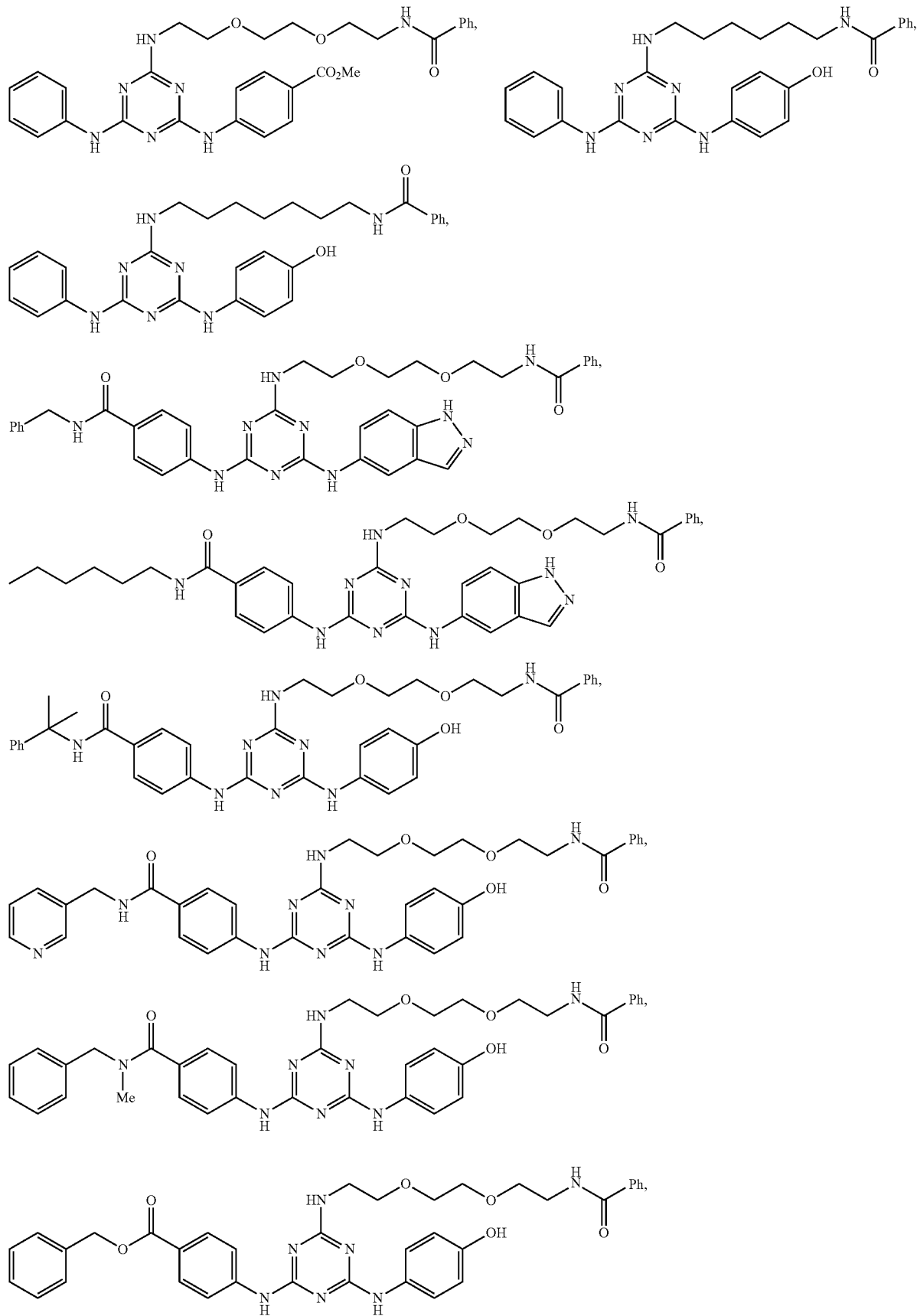

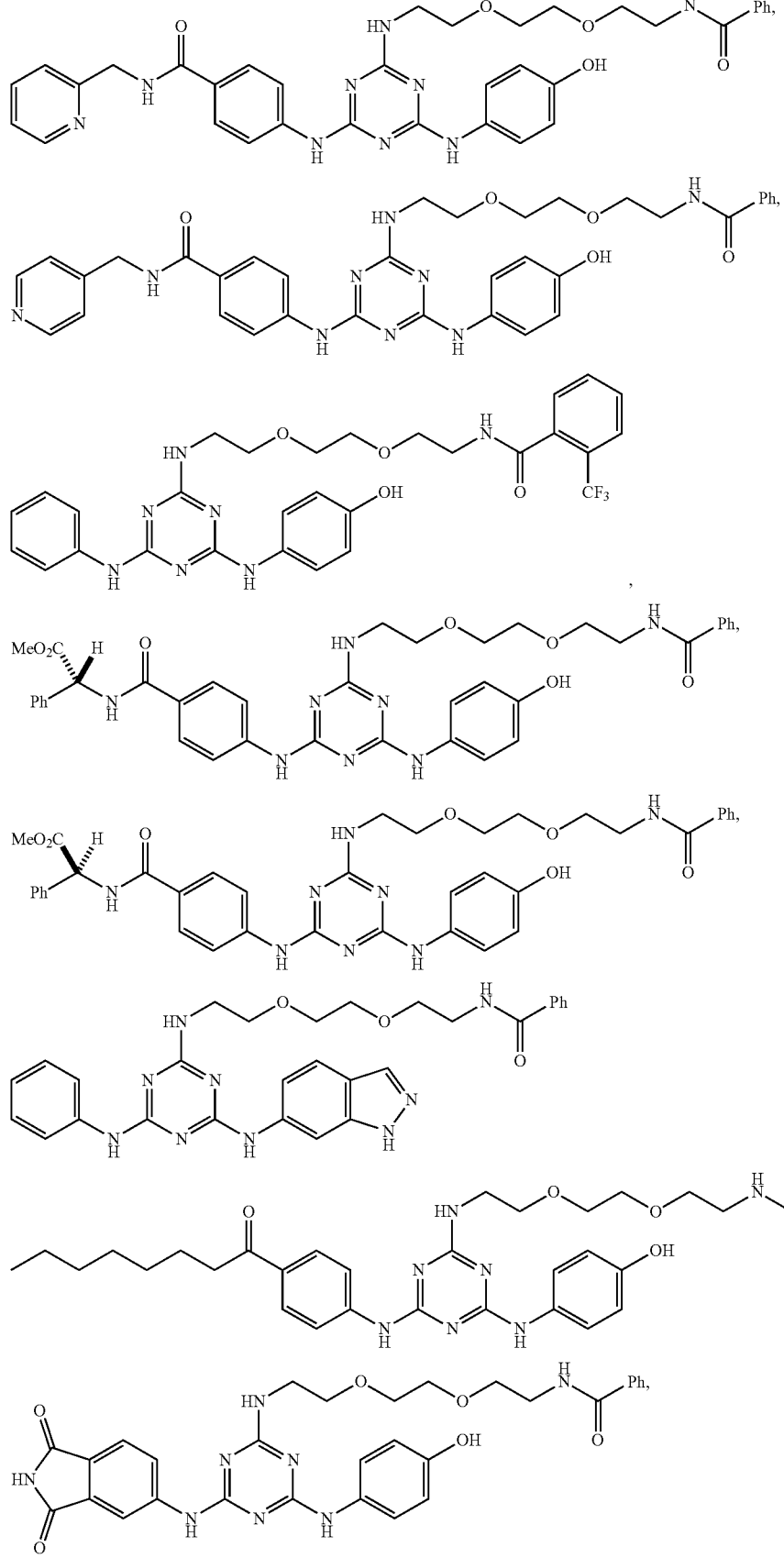

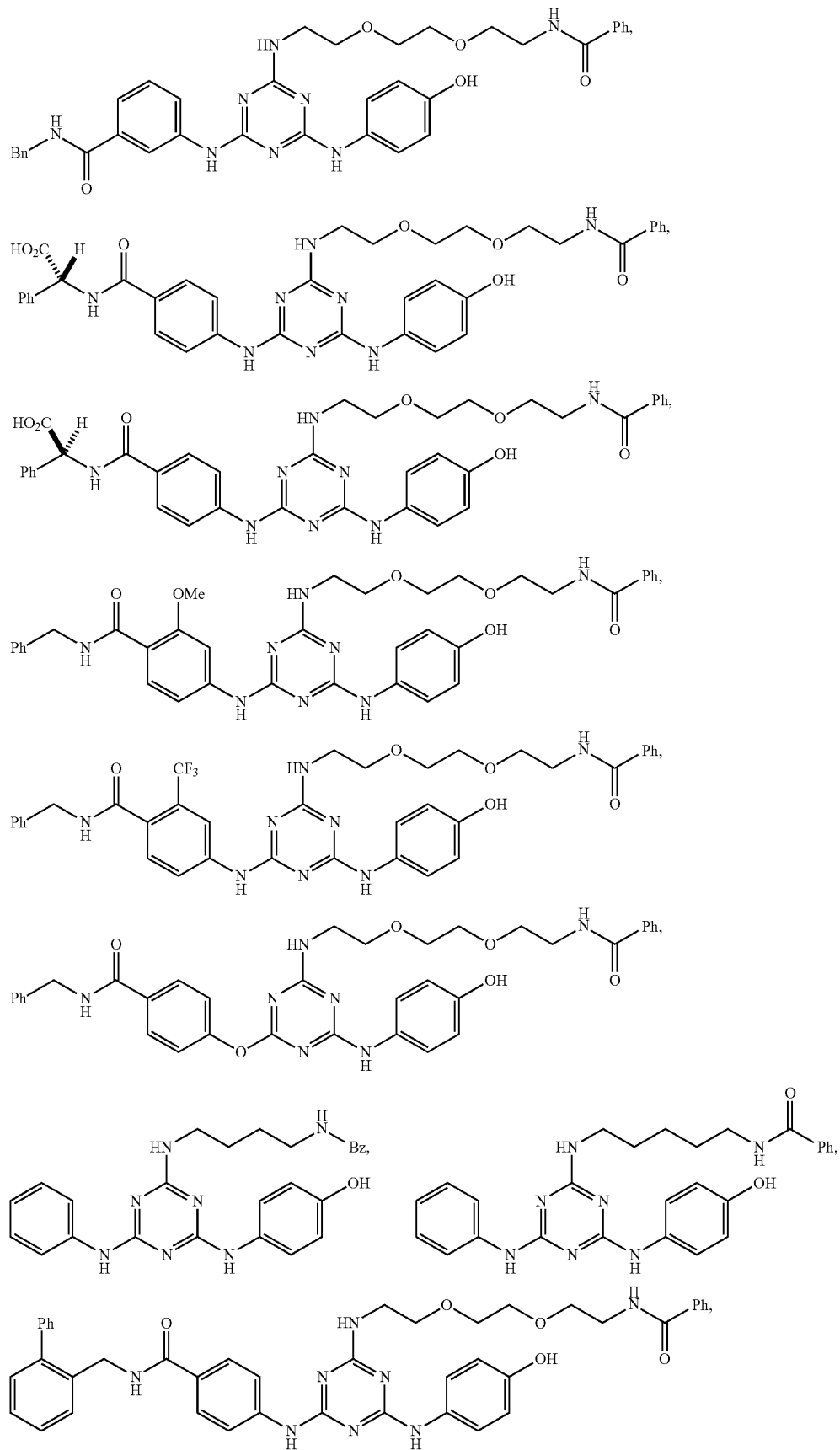

-continued
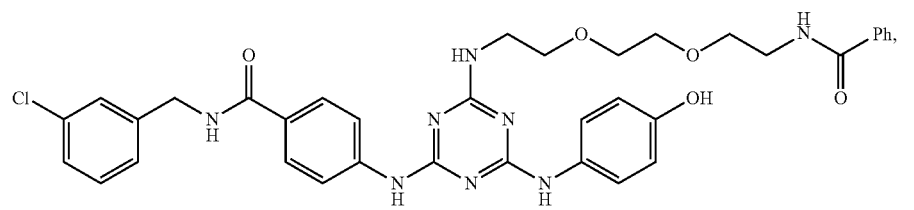 [SMILES: O=C(NCCOCCOCCNc1nc(Nc2ccc(O)cc2)nc(Nc2ccc(C(=O)NCc3cccc(Cl)c3)cc2)n1)c1ccccc1]
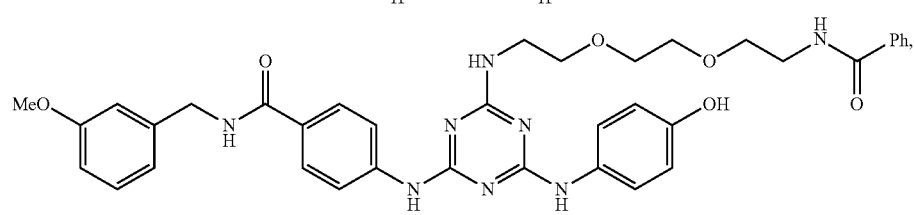
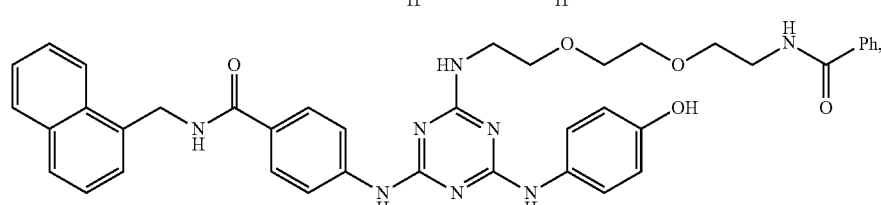
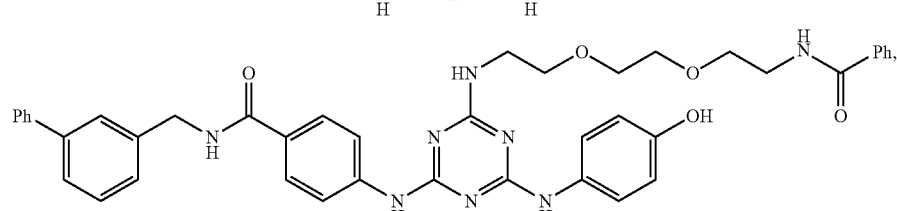
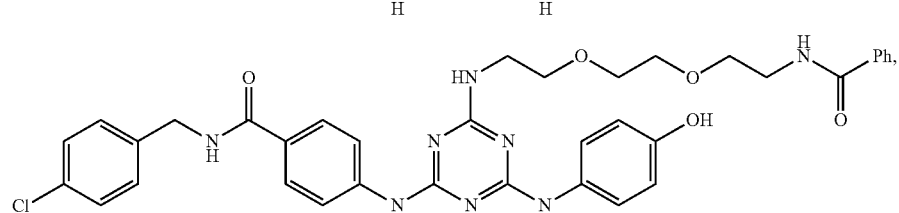
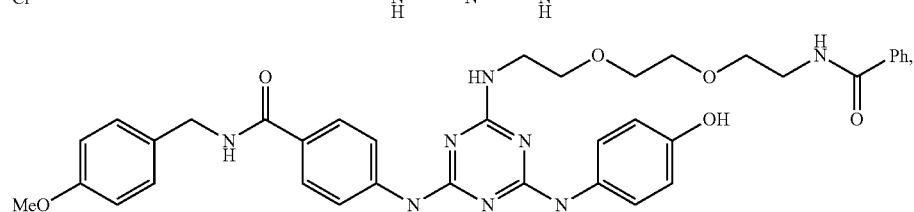
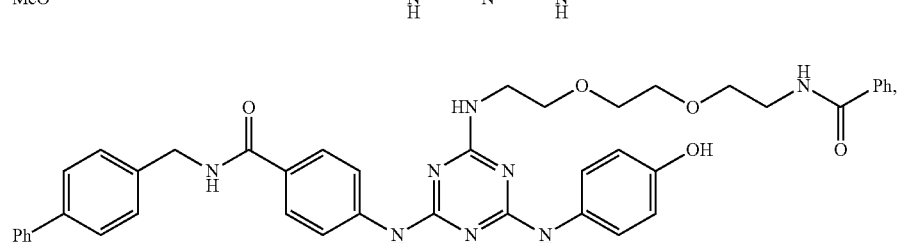
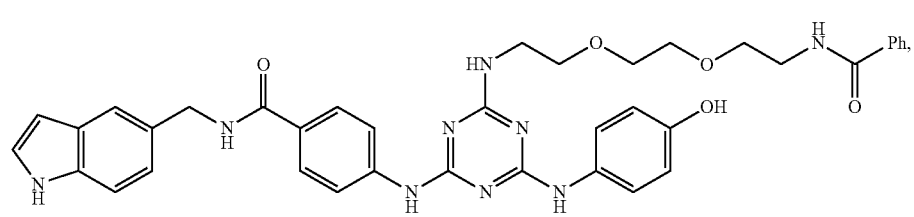 [SMILES: O=C(NCCOCCOCCNc1nc(Nc2ccc(O)cc2)nc(Nc2ccc(C(=O)NCc3ccc4[nH]ccc4c3)cc2)n1)c1ccccc1]

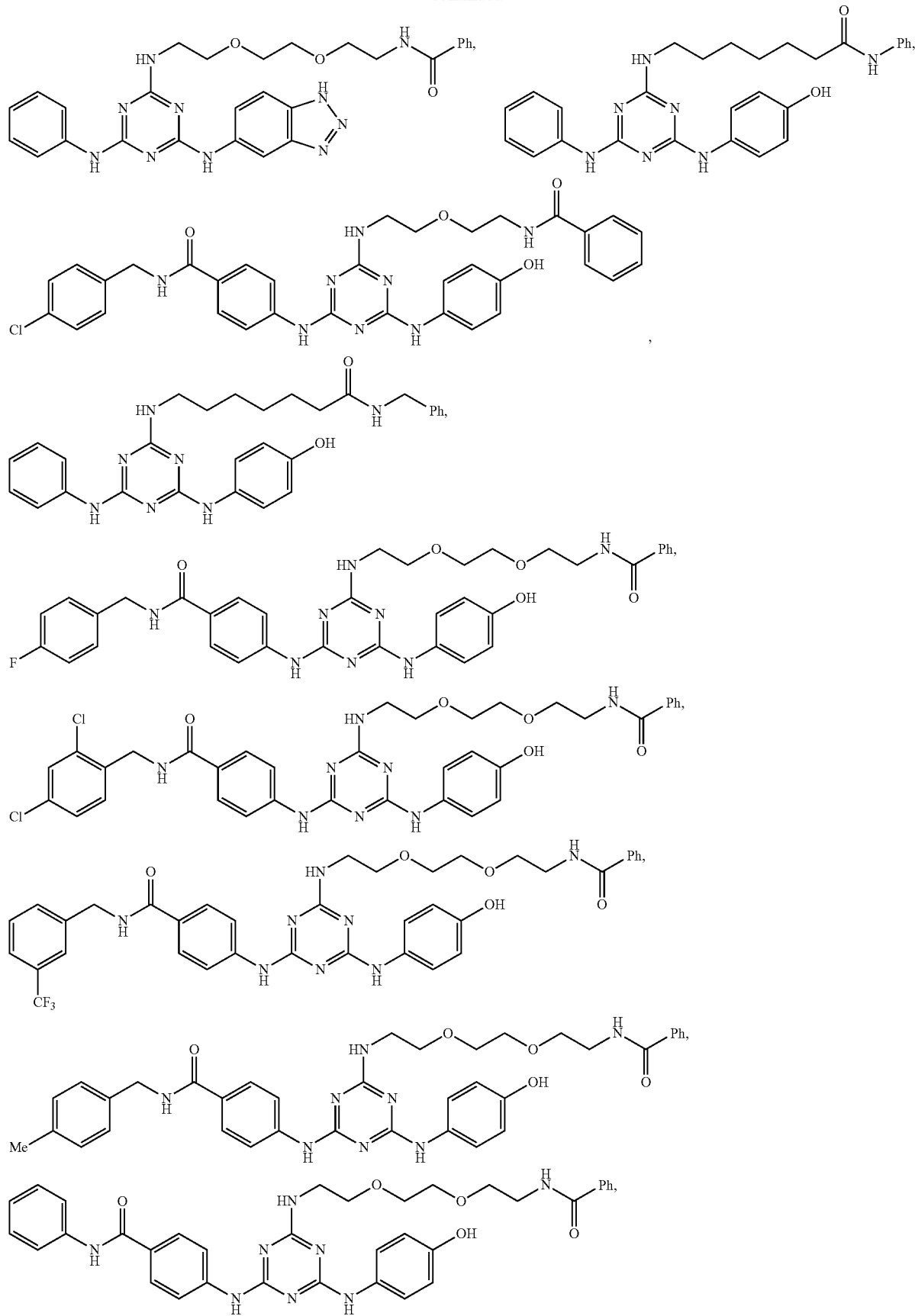

-continued
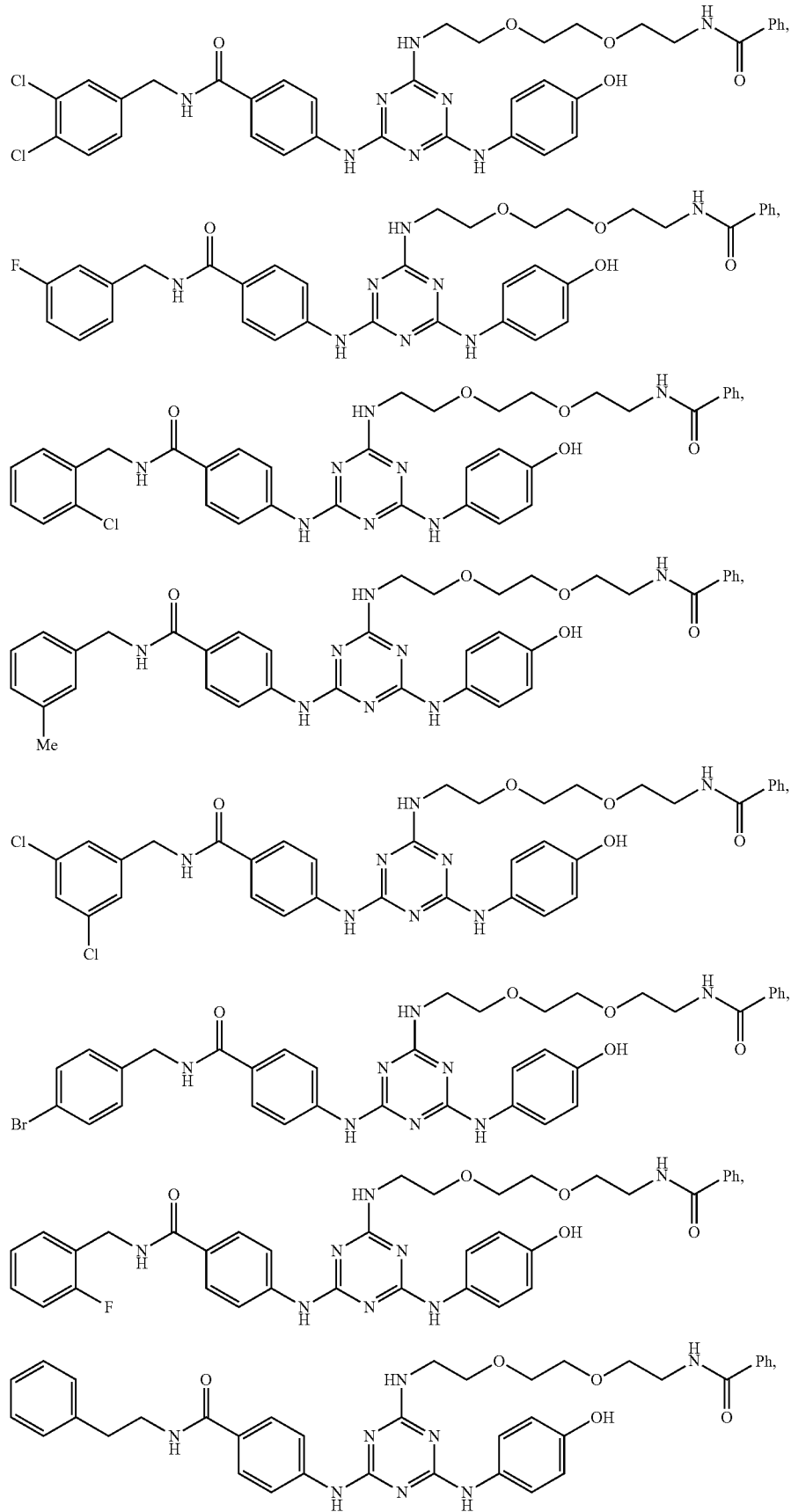

-continued
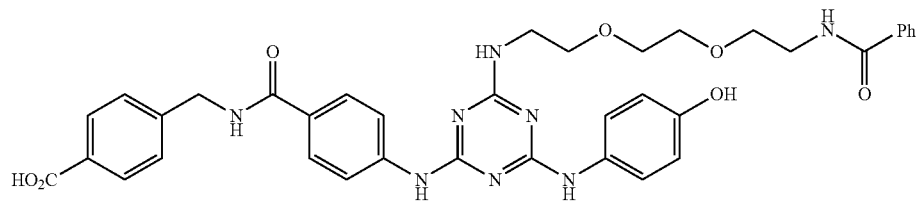
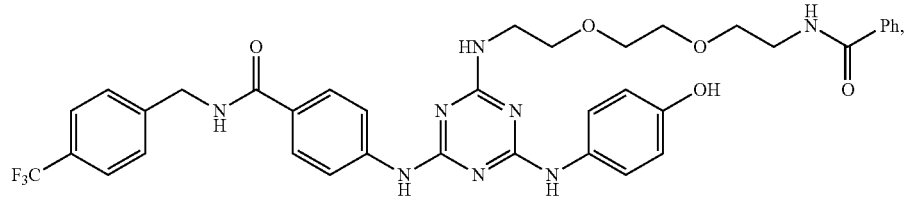 [SMILES: O=C(NCCOCCOCCNc1nc(Nc2ccc(O)cc2)nc(Nc2ccc(C(=O)NCc3ccc(Br)cc3)cc2)n1)c1ccccc1]
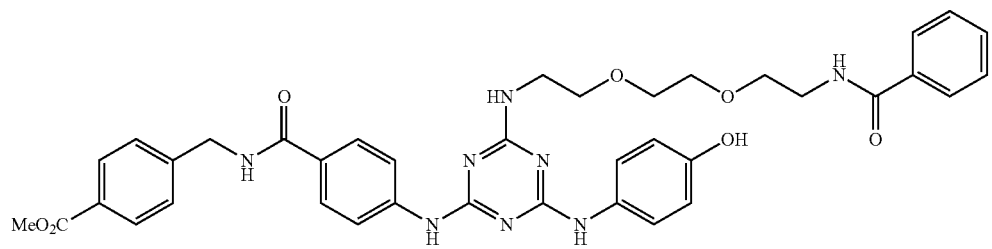 [SMILES: COC(=O)c1ccc(CNC(=O)c2ccc(Nc3nc(NCCOCCOCCNC(=O)c4ccccc4)nc(Nc4ccc(O)cc4)n3)cc2)cc1]
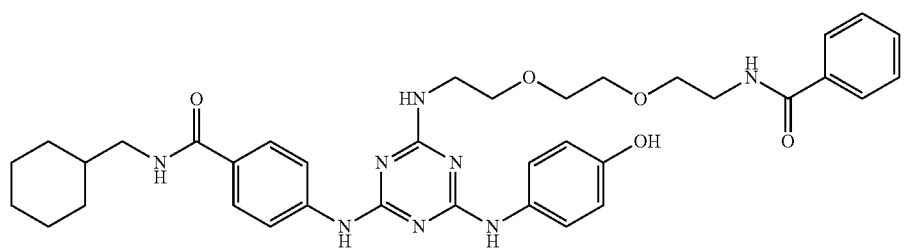 [SMILES: O=C(NCCOCCOCCNc1nc(Nc2ccc(O)cc2)nc(Nc2ccc(C(=O)NCC3CCCCC3)cc2)n1)c1ccccc1]
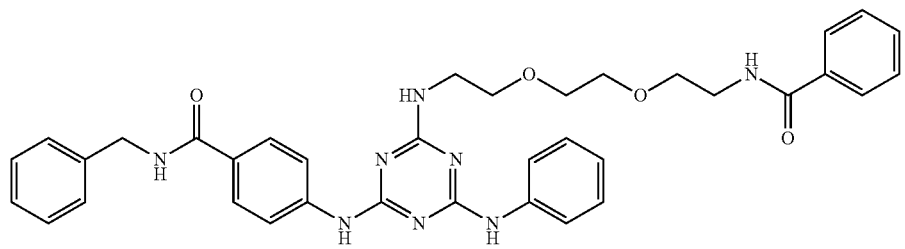 [SMILES: O=C(NCCOCCOCCNc1nc(Nc2ccc(O)cc2)nc(Nc2ccc(C(=O)NCc3ccccc3)cc2)n1)c1ccccc1]
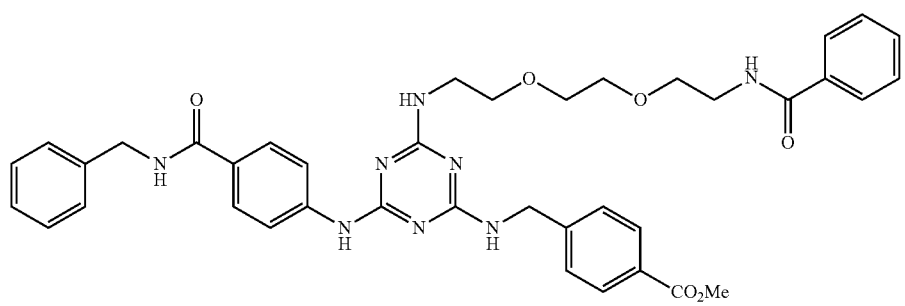 [SMILES: COC(=O)c1ccc(CNc2nc(NCCOCCOCCNC(=O)c3ccccc3)nc(Nc3ccc(C(=O)NCc4ccccc4)cc3)n2)cc1]
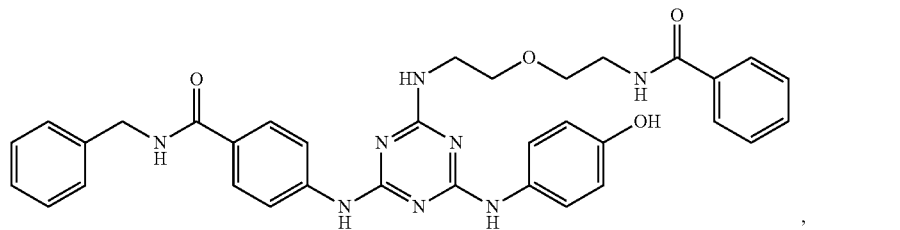

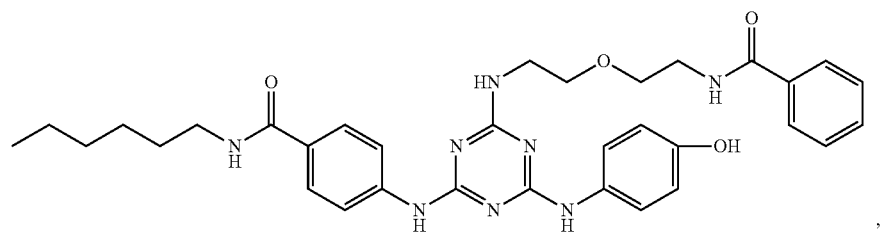
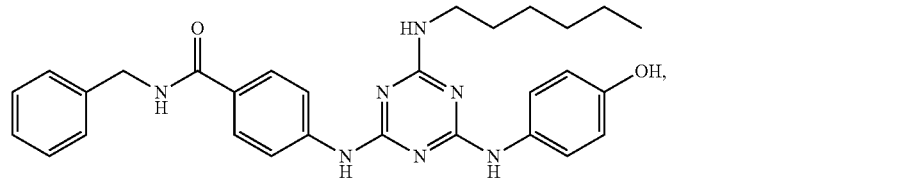
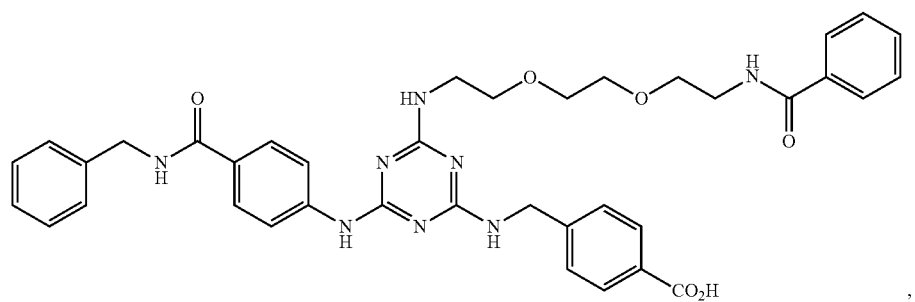
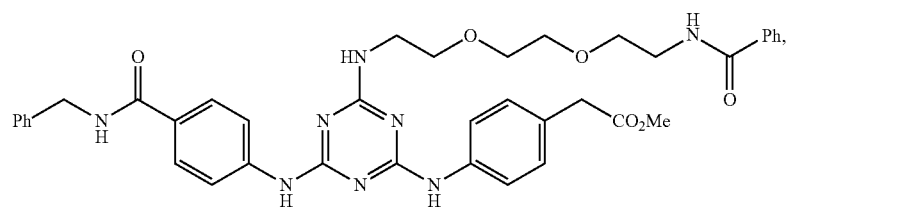
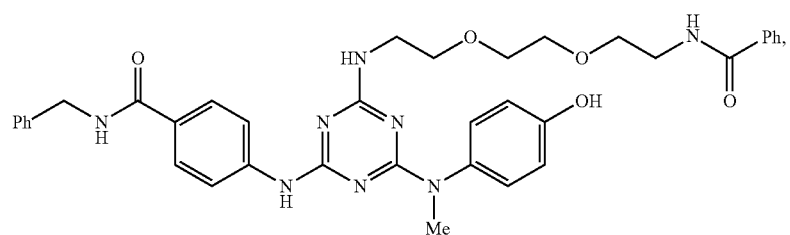
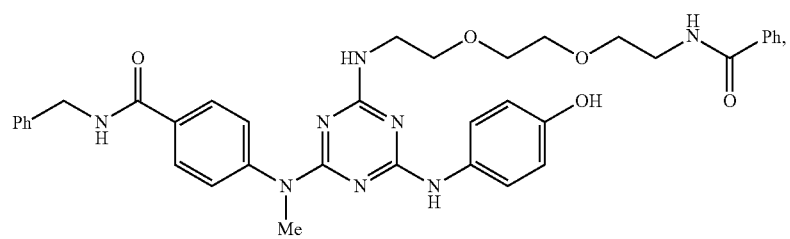
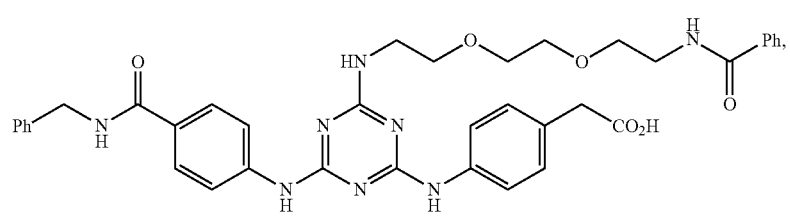

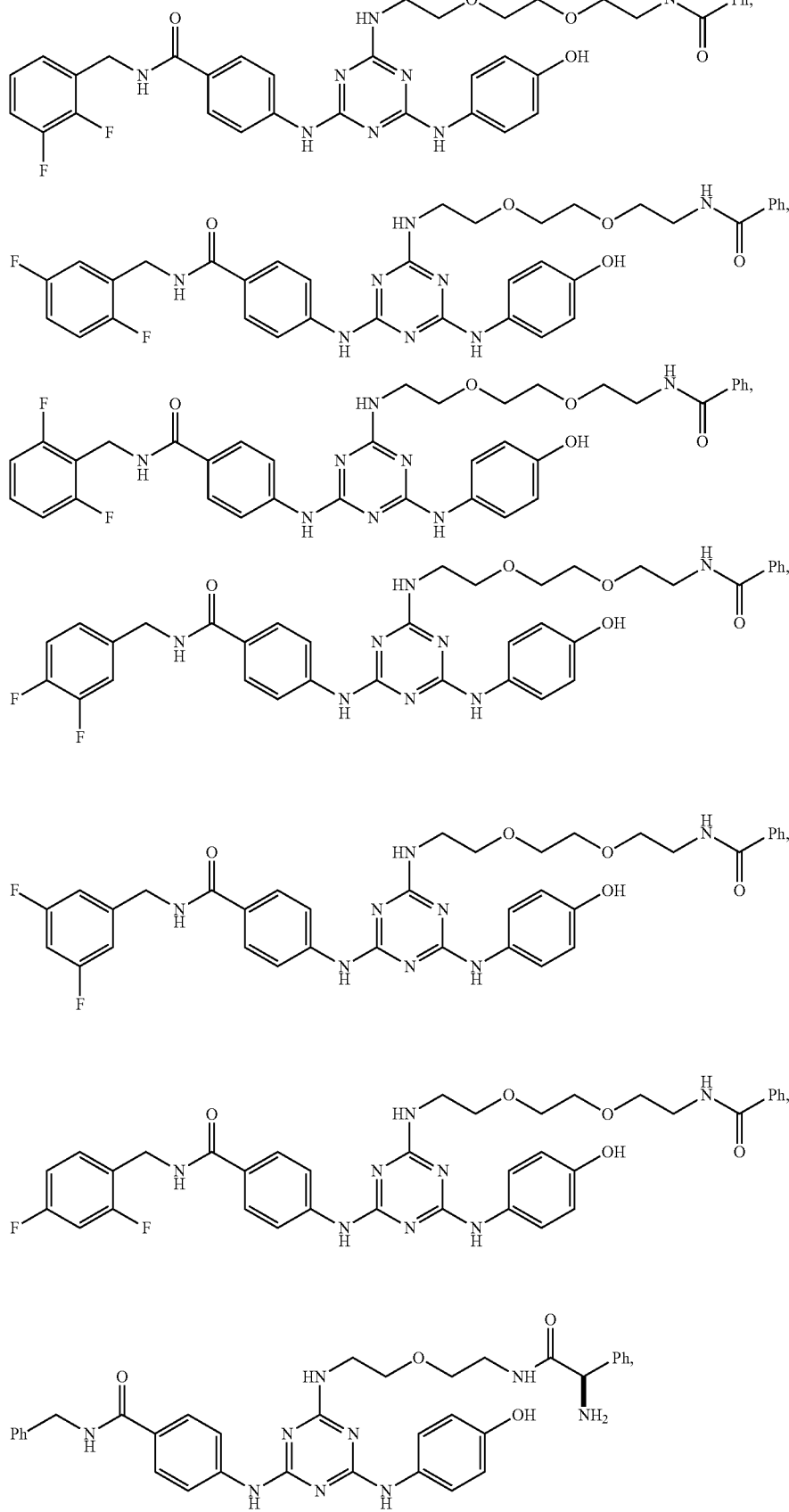

-continued
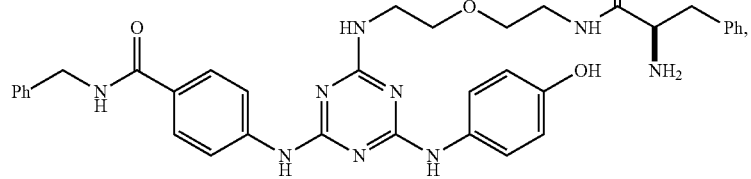
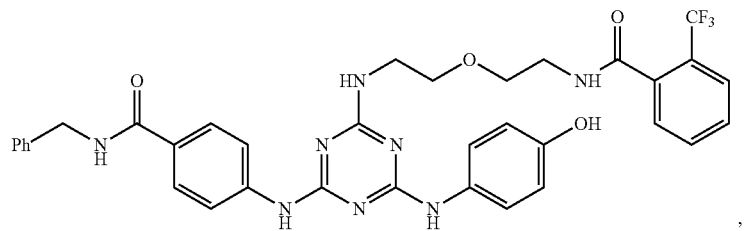
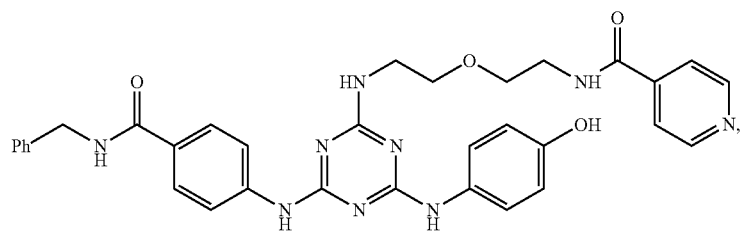 [SMILES: O=C(NCCOCCNc1nc(Nc2ccc(O)cc2)nc(Nc2ccc(C(=O)NCc3ccccc3)cc2)n1)c1ccncc1]
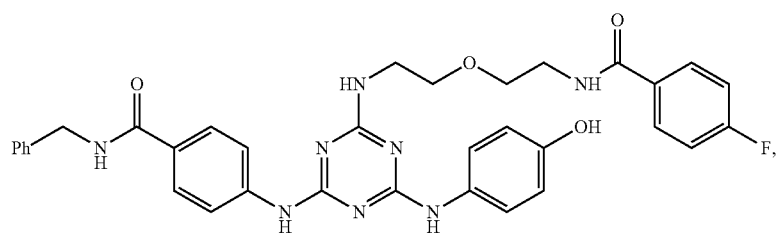
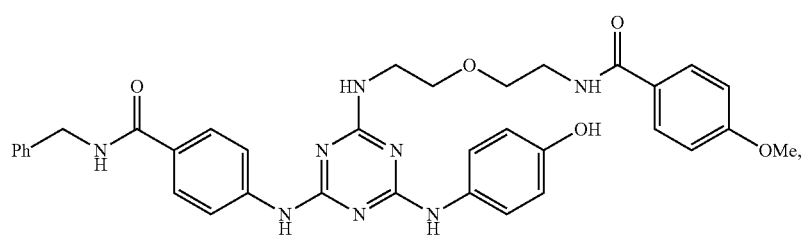 [SMILES: COc1ccc(C(=O)NCCOCCNc2nc(Nc3ccc(O)cc3)nc(Nc3ccc(C(=O)NCc4ccccc4)cc3)n2)cc1]
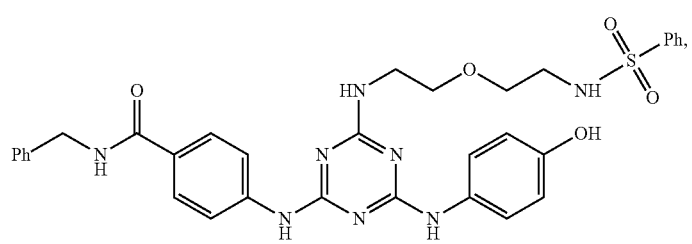
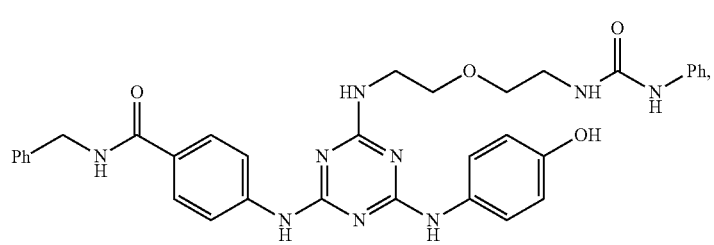

-continued
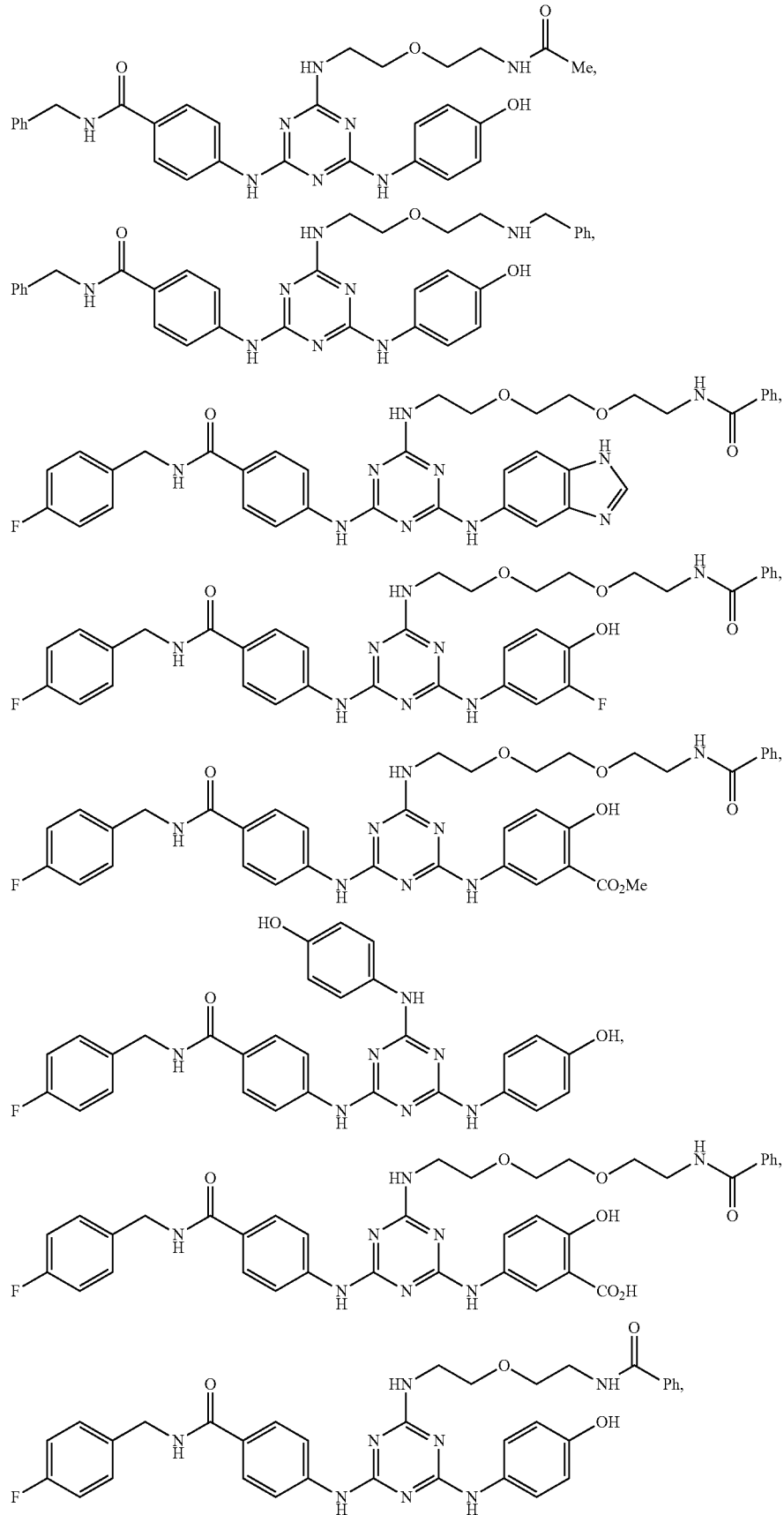

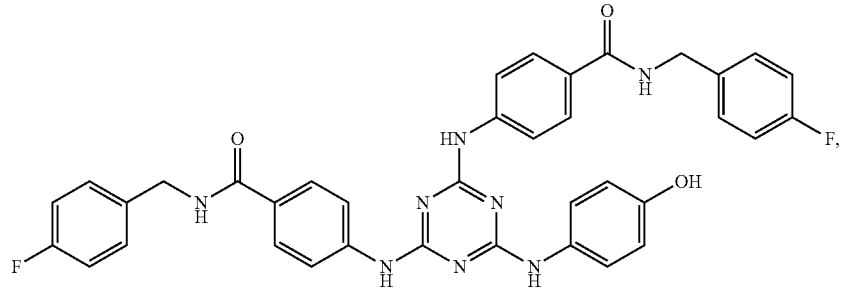 [SMILES: O=C(NCc1ccc(F)cc1)c1ccc(Nc2nc(Nc3ccc(O)cc3)nc(Nc3ccc(C(=O)NCc4ccc(F)cc4)cc3)n2)cc1]
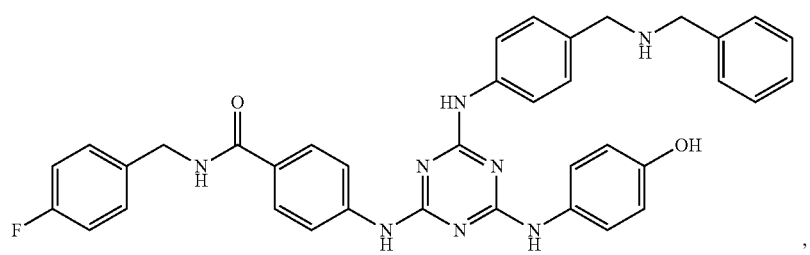
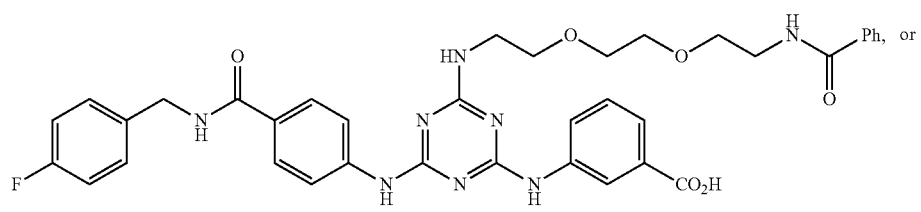
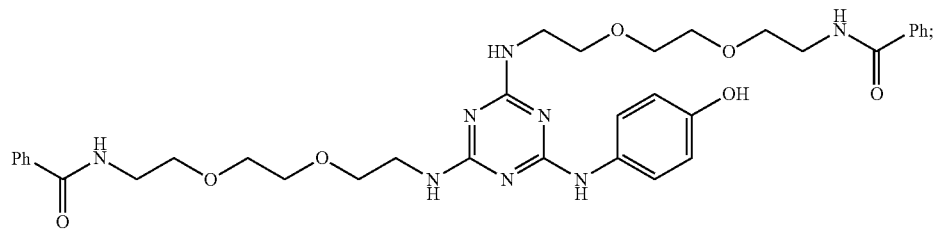 [SMILES: O=C(NCCOCCOCCNc1nc(NCCOCCOCCNC(=O)c2ccccc2)nc(Nc2ccc(O)cc2)n1)c1ccccc1]
or a pharmaceutically acceptable salt thereof.
23. The method of claim 1, wherein the compound has the structure:
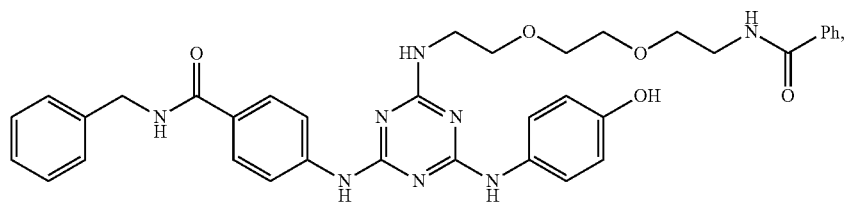
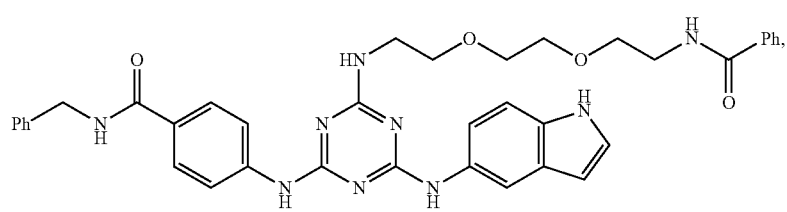

-continued
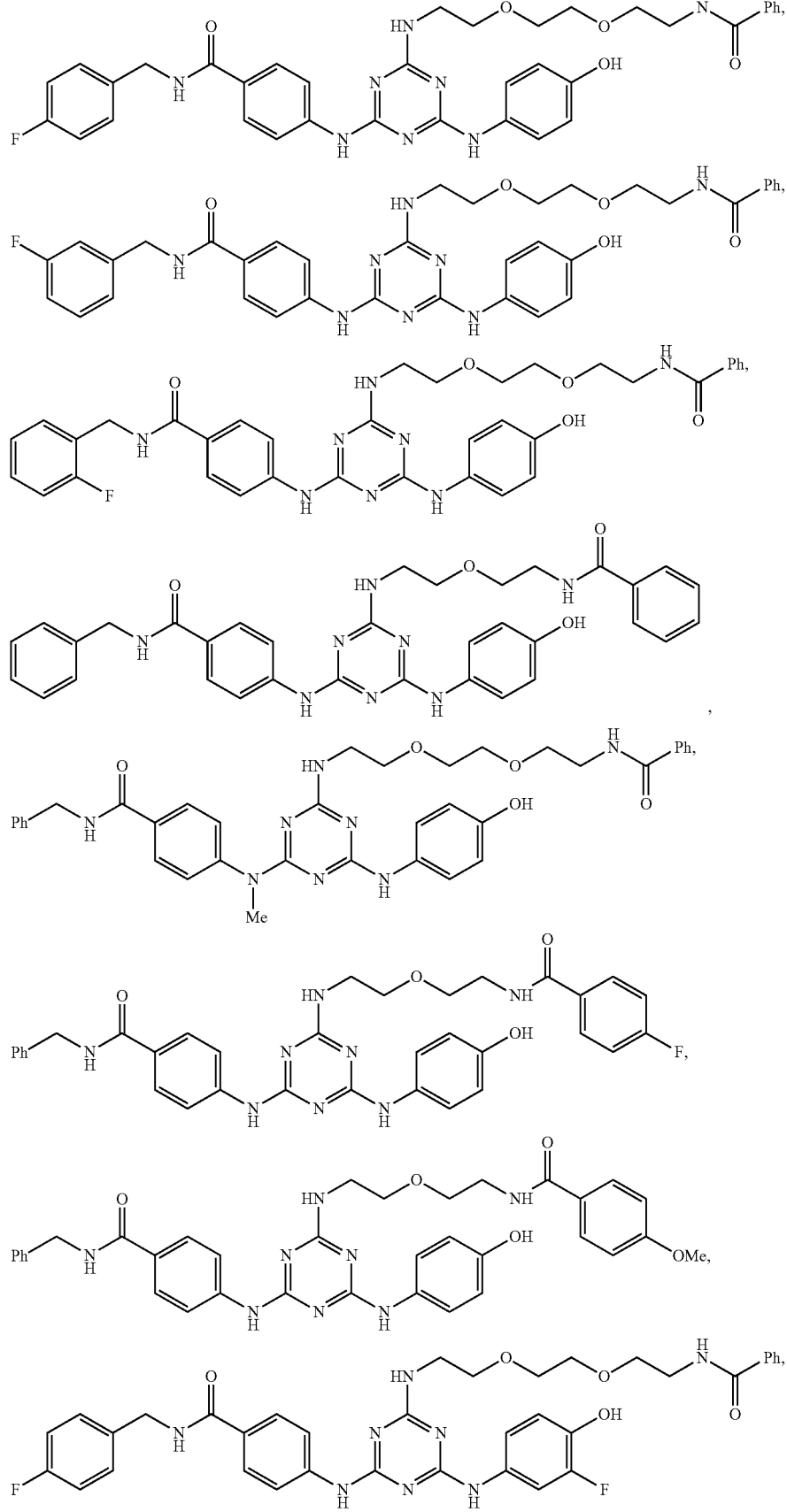

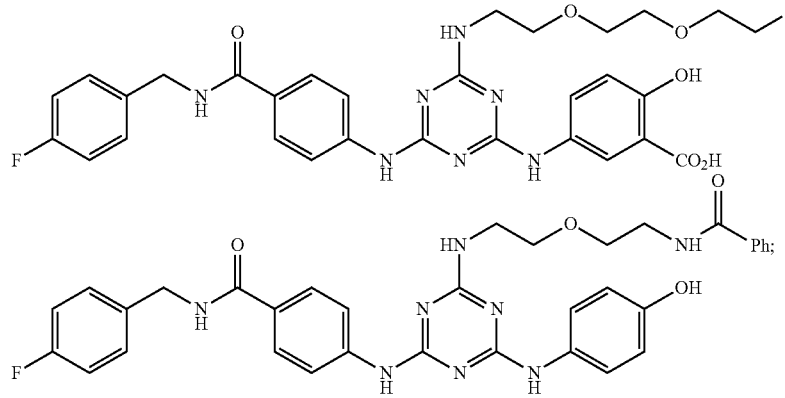
or a pharmaceutically acceptable salt thereof.
24. The method of claim 1, wherein the compound has the structure:
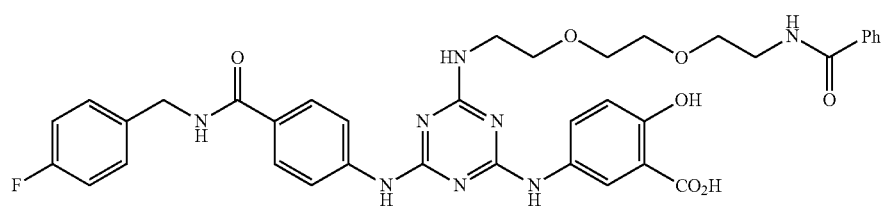 [SMILES: O=C(NCCOCCOCCNc1nc(Nc2ccc(C(=O)NCc3ccc(F)cc3)cc2)nc(Nc2ccc(O)c(C(=O)O)c2)n1)c1ccccc1]
or a pharmaceutically acceptable salt thereof.
* * * * *